United States Patent
Hunt et al.

(10) Patent No.: US 11,760,731 B2
(45) Date of Patent: Sep. 19, 2023

(54) POLYMORPHS OF PYRIMIDINE CYCLOHEXYL GLUCOCORTICOID RECEPTOR MODULATORS

(71) Applicant: Corcept Therapeutics Incorporated, Menlo Park, CA (US)

(72) Inventors: Hazel Joan Hunt, West Sussex (GB); Lorraine Donaghy, West Sussex (GB); Keith Lorimer, West Sussex (GB); Nathan Jay Dixon, West Sussex (GB); Jeffrey Mark Dener, Menlo Park, CA (US)

(73) Assignee: Corcept Therapeutics Incorporated, Menlo Park, CA (US)

( * ) Notice: Subject to any disclaimer, the term of this patent is extended or adjusted under 35 U.S.C. 154(b) by 0 days.

(21) Appl. No.: 18/061,745

(22) Filed: Dec. 5, 2022

(65) Prior Publication Data

US 2023/0212128 A1 Jul. 6, 2023

Related U.S. Application Data

(63) Continuation of application No. 17/308,380, filed on May 5, 2021, now Pat. No. 11,548,856.

(60) Provisional application No. 63/128,534, filed on Dec. 21, 2020, provisional application No. 63/020,916, filed on May 6, 2020.

(51) Int. Cl.
C07D 239/54 (2006.01)

(52) U.S. Cl.
CPC ........ *C07D 239/54* (2013.01); *C07B 2200/13* (2013.01)

(58) Field of Classification Search
CPC .......................... C07D 239/54; C07B 2200/13
See application file for complete search history.

(56) References Cited

U.S. PATENT DOCUMENTS

| | | | |
|---|---|---|---|
| 6,852,719 B2 | 2/2005 | Liu et al. | |
| 7,576,076 B2 | 8/2009 | Clark et al. | |
| 7,799,782 B2 | 9/2010 | Munson et al. | |
| 8,173,664 B2 | 5/2012 | Clark et al. | |
| 8,685,973 B2 | 4/2014 | Clark et al. | |
| 8,906,917 B2 | 12/2014 | Clark et al. | |
| 9,321,736 B2 | 4/2016 | Clark et al. | |
| 9,626,979 B2 | 4/2017 | Sung et al. | |
| 10,238,659 B2 | 3/2019 | Belanoff et al. | |
| 10,881,660 B2 | 1/2021 | Belanoff et al. | |
| 11,542,238 B2 | 1/2023 | Hunt et al. | |
| 11,548,856 B2 | 1/2023 | Hunt et al. | |
| 2013/0072486 A1 | 3/2013 | Clark et al. | |
| 2021/0238148 A1 | 8/2021 | Hunt et al. | |
| 2021/0361651 A1 | 11/2021 | Chia et al. | |
| 2021/0363112 A1 | 11/2021 | Hunt et al. | |
| 2022/0220081 A1 | 7/2022 | Dener et al. | |

FOREIGN PATENT DOCUMENTS

| | | |
|---|---|---|
| EP | 0037495 A1 | 10/1981 |
| EP | 0369627 A2 | 5/1990 |
| EP | 0722732 A1 | 7/1996 |
| EP | 2313212 A1 | 4/2011 |
| JP | H06128238 A | 5/1994 |
| JP | H1017555 A | 1/1998 |
| JP | 2000271618 A | 10/2000 |
| WO | 0244120 A1 | 6/2002 |
| WO | 03084935 A2 | 10/2003 |
| WO | 2005105036 A1 | 11/2005 |
| WO | 2009014141 A1 | 1/2009 |
| WO | 2010052445 A1 | 5/2010 |
| WO | 2011132094 A2 | 10/2011 |
| WO | 2012129074 A1 | 9/2012 |
| WO | 2016061195 A1 | 4/2016 |
| WO | 2018236749 A2 | 12/2018 |
| WO | 2019236487 A1 | 12/2019 |
| WO | 2020190351 | * 9/2020 |
| WO | 2020190351 A1 | 9/2020 |
| WO | 2021226258 A1 | 11/2021 |

OTHER PUBLICATIONS

International Search Report and Written Opinion issued in related International Patent Application. No. PCT/US2005/023675, dated Dec. 13, 2005, 11 pages.
International Search Report and Written Opinion issued in related International Patent Application. No. PCT/US2012/029376, dated Jun. 27, 2012, 8 pages.
International Search Report and Written Opinion issued in related International Patent Application No. PCT/US2019/035229, dated Oct. 1, 2019, 10 pages.
International Search Report and Written Opinion received for PCT Application No. PCT/US2021/030923, dated Aug. 18, 2021, 11 pages.
International Search Report and Written Opinion received for PCT Application No. PCT/US2021/030925, dated Aug. 20, 2021, 14 pages.
Ali et al. (Apr. 2, 2004) "Novel N-Arylpyrazolo[3,2-c]-Based Ligands for the Glucocorticoid Receptor: Receptor Binding and in Vivo Activity", J. Med. Chem., 47(10):2441-2452.
Baptista, T. (Jul. 1999) "Body Weight Gain Induced by Antipsychotic Drugs: Mechanisms and Management", Acta Psychiatr Scand, 100(1):3-16.
Bertagna et al. (Jul. 1984) "The New Steroid Analog RU 486 Inhibits Glucocorticoid Action in Man", The Journal of Clinical Endocrinology Metabolism, 59(1):25-28.
Bhuyan et al. (1998) "Studies on Uracils: Synthesis of Novel Uracil Analogues via 1,5- and 1,6-Intramolecular Cycloaddition Reactions", Journal of Chemical Research, Synopses, 9:502-503.

(Continued)

*Primary Examiner* — D Magaret M Seaman
(74) *Attorney, Agent, or Firm* — Mintz, Levin, Cohn, Ferris, Glovsky and Popeo, P.C.

(57) ABSTRACT

The present invention provides crystalline forms of (E)-6-(4-Phenylcyclohexyl)-5-(3-trifluoromethylbenzyl)-1H-pyrimidine-2,4-dione, and methods of making and using the same.

17 Claims, 32 Drawing Sheets

(56) References Cited

OTHER PUBLICATIONS

Bledsoe et al. (Jul. 12, 2002) "Crystal Structure of the Glucocorticoid Receptor Ligand Binding Domain Reveals a Novel Mode of Receptor Dimerization and Coactivator Recognition", Cell, 110(1):93-105.

Brophy et al. (Jan. 1983) "Bioavailability of Oral Dexamethasone During High Dose Steroid Therapy in Neurological Patients", European Journal of Clinical Pharmacology, 24:103-108.

Cadepond et al. (1997) "RU486 (Mifepristone): Mechanisms of Action and Clinical Uses", Annu Rev Med, 48:129-156.

Dorwald Florencio Z. (2005) "Side Reactions in Organic Synthesis: A Guide to Successful Synthesis Design", Wiley, VCH, 390 pages.

Eyles et al. (Jul. 1997) "Oral Delivery and Fate of Poly(Lactic Acid) Microsphere-Encapsulated Interferon in Rats", Journal of Pharmacy and Pharmacology, 49(7):669-674.

Fotherby (Aug. 1996) "Bioavailability of Orally Administered Sex Steroids Used in Oral Contraception and Hormone Replacement Therapy", Contraception, 54(2):59-69.

Fukazawa et al. (1998) "6-Amino-5-Methyluracil Derivativies and Their Use as Thymidine Phosphorylase Inhibitors and Neovascularization Inhibitors", XP002355358; Database CA 'Online'; Chemical Abstracts Service, Columbus, OH, US; Database Accession No. 1998:59356, 4 pages.

Gao et al. (Jun. 1995) "Controlled Release of a Contraceptive Steroid from Biodegradable and Injectable Gel Formulations: In Vitro Evaluation", Pharmaceutical Research, 12(6):857-863.

Groning et al. (May 1996) "Three-dimensional Solubility Parameters and Their Use in Characterising the Permeation of Drugs Through the Skin", Pharmazie, 51(5):337-341.

Hidalgo-Aragones et al. (Aug. 1996) "Pharmacokinetics of oestrone-3-O-sulphamate", The Journal of Steroid Biochemistry and Molecular Biology, 58(5-6):611-617.

Hunt et al. (Dec. 15, 2012) "Discovery of a Novel Non-steroidal GR Antagonist With in Vivo Efficacy in the Olanzapine-induced Weight Gain Model in the Rat", Bioorganic & Medicinal Chemistry Letters, 22(24):7376-7380.

Johnson et al. (Sep. 1995) "Permeation of Steroids through Human Skin", Journal of Pharmaceutical Sciences, 84(9):1144-1146.

Koorneef et al. (2018) "Selective Glucocorticoid Receptor Modulation Prevents and Reverses Nonalcoholic Fatty Liver Disease In Male Mice", Endocrinology, 159(12):3925-3936.

Lee et al. (2020) "Reversal of Antipsychotic-induced Weight Gain in Rats with Miricorilant, A Selective Glucocorticoid Receptor (Gr) Modulator", American Psychiatric Association Annual Meeting, 1 Page.

Minto et al. (Apr. 1, 1997) "Pharmacokinetics and Pharmacodynamics of Nandrolone Esters in Oil Vehicle: Effects of Ester, Injection Site and Injection Volume", The Journal of Pharmacology and Experimental Therapeutics, 281(1):93-102.

Nguyen et al. (Sep. 1, 2017) "A Mixed Glucocorticoid/mineralocorticoid Receptor Modulator Dampens Endocrine and Hippocampal Stress Responsivity in Male Rats", Physiology & Behavior, 178:82-92.

Rao K. Paduranga (1995) "Recent Developments of Collagen-Based Materials for Medical Applications and Drug Delivery Systems", Journal of Biomaterials Science, Polymer Edition, 7(7):623-645.

Rohatagi et al. (1995) "Pharmacokinetic and Pharmacodynamic Evaluation of Triamcinolone Acetonide After Intravenous, Oral, and Inhaled Administration", Journal of Clinical Pharmacology, 35(12):1187-1193.

Rohatagi et al. (Sep. 1, 1995) "Pharmacokinetic Interaction Between Endogenous Cortisol and Exogenous Corticosteroids", Die Pharmazie, 50(9):610-613.

Teutsch et al. (Nov. 1, 1991) "Design of Ligands for the Glucocorticoid and Progestin Receptors", Biochemical Society Transactions, 19(4):901-908.

Tjwa et al. (1995) "Budesonide Inhaled Via Turbuhaler: A More Effective Treatment for Asthma than Beclomethasone Dipropionate Via Rotahaler", Annals of Allergy, Asthma & Immunology, 75(2):107-111.

Turner et al. (Oct. 2005) "Structure of the Glucocorticoid Receptor (NR3C1) Gene 5' Untranslated Region: Identification, and Tissue Distribution of Multiple New Human Exon 1", Journal Molecular Endocrinol, 5(2):283-292.

Umbricht et al. (Sep. 1994) "Clozapine and Weight Gain", The Journal of Clinical Psychiatry, 55(Suppl B):157-160.

\* cited by examiner

FIG. 2
Compound I Form B, XRPD Peak Table

| Angle/ ° 2θ | Rel. Int. [%] | Angle/ ° 2θ | Rel. Int. [%] |
|---|---|---|---|
| 4.32 | 2.38 | 23.60 | 28.64 |
| 8.95 | 2.56 | 23.80 | 6.1 |
| 9.51 | 2.33 | 24.07 | 3.82 |
| 9.83 | 10.41 | 24.36 | 11.39 |
| 10.37 | 7.7 | 25.37 | 7.56 |
| 10.58 | 4.96 | 25.58 | 6.27 |
| 11.21 | 5.73 | 25.74 | 24.12 |
| 11.77 | 5.49 | 26.31 | 5.21 |
| 13.01 | 4.1 | 26.51 | 3.4 |
| 13.40 | 21.04 | 26.78 | 3.92 |
| 13.69 | 7.35 | 27.10 | 3.01 |
| 14.03 | 4.49 | 27.36 | 2.53 |
| 14.33 | 4.4 | 27.84 | 2.68 |
| 14.78 | 13.64 | 28.12 | 5.39 |
| 15.43 | 1.41 | 28.70 | 5.42 |
| 15.79 | 24.83 | 29.41 | 2.11 |
| 16.20 | 23.89 | 29.67 | 2.41 |
| 16.56 | 8.57 | 29.86 | 3.22 |
| 16.73 | 35.51 | 30.85 | 1.43 |
| 17.03 | 74.86 | 31.33 | 2.86 |
| 17.32 | 67.69 | 31.87 | 3.29 |
| 17.74 | 55.03 | 31.99 | 3.51 |
| 18.01 | 22.65 | 32.36 | 1.27 |
| 18.38 | 2.08 | 32.77 | 2.39 |
| 19.00 | 100 | 33.95 | 4.75 |
| 19.62 | 33.42 | 34.26 | 3.51 |
| 20.25 | 6.13 | 34.49 | 1.73 |
| 20.45 | 10.29 | 35.05 | 1.59 |
| 20.83 | 5.76 | 35.53 | 3.27 |
| 21.03 | 7.87 | 36.39 | 1.8 |
| 21.32 | 24.22 | 36.60 | 3.84 |
| 21.76 | 2.85 | 37.24 | 5.15 |
| 22.01 | 5.69 | 37.72 | 2.22 |
| 22.28 | 5.32 | 38.55 | 2.35 |
| 22.67 | 9.05 | 39.05 | 2.32 |
| 23.06 | 3.04 | | |
| 23.40 | 2.79 | | |

Compound I Form B, DSC & TGA Thermogram

FIG. 5

Compound I Form A, XRPD Peak Table

| Angle/ ° 2θ | Rel. Int. [%] | Angle/ ° 2θ | Rel. Int. [%] |
|---|---|---|---|
| 4.72 | 2.31 | 22.10 | 36.31 |
| 5.41 | 6.66 | 22.34 | 84.71 |
| 7.92 | 6.24 | 22.86 | 6 |
| 9.46 | 19.31 | 23.30 | 10.63 |
| 9.88 | 9.38 | 24.13 | 9.47 |
| 10.90 | 3.67 | 24.27 | 7.98 |
| 11.85 | 3.05 | 25.27 | 5.44 |
| 12.89 | 9.52 | 26.05 | 3.6 |
| 13.40 | 4.11 | 26.42 | 4.16 |
| 13.70 | 7.63 | 27.03 | 7.34 |
| 14.02 | 14.41 | 27.99 | 4.71 |
| 15.46 | 17.04 | 28.48 | 8.32 |
| 15.98 | 6.63 | 29.79 | 4.13 |
| 16.27 | 34.79 | 30.23 | 3.33 |
| 16.55 | 5.61 | 31.01 | 2.96 |
| 17.06 | 100 | 31.36 | 4.83 |
| 17.95 | 2.42 | 32.39 | 4.15 |
| 18.52 | 28.02 | 33.66 | 7.57 |
| 18.70 | 66.07 | 34.88 | 2.89 |
| 19.10 | 7.89 | 36.41 | 6.17 |
| 19.47 | 25.6 | 38.18 | 6.34 |
| 19.90 | 49.03 | 38.79 | 4.77 |
| 20.56 | 2.39 | | |
| 21.31 | 13.41 | | |

FIG. 7 Compound I Form C, XRPD Diffractogram

FIG. 8

Compound I Form C, XRPD Peak Table

| Angle/ °2θ | Rel. Int. [%] | Angle/ °2θ | Rel. Int. [%] |
|---|---|---|---|
| 8.5968 | 8.18 | 23.1441 | 4.56 |
| 8.7715 | 29.7 | 24.2464 | 3.13 |
| 9.2166 | 4.89 | 24.7742 | 5.59 |
| 10.6438 | 21.54 | 25.1467 | 5.05 |
| 12.5512 | 4.54 | 26.1974 | 14.56 |
| 14.2874 | 15.79 | 27.5529 | 26.67 |
| 14.5478 | 8.58 | 28.2235 | 1.25 |
| 15.0668 | 21.24 | 28.8021 | 6.81 |
| 15.3725 | 2.02 | 29.2054 | 5.34 |
| 17.252 | 30.5 | 30.3916 | 6.69 |
| 17.6808 | 11.39 | 31.8511 | 3.05 |
| 17.9449 | 100 | 32.4429 | 4.17 |
| 18.3069 | 36.23 | 33.4199 | 4.15 |
| 18.4428 | 38.64 | 34.9298 | 3.68 |
| 19.0805 | 4.45 | 35.3256 | 3.26 |
| 19.3086 | 15.05 | 35.8468 | 2.02 |
| 19.7135 | 2.55 | 37.0538 | 2.59 |
| 19.9457 | 6 | 38.2488 | 5.07 |
| 21.33 | 38.45 | 38.8126 | 2.82 |
| 21.8022 | 70.77 | 39.3086 | 3.21 |
| 22.5372 | 17.23 | | |
| 22.6993 | 9.41 | | |

Compound I Form C, DSC Thermogram

Compound I Form F, XRPD Diffractogram

FIG. 11

Compound I Form F, XRPD Peak Table

| Angle/ ° 2θ | Rel. Int. [%] |
|---:|---:|
| 4.2009 | 9.93 |
| 8.389 | 6.03 |
| 9.3401 | 16.45 |
| 9.7053 | 15.25 |
| 10.313 | 9.18 |
| 11.3592 | 7.01 |
| 11.8588 | 6.31 |
| 12.6048 | 10.33 |
| 12.9859 | 7.93 |
| 14.0575 | 13.5 |
| 14.2686 | 13.01 |
| 15.9348 | 98.33 |
| 16.352 | 47.29 |
| 16.7814 | 100 |
| 17.3092 | 41.9 |
| 17.8498 | 23.94 |
| 18.4663 | 7.84 |
| 19.0408 | 70.73 |
| 19.4119 | 37 |
| 20.4308 | 25.47 |
| 20.6791 | 19.64 |
| 21.0936 | 50.73 |
| 21.5416 | 15.05 |
| 22.257 | 11.36 |
| 23.2335 | 10.6 |
| 23.828 | 13.07 |
| 25.0935 | 13.95 |
| 25.7941 | 46.7 |
| 26.689 | 18.52 |
| 28.2507 | 10.6 |
| 28.6687 | 7.55 |
| 31.181 | 10.75 |
| 34.0514 | 9.48 |
| 35.2749 | 12.49 |
| 37.2555 | 10.6 |

Compound I Form F, DSC Thermogram

FIG. 14

Compound I THF solvate Form H, XRPD Peak Table

| Angle/ ° 2θ | Rel. Int. [%] | Angle/ ° 2θ | Rel. Int. [%] |
|---|---|---|---|
| 7.9171 | 21.19 | 25.0068 | 47.63 |
| 8.5885 | 3.55 | 25.597 | 42.31 |
| 9.7248 | 3.31 | 26.2282 | 8.28 |
| 10.9703 | 20 | 26.4296 | 2.91 |
| 11.9527 | 19.02 | 26.8483 | 2.62 |
| 12.3666 | 31.58 | 27.289 | 5.9 |
| 12.991 | 14.84 | 27.7244 | 1.71 |
| 13.6135 | 1.56 | 27.9638 | 2.87 |
| 15.0665 | 2.15 | 28.2507 | 7.25 |
| 15.7057 | 28.93 | 28.8163 | 9.58 |
| 15.8672 | 6.45 | 29.4594 | 2.8 |
| 16.9685 | 31.14 | 29.8907 | 5.98 |
| 17.1242 | 25.42 | 31.0021 | 2.36 |
| 17.2278 | 100 | 31.7155 | 2.65 |
| 17.9791 | 9.49 | 32.1902 | 1.48 |
| 18.882 | 54.69 | 32.6338 | 1.65 |
| 19.134 | 20.78 | 33.443 | 2.89 |
| 19.5062 | 3.45 | 33.9164 | 2.14 |
| 19.8393 | 4.83 | 34.1782 | 4.34 |
| 20.3703 | 34.09 | 34.8012 | 4.15 |
| 20.6363 | 23.29 | 35.1149 | 3.71 |
| 20.858 | 62.9 | 35.854 | 2.87 |
| 21.7795 | 2.34 | 36.3536 | 2.76 |
| 22.1284 | 7.66 | 37.2366 | 2.74 |
| 22.5189 | 3.45 | 38.0423 | 1.9 |
| 22.983 | 6.78 | 38.8331 | 3.04 |
| 23.5185 | 47.73 | | |
| 24.0099 | 2.41 | | |

Compound I THF solvate Form H, DSC & TGA Thermogram

Compound I Form J, XRPD Diffractogram

FIG. 17

Compound I Form J, XRPD Peak Table

| Angle/ °2θ | Rel. Int. [%] | Angle/ °2θ | Rel. Int. [%] |
|---:|---:|---:|---:|
| 5.9983 | 24.73 | 21.3847 | 3.86 |
| 8.9348 | 3.34 | 21.9291 | 20.93 |
| 9.771 | 6.57 | 22.3163 | 8.6 |
| 10.1779 | 2.31 | 22.6476 | 5.72 |
| 11.7769 | 2.04 | 23.2174 | 4.41 |
| 13.0994 | 28.01 | 23.6222 | 2.68 |
| 13.6539 | 16.78 | 23.9781 | 7.47 |
| 13.9044 | 4.17 | 24.6701 | 4.09 |
| 14.4123 | 1.73 | 25.2853 | 6.76 |
| 14.7806 | 1.76 | 26.0389 | 2.22 |
| 15.6203 | 19.77 | 26.6487 | 5.51 |
| 16.218 | 2.35 | 27.4251 | 10.89 |
| 16.6847 | 9.89 | 28.0026 | 5.3 |
| 17.0445 | 8.17 | 28.7636 | 4.29 |
| 17.272 | 100 | 29.1083 | 3.55 |
| 17.7455 | 1.79 | 29.6541 | 2.5 |
| 18.0542 | 13.4 | 30.1576 | 2.33 |
| 18.3253 | 18.88 | 30.8903 | 4.94 |
| 18.8187 | 23.87 | 32.8973 | 2.06 |
| 19.0841 | 17.42 | 35.2322 | 1.75 |
| 19.8242 | 46.18 | 35.9291 | 3.44 |
| 20.0847 | 81.02 | 36.7109 | 2.34 |
| 20.4723 | 5.43 | 39.1978 | 4.88 |
| 20.9422 | 5.38 | | |

Compound I Form J, DSC Thermogram

Compound I AcOH solvate Form K, XRPD Diffractogram

FIG. 20

Compound I AcOH solvate Form K, XRPD Peak Table

| Angle/ ° 2θ | Rel. Int. [%] | Angle/ ° 2θ | Rel. Int. [%] |
|---|---|---|---|
| 7.2844 | 14.87 | 23.9649 | 29.34 |
| 8.3842 | 30.59 | 24.1475 | 32.39 |
| 10.7841 | 26.41 | 25.0082 | 2.86 |
| 11.0485 | 21.09 | 25.2471 | 11.93 |
| 12.9607 | 16 | 25.552 | 10.44 |
| 14.4412 | 5.57 | 26.1599 | 19.41 |
| 14.8829 | 9.98 | 26.5591 | 7.56 |
| 15.1971 | 21.84 | 26.9464 | 49.94 |
| 15.978 | 62.58 | 27.7318 | 10.56 |
| 16.653 | 29.46 | 28.7786 | 3.71 |
| 16.8288 | 92.13 | 29.0797 | 29.67 |
| 18.5435 | 10.35 | 29.4257 | 7.65 |
| 18.9805 | 16.82 | 30.0352 | 16.64 |
| 19.1035 | 34.85 | 31.076 | 4.75 |
| 19.2515 | 15.46 | 31.7403 | 7.05 |
| 19.4353 | 100 | 32.16 | 5.09 |
| 19.8508 | 19.81 | 33.7048 | 10.57 |
| 20.306 | 32.83 | 34.5729 | 4.03 |
| 21.0342 | 9.8 | 35.2096 | 5.6 |
| 21.6105 | 5.61 | 35.524 | 6.27 |
| 21.9875 | 34.95 | 35.8015 | 4.27 |
| 22.2697 | 80.11 | 36.879 | 3.47 |
| 23.1425 | 11.44 | 38.5404 | 8.25 |
| 23.6221 | 35.03 | | |

Compound I AcOH solvate Form K, DSC & TGA Thermogram

FIG. 23

Compound I Form L, XRPD Peak Table

| Angle/ ° 2θ | Rel. Int. [%] |
|---|---|
| 9.8106 | 2.45 |
| 10.5892 | 3.99 |
| 11.6928 | 9.14 |
| 13.0741 | 12.89 |
| 13.6496 | 20.32 |
| 14.5521 | 36.25 |
| 15.5056 | 51.44 |
| 16.5659 | 1.76 |
| 17.2365 | 18.85 |
| 18.559 | 22.96 |
| 19.3655 | 100 |
| 19.7464 | 78.33 |
| 20.5913 | 20.2 |
| 21.336 | 8.68 |
| 21.6661 | 10.59 |
| 22.2146 | 32.2 |
| 23.1876 | 10.94 |
| 23.55 | 5.66 |

| Angle/ ° 2θ | Rel. Int. [%] |
|---|---|
| 24.5218 | 19.3 |
| 25.1419 | 7.78 |
| 26.0947 | 16.11 |
| 26.7205 | 4.83 |
| 27.4813 | 16.22 |
| 27.9842 | 5.63 |
| 28.5897 | 10.21 |
| 29.4212 | 4.57 |
| 30.7553 | 4.97 |
| 31.7439 | 3.36 |
| 33.0304 | 3.22 |
| 35.3031 | 5.77 |
| 36.3914 | 4.03 |
| 37.2898 | 3.06 |
| 38.4567 | 1.8 |
| 39.4205 | 1.79 |

FIG. 26

Compound I Dioxane solvate Form M, XRPD Peak Table

| Angle/ °2θ | Rel. Int. [%] | Angle/ °2θ | Rel. Int. [%] |
|---|---|---|---|
| 4.3768 | 0.3 | 23.7233 | 3.85 |
| 5.4428 | 4.06 | 23.9565 | 9.36 |
| 9.7107 | 0.76 | 24.3708 | 6.27 |
| 9.7107 | 0.76 | 24.7858 | 1.3 |
| 10.6812 | 28.88 | 25.0976 | 14.39 |
| 11.1911 | 4.27 | 25.4686 | 5.89 |
| 12.4423 | 5.68 | 25.7606 | 2.78 |
| 13.9537 | 6.96 | 26.3062 | 5.79 |
| 14.4796 | 13.61 | 26.8719 | 46.91 |
| 15.3224 | 60.93 | 26.9399 | 23.45 |
| 16.2019 | 21.25 | 27.586 | 1.55 |
| 17.511 | 65.93 | 28.145 | 2.22 |
| 18.1249 | 6.49 | 28.6619 | 23.92 |
| 18.7947 | 20.21 | 29.4561 | 10.59 |
| 19.1367 | 10.44 | 29.913 | 1.22 |
| 19.547 | 55.66 | 30.173 | 1.66 |
| 19.8038 | 38.39 | 31.0216 | 7.13 |
| 20.0852 | 48.14 | 32.5 | 1.9 |
| 20.3878 | 26.22 | 32.825 | 1.75 |
| 20.7491 | 100 | 33.228 | 1.72 |
| 21.4909 | 27.97 | 33.748 | 1.37 |
| 21.9821 | 7.23 | 34.1154 | 4.37 |
| 22.0374 | 3.61 | 35.6514 | 6.86 |
| 22.296 | 14.48 | 37.3788 | 4.45 |
| 22.5466 | 12.02 | 38.0456 | 10.11 |
| 22.8945 | 5.19 | | |
| 23.6637 | 7.7 | | |

Compound I Dioxane solvate Form M, DSC & TGA Thermogram

FIG. 29

Compound I Acetone solvate Form Q, XRPD Peak Table

| Angle/ ° 2θ | Rel. Int. [%] |
|---|---|
| 7.8329 | 37.48 |
| 8.4759 | 7.31 |
| 9.9559 | 16.34 |
| 11.0463 | 42.51 |
| 11.7523 | 16.56 |
| 12.0378 | 31.63 |
| 12.8498 | 36.46 |
| 13.3552 | 5.58 |
| 14.8984 | 7.72 |
| 15.8642 | 62.13 |
| 17.0046 | 100 |
| 17.2129 | 71.77 |
| 17.4893 | 60.55 |
| 18.5229 | 7.35 |
| 18.8435 | 95.81 |
| 19.2667 | 27.66 |
| 19.623 | 3.3 |
| 20.0908 | 32.78 |
| 20.3035 | 49.16 |
| 20.5872 | 96.31 |
| 21.5894 | 3.83 |
| 22.0953 | 18.89 |
| 22.5194 | 11.6 |
| 23.0467 | 10.91 |
| 23.9547 | 39.11 |
| 24.429 | 4.27 |
| 25.1992 | 32.72 |
| 25.4453 | 84.4 |
| 25.8732 | 10.29 |
| 26.1614 | 5.74 |
| 26.417 | 11.35 |
| 26.7543 | 18.01 |
| 27.2115 | 10.89 |
| 27.928 | 16.25 |
| 29.042 | 1.26 |
| 29.354 | 1.21 |
| 29.9009 | 5.87 |
| 30.2304 | 10.01 |
| 31.1151 | 13.03 |
| 31.668 | 1.88 |
| 32.1411 | 5.89 |
| 33.3745 | 6 |
| 34.1675 | 4.9 |
| 34.6411 | 3.57 |
| 34.9543 | 4.1 |
| 35.5966 | 13.21 |
| 36.3053 | 6.66 |
| 37.0444 | 3.96 |
| 37.5811 | 6.1 |
| 38.1735 | 8.78 |
| 39.2091 | 6.15 |

Compound I MeOH solvate Form R, XRPD Diffractogram

FIG. 31

Compound I MeOH solvate Form R, XRPD Peak Table

| Angle/ °2θ | Rel. Int. [%] | Angle/ °2θ | Rel. Int. [%] |
|---|---|---|---|
| 6.8042 | 17.05 | 26.182 | 1.1 |
| 10.137 | 2.52 | 26.3985 | 13.82 |
| 10.556 | 31.49 | 26.663 | 2.86 |
| 11.7745 | 9.2 | 26.7305 | 1.43 |
| 12.6001 | 12.18 | 26.9225 | 3.57 |
| 13.4081 | 7.18 | 26.9907 | 1.78 |
| 13.6357 | 3.96 | 27.0785 | 15.86 |
| 13.8352 | 2.11 | 27.1471 | 7.93 |
| 14.6403 | 52.92 | 27.417 | 0.61 |
| 15.147 | 2.9 | 27.872 | 1.07 |
| 17.017 | 0.76 | 28.158 | 0.75 |
| 17.6882 | 15.48 | 28.7251 | 1.78 |
| 18.1622 | 5.83 | 29.2967 | 1.56 |
| 18.6884 | 2.39 | 29.51 | 1 |
| 19.4251 | 4.06 | 30.1559 | 4.84 |
| 19.9768 | 11.36 | 30.9471 | 6.02 |
| 20.3535 | 60.37 | 31.026 | 3.01 |
| 20.4362 | 100 | 31.3272 | 2.02 |
| 21.9519 | 8.99 | 32.0929 | 1.98 |
| 22.231 | 8.86 | 32.6465 | 2.59 |
| 22.3559 | 5.19 | 33.777 | 1.27 |
| 22.4122 | 2.59 | 34.216 | 0.54 |
| 22.7415 | 1.89 | 34.5429 | 2.3 |
| 22.9526 | 4.02 | 34.775 | 1.02 |
| 23.3039 | 28.85 | 35.4206 | 1.74 |
| 23.6956 | 1.42 | 35.7264 | 4.66 |
| 24.115 | 1.07 | 36.4239 | 3.67 |
| 24.3269 | 7.98 | 37.9154 | 2.16 |
| 25.0391 | 2.48 | 39.2971 | 5.17 |
| 25.3627 | 1.76 | | |
| 25.9253 | 3.45 | | |

Compound I MeOH solvate Form R, DSC & TGA Thermogram

POLYMORPHS OF PYRIMIDINE CYCLOHEXYL GLUCOCORTICOID RECEPTOR MODULATORS

CROSS-REFERENCE TO RELATED APPLICATIONS

This application is a continuation of U.S. application Ser. No. 17/308,380, filed May 5, 2021, which claims priority to U.S. Provisional Application Nos. 63/128,534, filed Dec. 21, 2020, and 63/020,916, filed May 6, 2020, each of which is incorporated herein in its entirety for all purposes.

BACKGROUND

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR, also known as the type II GR). A mineralocorticoid receptor (MR), also known as a type I glucocorticoid receptor (GR I), may be activated by aldosterone in humans. Compositions including modulators of one or both of GR and MR may be used to treat a variety of diseases and disorders. In man, GR may be present in two forms: a ligand-binding GR-alpha of 777 amino acids; and, a GR-beta isoform which lacks the 50 carboxy terminal residues. Since these residues include the ligand binding domain, GR-beta is unable to bind the natural ligand, and is constitutively localized in the nucleus.

The biologic effects of cortisol, including those caused by hypercortisolemia, can be modulated at the GR level using receptor modulators, such as agonists, partial agonists and antagonists. Several different classes of agents are able to inhibit the physiologic effects of GR-agonist binding. These antagonists include compositions which, by binding to GR, inhibit the ability of an agonist to effectively bind to and/or activate the GR. One such known GR antagonist, mifepristone, has been found to be an effective anti-glucocorticoid agent in humans (Bertagna (1984) J. Clin. Endocrinol. Metab. 59:25). Mifepristone binds to the GR with high affinity, with a dissociation constant (Kd) of $10^{-9}$ M (Cadepond (1997) Annu. Rev. Med. 48:129).

In addition to cortisol, the biological effects of other steroids can be modulated at the GR level using receptor modulators, such as agonists, partial agonists and antagonists. When administered to subjects in need thereof, steroids can provide both intended therapeutic effects as well as negative side effects.

Hepatic steatosis, also referred to as fatty liver disease, is a cellular pathology that manifests in the intracellular accumulation of triglycerides and lipids by hepatocytes. Hepatic steatosis is a prevalent liver condition that may arise from a number of etiologies. Such liver disorders include fatty liver disease, nonalcoholic fatty liver disease (NAFLD), nonalcoholic steatohepatitis (NASH), alcohol-induced fatty liver disease (AFLD), drug- or alcohol-related liver diseases, viral diseases, immune-mediated liver diseases, metabolic liver diseases, and complications associated with hepatic insufficiency and/or liver transplantation. Nonalcoholic fatty liver disease is a common hepatic disorder with histological features similar to those of alcohol-induced fatty liver disease, in individuals who consume little or no alcohol. Effective treatments for hepatic steatosis remain insufficient. To date, no therapeutic drug treatment is established for such patients. Thus, there is a need for novel therapeutic options for managing hepatic steatosis.

Administration of antipsychotic medication is an important treatment for many psychiatric disorders, and provides significant relief to the nearly 20 million patients suffering from such disorders. Unfortunately, antipsychotic medications such as olanzapine, risperidine, clozapine, quetiapine, sertindole, and other such medications, often lead to significant weight gain as well as alleviating psychotic symptoms. Numerous reports indicate that about 40-80% of patients who receive antipsychotic medications for long periods of time experience substantial weight gain, ultimately exceeding their ideal body weight by 20% or more (see, e.g., Umbricht et al., J Clin. Psychiatry 55 (Suppl. B):157-160, 1994; Baptista, Acta Psychiatr. Scand. 100:3-16, 1999). Such weight gain increases the risk of many serious health problems associated with obesity, such as cardiovascular disease, stroke, hypertension, type II diabetes, and certain types of cancer. In addition, unwanted weight gain is one of the most common reasons for a patient's non-compliance with the administration of antipsychotic medications.

Over-use of substances such as alcohol, drugs of abuse, cigarettes, and others is a serious problem which often leads to health problems, disease and possibly death. In addition to the medical problems associated with such over-use, other problems occur, including psychological problems, problems in the families of those who over-use such substances, problems in the workplace, and problems in society at large.

The compounds of U.S. Pat. No. 8,685,973 have demonstrated utility for treating one or more of these conditions. What is needed are new forms of these compositions. Surprisingly, the present invention meets these and other needs.

BRIEF SUMMARY OF THE INVENTION

In one embodiment, the present invention provides a crystalline form of (E)-6-(4-Phenylcyclohexyl)-5-(3-trifluoromethylbenzyl)-1H-pyrimidine-2,4-dione (Compound I):

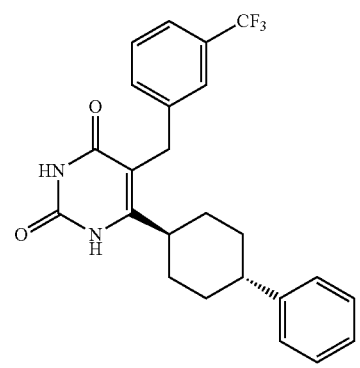 [SMILES: O=c1[nH]c(=O)c(Cc2cccc(C(F)(F)F)c2)c([C@H]2CC[C@H](c3ccccc3)CC2)[nH]1]

selected from the group consisting of:
anhydrate Form B of (E)-6-(4-Phenylcyclohexyl)-5-(3-trifluoromethylbenzyl)-1H-pyrimidine-2,4-dione (Compound I);
anhydrate Form A of (E)-6-(4-Phenylcyclohexyl)-5-(3-trifluoromethylbenzyl)-1H-pyrimidine-2,4-dione (Compound I);

anhydrate Form C of (E)-6-(4-Phenylcyclohexyl)-5-(3-trifluoromethylbenzyl)-1H-pyrimidine-2,4-dione (Compound I);

anhydrate Form F of (E)-6-(4-Phenylcyclohexyl)-5-(3-trifluoromethylbenzyl)-1H-pyrimidine-2,4-dione (Compound I);

anhydrate Form J of (E)-6-(4-Phenylcyclohexyl)-5-(3-trifluoromethylbenzyl)-1H-pyrimidine-2,4-dione (Compound I);

anhydrate Form L of (E)-6-(4-Phenylcyclohexyl)-5-(3-trifluoromethylbenzyl)-1H-pyrimidine-2,4-dione (Compound I);

THF solvate Form H of (E)-6-(4-Phenylcyclohexyl)-5-(3-trifluoromethylbenzyl)-1H-pyrimidine-2,4-dione (Compound I, THF solvate);

AcOH solvate Form K of (E)-6-(4-Phenylcyclohexyl)-5-(3-trifluoromethylbenzyl)-1H-pyrimidine-2,4-dione (Compound I, AcOH solvate);

dioxane solvate Form M of (E)-6-(4-Phenylcyclohexyl)-5-(3-trifluoromethylbenzyl)-1H-pyrimidine-2,4-dione (Compound I, dioxane solvate);

acetone solvate Form Q of (E)-6-(4-Phenylcyclohexyl)-5-(3-trifluoromethylbenzyl)-1H-pyrimidine-2,4-dione (Compound I, acetone solvate); and methanol solvate Form R of (E)-6-(4-Phenylcyclohexyl)-5-(3-trifluoromethylbenzyl)-1H-pyrimidine-2,4-dione (Compound I, methanol solvate).

In another embodiment, the present invention provides a crystalline anhydrate form of (E)-6-(4-Phenylcyclohexyl)-5-(3-trifluoromethylbenzyl)-1H-pyrimidine-2,4-dione (Compound I):

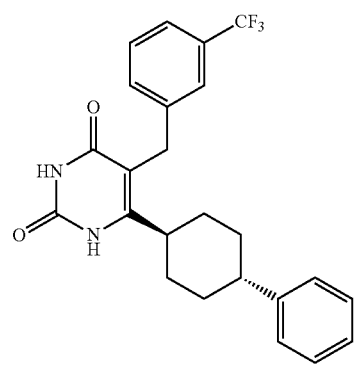 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 16.3, 17.1, 18.7, 19.9, 22.1, or 22.3° 2θ±0.2° 2θ, Form A.

In another embodiment, the present invention provides a crystalline anhydrate form of (E)-6-(4-Phenylcyclohexyl)-5-(3-trifluoromethylbenzyl)-1H-pyrimidine-2,4-dione (Compound I):

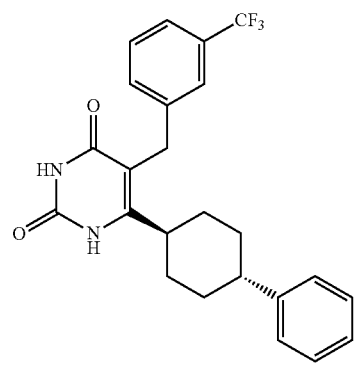 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 17.3, 17.9, 18.3, 18.4, 21.3, or 21.8° 2θ±0.2° 2θ, Form C.

In another embodiment, the present invention provides a crystalline anhydrate form of (E)-6-(4-Phenylcyclohexyl)-5-(3-trifluoromethylbenzyl)-1H-pyrimidine-2,4-dione (Compound I):

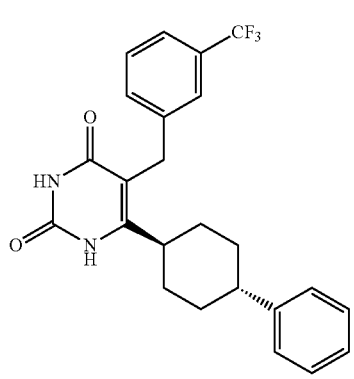 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 16.7, 17.0, 17.3, 17.7, 19.0, 19.6, or 23.6° 2θ±0.2° 2θ, Form B.

In another embodiment, the present invention provides a crystalline anhydrate form of (E)-6-(4-Phenylcyclohexyl)-5-(3-trifluoromethylbenzyl)-1H-pyrimidine-2,4-dione (Compound I):

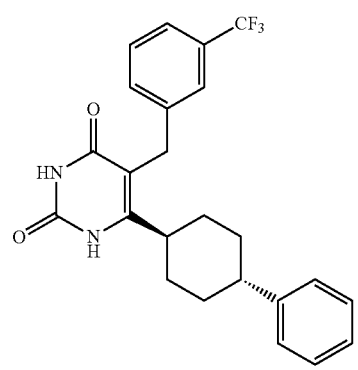 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 15.9, 16.4, 16.8, 17.3, 19.0, 21.1, or 25.8° 2θ±0.2° 2θ, Form F In another embodiment, the present invention provides a crystalline anhydrate form of (E)-6-(4-Phenylcyclohexyl)-5-(3-trifluoromethylbenzyl)-1H-pyrimidine-2,4-dione (Compound I):

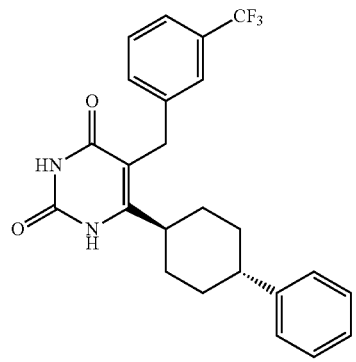 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 6.0, 13.1, 17.3, 18.8, 19.8, 20.1, or 21.9° 2θ±0.2° 2θ, Form J.

In another embodiment, the present invention provides a crystalline anhydrate form of (E)-6-(4-Phenylcyclohexyl)-5-(3-trifluoromethylbenzyl)-1H-pyrimidine-2,4-dione (Compound I):

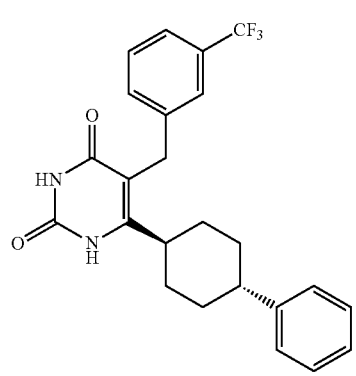 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 14.6, 15.5, 19.4, 19.7, or 22.2° 2θ±0.2° 2θ, Form L.

In another embodiment, the present invention provides a crystalline form of (E)-6-(4-Phenylcyclohexyl)-5-(3-trifluoromethylbenzyl)-1H-pyrimidine-2,4-dione THF solvate (Compound I, THF solvate):

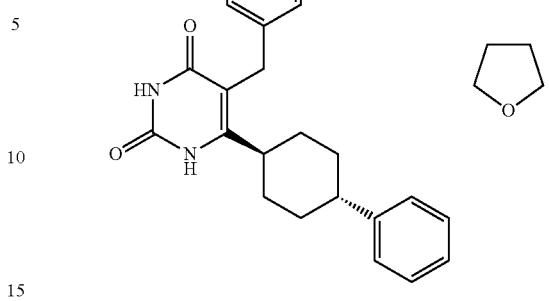

characterized by an X-ray powder diffraction (XRPD) pattern comprising three or more peaks at 17.2, 18.9, 20.9, 23.5, 25.0, or 25.6° 2θ±0.2° 2θ, THF solvate Form H In another embodiment, the present invention provides a crystalline form of (E)-6-(4-Phenylcyclohexyl)-5-(3-trifluoromethylbenzyl)-1H-pyrimidine-2,4-dione acetic acid (Compound I, acetic acid solvate):

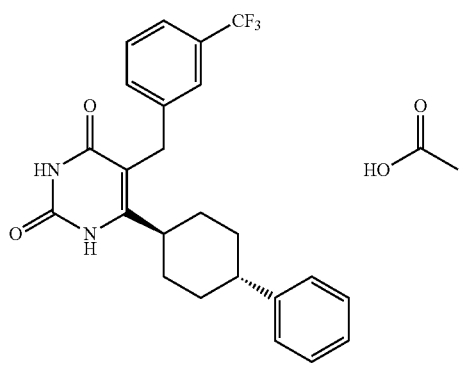

characterized by an X-ray powder diffraction (XRPD) pattern comprising three or more peaks at 16.0, 16.8, 19.4, 22.3, 23.6, or 26.9° 2θ±0.2° 2θ, AcOH solvate Form K.

In another embodiment, the present invention provides a crystalline form of (E) (4-Phenylcyclohexyl)-5-(3-trifluoromethylbenzyl)-1H-pyrimidine-2,4-dione dioxane (Compound I, dioxane solvate):

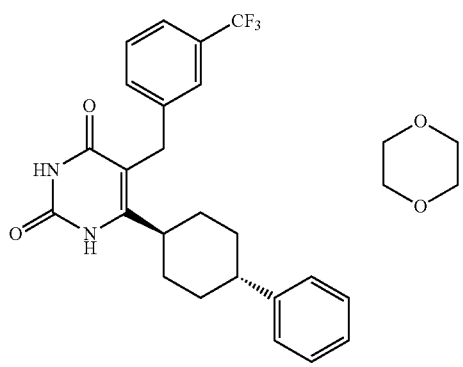 [SMILES: O=c1[nH]c(=O)c(Cc2cccc(C(F)(F)F)c2)c([C@H]2CC[C@H](c3ccccc3)CC2)[nH]1 ; C1COCCO1]

characterized by an X-ray powder diffraction (XRPD) pattern comprising three or more peaks at 15.3, 17.5, 19.5, 20.1, 20.7, or 26.8° 2θ±0.2° 2θ, Dioxane solvate Form M.

In another embodiment, the present invention provides a crystalline form of (E)-6-(4-Phenylcyclohexyl)-5-(3-trifluoromethylbenzyl)-1H-pyrimidine-2,4-dione acetone (Compound I, acetone solvate):

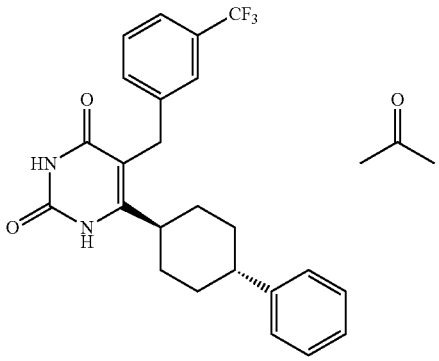

characterized by an X-ray powder diffraction (XRPD) pattern comprising three or more peaks at 15.9, 17.0, 17.2, 17.5, 18.8, 20.6, or 25.4° 2θ±0.2° 2θ, Acetone solvate Form Q.

In another embodiment, the present invention provides a crystalline form of (E)-6-(4-Phenylcyclohexyl)-5-(3-trifluoromethylbenzyl)-1H-pyrimidine-2,4-dione methanol (Compound I, methanol solvate):

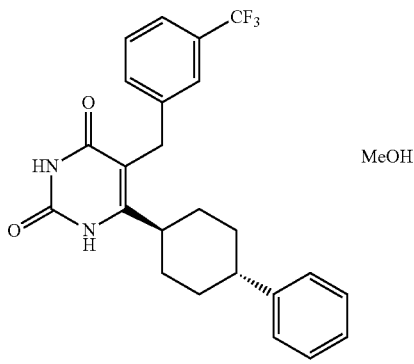 [SMILES: "MeOH" ; O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 10.6, 14.6, 20.3, 20.4, or 23.3° 2θ±0.2° 2θ, MeOH solvate Form R.

In another embodiment, the present invention provides a pharmaceutical composition comprising a crystalline Compound I, and one or more pharmaceutically acceptable excipients.

In another embodiment, the present invention provides a method of treating a disorder or condition through modulating a glucocorticoid receptor, comprising administering to a subject in need of such treatment, a therapeutically effective amount of a crystalline Compound I or a pharmaceutical composition of the crystalline Compound I, thereby treating the disorder or condition.

In another embodiment, the present invention provides a method of treating a disorder or condition through antagonizing a glucocorticoid receptor, comprising administering to a subject in need of such treatment, a therapeutically effective amount of a crystalline Compound I or a pharmaceutical composition of the crystalline Compound I, thereby treating the disorder or condition.

In another embodiment, the present invention provides a method of treating fatty liver disease, comprising administering to a subject in need thereof, a therapeutically effective amount of a crystalline Compound I, or a pharmaceutical composition of the crystalline Compound I, thereby treating fatty liver disease.

In another embodiment, the present invention provides a method of treating antipsychotic induced weight gain, comprising administering to a subject in need thereof, a therapeutically effective amount of a crystalline Compound I or a pharmaceutical composition of the crystalline Compound I, thereby treating antipsychotic induced weight gain.

BRIEF DESCRIPTION OF THE DRAWINGS

FIG. 2 shows the XRPD peaks for Compound I Form B.
FIG. 5 shows the XRPD peaks for Compound I Form A.
FIG. 8 shows the XRPD peaks for Compound I Form C.
FIG. 11 shows the XRPD peaks for Compound I Form F.
FIG. 14 shows the XRPD peaks for Compound I THF solvate Form H.
FIG. 17 shows the XRPD peaks for Compound I Form J.
FIG. 20 shows the XRPD peaks for Compound I AcOH solvate Form K.
FIG. 23 shows the XRPD peaks for Compound I Form L.
FIG. 26 shows the XRPD peaks for Compound I Dioxane solvate Form M.
FIG. 29 shows the XRPD peaks for Compound I Acetone solvate Form Q.
FIG. 31 shows the XRPD peaks for Compound I MeOH solvate Form R.

DETAILED DESCRIPTION OF THE INVENTION

I. General

Figure 1:
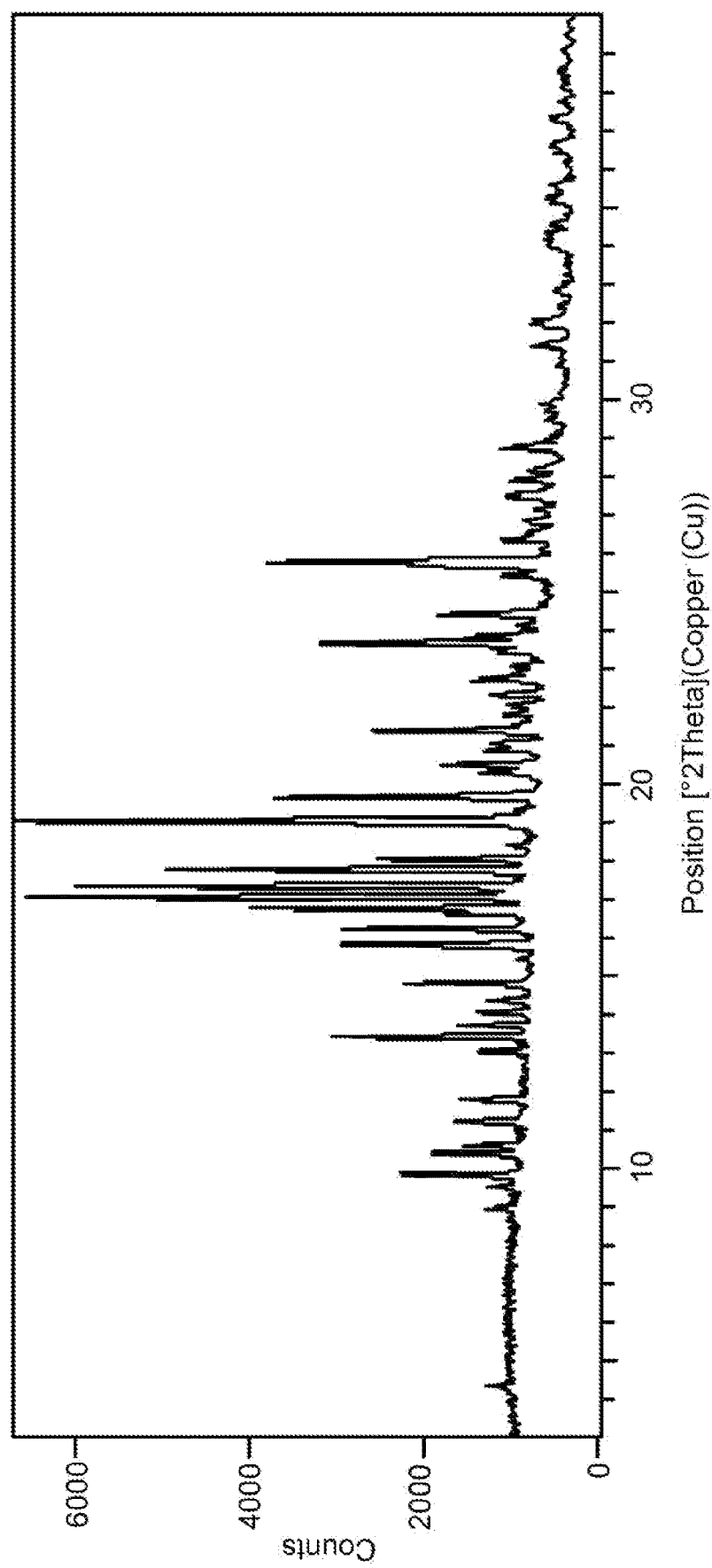
FIG. 1 shows the XRPD pattern for Compound I Form B.

Disclosed herein are crystalline forms of (E)-6-(4-Phenylcyclohexyl)-5-(3-trifluoromethylbenzyl)-1H-pyrimidine-2,4-dione (Compound I):

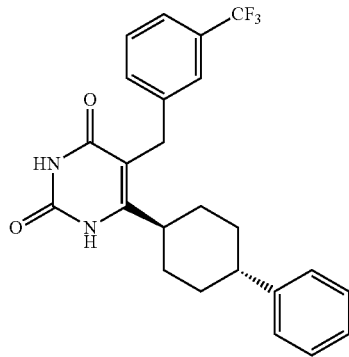 [SMILES: O=c1[nH]c(=O)c(Cc2cccc(C(F)(F)F)c2)c([C@H]2CC[C@H](c3ccccc3)CC2)[nH]1]

including anhydrate forms thereof. Compound I can adopt a variety of crystalline forms, including, but not limited to, crystalline Compound I Form B. Compound I can form a mixture of two or more crystalline forms, or form a single crystalline form substantially free of other crystalline forms.

II. Definitions

"About" refers to plus or minus 5% of the specified value unless otherwise indicated.

"Substantially as shown in" refers to any crystal or solid form of (E)-6-(4-Phenylcyclohexyl)-5-(3-trifluoromethylbenzyl)-1H-pyrimidine-2,4-dione (Compound I) characterized by the graphical data in the identified figure, optionally having one or more of small variations, e.g., one or more variations described below or known to one of skill in the art. Such data may include, without limitation, powder X-ray diffractograms, differential scanning calorimetry curves, and thermogravimetric analysis curves, among others. As is known in the art, such graphical data may provide additional technical information to further define the crystal polymorph, amorphous solid form, or other composition. As is understood by one of skill in the art, such graphical representations of data may be subject to small variations, e.g., in peak relative intensities and peak positions due to factors such as variations in instrument response and variations in sample concentration and purity. Nonetheless, one of skill in the art will readily be capable of comparing the graphical data in the figures herein with graphical data generated for a crystal polymorph, amorphous solid form, or other composition and confirm whether the two sets of graphical data are characterizing the same material or two different materials.

"Substantially free of" refers to a crystalline or solid form of Compound I containing no significant amount of such other crystalline or solid forms of Compound I. For example, a first crystalline form can be substantially free of a second crystalline form when the first crystalline form constitutes at least about 95% by weight of the crystalline Compound I present, or at least about 96%, 97%, 98%, 99%, or at least about 99.5% by weight of the crystalline Compound I present.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier(s), diluent(s) or excipient(s) must be compatible with the other ingredients of the formulation and not deleterious to the recipient thereof.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, surfactants, coatings, sweeteners, flavors and colors. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, horse, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Glucocorticoid receptor" ("GR") refers to one of the family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

A cortisol receptor is a glucocorticoid receptor (GR), specifically the type II GR, which specifically binds cortisol and/or cortisol analogs such as dexamethasone (See, e.g., Turner & Muller, J. Mol. Endocrinol. Oct. 1, 2005 35 283-292).

"Mineralocorticoid receptor" (MR) refers to a type I glucocorticoid receptor (GR I), which is activated by aldosterone in humans.

"Glucocorticoid receptor modulator" (GRM) refers to any compound which modulates any biological response associated with the binding of a glucocorticoid receptor to an agonist. As used herein, with respect to a GRM, the glucocorticoid receptor may be GR, or both. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, inhibits the agonist-induced increase in the activity of tyrosine aminotransferase (TAT) in HepG2 cells. TAT activity can be measured as outlined in the literature by A. Ali et al., J. Med. Chem., 2004, 47, 2441-2452.

"Glucocorticoid receptor antagonist" (GRA) refers to any compound which inhibits any biological response associated with the binding of a glucocorticoid receptor to an agonist. As used herein, with respect to a GRA, the glucocorticoid receptor may be GR, or both. Accordingly, GR antagonists can be identified by measuring the ability of a compound to inhibit the effect of dexamethasone. TAT activity can be measured as outlined in the literature by A. Ali et al., J. Med. Chem., 2004, 47, 2441-2452. An inhibitor is a compound with an $IC_{50}$ (half maximal inhibition concentration) of less than 10 micromolar. See Example 1 of U.S. Pat. No. 8,685,973, the entire contents of which is hereby incorporated by reference in its entirety.

"Modulate" and "modulating" are used in accordance with its plain ordinary meaning and refer to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Modulator" refers to a composition that increases or decreases the level of a target molecule or the function of a target molecule or the physical state of the target of the molecule.

"Antagonize' and "antagonizing" refer to inhibiting the binding of an agonist at a receptor molecule or to inhibiting the signal produced by a receptor-agonist. A receptor antagonist inhibits or dampens agonist-mediated responses, such as gene expression.

"Antagonist" refers to a substance capable of detectably lowering expression or activity of a given gene or protein. The antagonist can inhibit expression or activity 10%, 20%, 30%, 40%, 50%, 60%, 70%, 80%, 90%, 100% or less in comparison to a control in the absence of the antagonist. In some embodiments, the inhibition is 1.5-fold, 2-fold, 3-fold, 4-fold, 5-fold, 10-fold, or more than the expression or activity in the absence of the antagonist.

"Inhibition", "inhibits" and "inhibitor" refer to a compound that prohibits or a method of prohibiting, a specific action or function.

"Disorder" or "condition" refers to a state of being or health status of a patient or subject capable of being treated with the glucocorticoid receptor modulator of the present invention. In some embodiments, examples of disorders or conditions include, but are not limited to, fatty liver disease, nonalcoholic fatty liver disease (NAFLD), nonalcoholic steatohepatitis (NASH), and antipsychotic-induced weight gain.

"Fatty liver disease" refers to a disease or a pathological condition caused by, at least in part, abnormal hepatic lipid deposits. Fatty liver disease includes, e.g., alcoholic fatty liver disease, nonalcoholic fatty liver disease, and acute fatty liver of pregnancy. Fatty liver disease may be, e.g., macrovesicular steatosis or microvesicular steatosis.

"Non-alcoholic fatty liver disease" ("NAFLD") refers to one of the types of fatty liver disease which occurs when fat is deposited (steatosis) in the liver due to causes other than excessive alcohol use. NAFLD is considered to cover a spectrum of disease activity. This spectrum begins as fatty accumulation in the liver (hepatic steatosis). Most people with NAFLD have few or no symptoms. Patients may complain of fatigue, malaise, and dull right-upper-quadrant abdominal discomfort. Mild jaundice may be noticed, although this is rare. More commonly NAFLD is diagnosed following abnormal liver function tests during routine blood tests. By definition, alcohol consumption of over 20 g/day (about 25 ml/day of net ethanol) excludes the condition.

"Non-alcoholic steatohepatitis" ("NASH") refers to the most extreme form of NAFLD. NAFLD can progress to become non-alcoholic steatohepatitis (NASH), a state in which steatosis is combined with inflammation and fibrosis (steatohepatitis). NASH is a progressive disease. Over a 10-year period, up to 20% of patients with NASH will develop cirrhosis of the liver, and 10% will suffer death related to liver disease.

"Substance use disorder" refers to the compulsive use of a substance despite unpleasant or harmful consequences of that use. A substance use disorder may involve impaired control (e.g., use of excessive amounts of the substance, or over longer periods of time, than was originally intended), social impairment (e.g., failure to fulfill major roles obligations at work, school, or home), risky use (e.g., recurrent use of the substance in situations in which it is physically hazardous), and pharmacological criteria (e.g., tolerance or withdrawal). A substance use disorder may have formerly been termed an "addiction" although, since the publication of the Diagnostic and Statistical Manual of Mental Disorders Fifth Edition DSM-5 (hereafter "DSM-V"), terms such as "addiction" and "addict" have been replaced for the terms "substance use disorder" (replacing "addiction") and person suffering from a substance use disorder (replacing "addict"). A person suffering from a substance use disorder may be termed as suffering from a substance use disorder related to a particular substance; prior to the publication of DSM-V, such a person may have been described as being "addicted to" that substance. For example, where a person has a substance use disorder related to a stimulant, that person may have been described as being "addicted to" that stimulant prior to the publication of DSM-V.

"Substance" as recited in phrases such as "substance use disorder related to said substance" and "substance use disorder related to the substance" refers to the substance for which a patient has a craving, or which the patient uses compulsively despite unpleasant or harmful consequences of that use. Thus, such a "substance" is the substance used by, or ingested, or otherwise administered to (including self-administration) a person who suffers from a substance use disorder related to that substance. The terms "substance of addiction", and "substance of abuse" may have formerly been used to refer such a substance, which substance may formerly have been termed an "addictive substance" (e.g., prior to the publication of DSM-V).

"Person suffering from a substance use disorder" refers to a person suffering from a substance use disorder related to a particular substance, or, in some cases, more than one particular substance. Such a "substance" may be a drug, or alcohol, or a cigarette, or other substance a person may take (ingest). For example, such a "substance" may be alcohol, a stimulant, an opioid, or other substance.

"Volumes" refers to the number of liters (L) of a solvent per kilogram (kg) of a component. For example, 15 volumes of dichloromethane refers to 15 liters per kilogram of Compound I. As dichloromethane has a density of 1.33 g/mL, 15 volumes corresponds to 20 kg of dichloromethane per 1 kg of Compound I.

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

III. Solid Forms of Compound I

The present invention results from the surprising discoveries of new solid forms of (E)-6-(4-Phenylcyclohexyl)-5-(3-trifluoromethylbenzyl)-1H-pyrimidine-2,4-dione (Compound I; see U.S. Pat. No. 8,685,973), including crystalline forms, such as crystalline anhydrate forms thereof. In some embodiments, the present invention provides a crystalline form of Compound I having the structure:

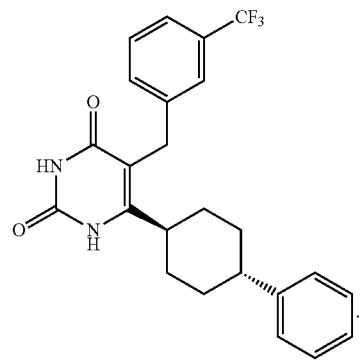 [SMILES: O=c1[nH]c(=O)c(Cc2cccc(C(F)(F)F)c2)c([C@H]2CC[C@H](c3ccccc3)CC2)[nH]1]

The compound can also be named 6-(trans-4-phenylcyclohexyl)-5-(3-(trifluoromethyl)phenyl)methyl)pyrimidine-2,4(1H,3H)-dione or 6-((1r,4r)-4-phenylcyclohexyl)-5-(3-(trifluoromethyl)benzyl)pyrimidine-2,4(1H,3H)-dione.

Compound I can adopt a variety of crystalline forms, including, but not limited to, crystalline Compound I Form B. Compound I can form a mixture of two or more crystalline forms, or form a single crystalline form substantially free of other crystalline forms of Compound I.

In some embodiments, the present invention provides a crystalline anhydrate form of the compound (E)-6-(4-Phenylcyclohexyl)-5-(3-trifluoromethylbenzyl)-1H-pyrimidine-2,4-dione (Compound I).

In some embodiments, the present invention provides a crystalline form of (E)-6-(4-Phenylcyclohexyl)-5-(3-trifluoromethylbenzyl)-1H-pyrimidine-2,4-dione (Compound I):

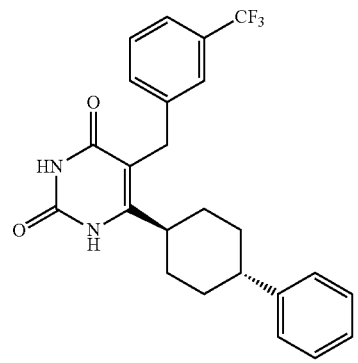 [SMILES: O=c1[nH]c(=O)c(Cc2cccc(C(F)(F)F)c2)c([C@H]2CC[C@H](c3ccccc3)CC2)[nH]1]

selected from the group consisting of:

anhydrate Form B of (E)-6-(4-Phenylcyclohexyl)-5-(3-trifluoromethylbenzyl)-1H-pyrimidine-2,4-dione (Compound I);

anhydrate Form A of (E)-6-(4-Phenylcyclohexyl)-5-(3-trifluoromethylbenzyl)-1H-pyrimidine-2,4-dione (Compound I);

anhydrate Form C of (E)-6-(4-Phenylcyclohexyl)-5-(3-trifluoromethylbenzyl)-1H-pyrimidine-2,4-dione (Compound I);

anhydrate Form F of (E)-6-(4-Phenylcyclohexyl)-5-(3-trifluoromethylbenzyl)-1H-pyrimidine-2,4-dione (Compound I);

anhydrate Form J of (E)-6-(4-Phenylcyclohexyl)-5-(3-trifluoromethylbenzyl)-1H-pyrimidine-2,4-dione (Compound I);

anhydrate Form L of (E)-6-(4-Phenylcyclohexyl)-5-(3-trifluoromethylbenzyl)-1H-pyrimidine-2,4-dione (Compound I);

THF solvate Form H of (E)-6-(4-Phenylcyclohexyl)-5-(3-trifluoromethylbenzyl)-1H-pyrimidine-2,4-dione (Compound I, THF solvate);

AcOH solvate Form K of (E)-6-(4-Phenylcyclohexyl)-5-(3-trifluoromethylbenzyl)-1H-pyrimidine-2,4-dione (Compound I, AcOH solvate);

dioxane solvate Form M of (E)-6-(4-Phenylcyclohexyl)-5-(3-trifluoromethylbenzyl)-1H-pyrimidine-2,4-dione (Compound I, dioxane solvate);

acetone solvate Form Q of (E)-6-(4-Phenylcyclohexyl)-5-(3-trifluoromethylbenzyl)-1H-pyrimidine-2,4-dione (Compound I, acetone solvate); and methanol solvate Form R of (E)-6-(4-Phenylcyclohexyl)-5-(3-trifluoromethylbenzyl)-1H-pyrimidine-2,4-dione (Compound I, methanol solvate).

Form B

In some embodiments, the present invention provides a crystalline anhydrate form of (E)-6-(4-Phenylcyclohexyl)-5-(3-trifluoromethylbenzyl)-1H-pyrimidine-2,4-dione (Compound I):

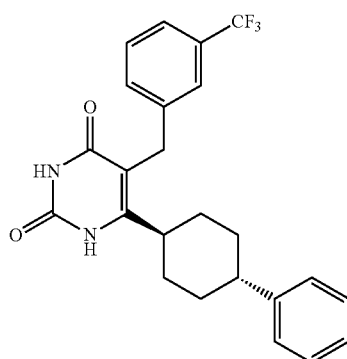

characterized by an X-ray powder diffraction (XRPD) pattern comprising three or more peaks at 16.7, 17.0, 17.3, 17.7, 19.0, 19.6, or 23.6° 2θ±0.2° 2θ, Form B.

In some embodiments, the Compound I Form B is characterized by an XRPD pattern comprising four or more peaks at 16.7, 17.0, 17.3, 17.7, 19.0, 19.6, or 23.6° 2θ±0.2° 2θ. In some embodiments, the Compound I Form B is characterized by an XRPD pattern comprising five or more peaks at 16.7, 17.0, 17.3, 17.7, 19.0, 19.6, or 23.6° 2θ±0.2° 2θ. In some embodiments, the Compound I Form B is characterized by an XRPD pattern comprising peaks at 16.7, 17.0, 17.3, 17.7, 19.0, 19.6, and 23.6° 2θ±0.2° 2θ.

In some embodiments, the Compound I Form B is characterized by an XRPD pattern further comprising one or more peaks at 9.8, 10.4, 11.2, 11.8, 13.4, 13.7, 14.8, 15.8, 16.2, 16.6, 18.0, 20.3, 20.5, 20.8, 21.0, 21.3, 22.0, 22.3, 22.7, 23.8, 24.4, 25.4, 25.6, 25.7, 26.3, 28.1, 28.7, or 37.2° 2θ±0.2° 2θ. In some embodiments, the Compound I Form B is characterized by an XRPD pattern further comprising two or more peaks at 9.8, 10.4, 11.2, 11.8, 13.4, 13.7, 14.8, 15.8, 16.2, 16.6, 18.0, 20.3, 20.5, 20.8, 21.0, 21.3, 22.0, 22.3, 22.7, 23.8, 24.4, 25.4, 25.6, 25.7, 26.3, 28.1, 28.7, or 37.2° 2θ±0.2° 2θ. In some embodiments, the Compound I Form B is characterized by an XRPD pattern further comprising three or more peaks at 9.8, 10.4, 11.2, 11.8, 13.4, 13.7, 14.8, 15.8, 16.2, 16.6, 18.0, 20.3, 20.5, 20.8, 21.0, 21.3, 22.0, 22.3, 22.7, 23.8, 24.4, 25.4, 25.6, 25.7, 26.3, 28.1, 28.7, or 37.2° 2θ±0.2° 2θ. In some embodiments, the Compound I Form B is characterized by an XRPD pattern further comprising four or more peaks at 9.8, 10.4, 11.2, 11.8, 13.4, 13.7, 14.8, 15.8, 16.2, 16.6, 18.0, 20.3, 20.5, 20.8, 21.0, 21.3, 22.0, 22.3, 22.7, 23.8, 24.4, 25.4, 25.6, 25.7, 26.3, 28.1, 28.7, or 37.2° 2θ±0.2° 2θ. In some embodiments, the Compound I Form B is characterized by an XRPD pattern comprising peaks at 9.8, 10.4, 11.2, 11.8, 13.4, 13.7, 14.8, 15.8, 16.2, 16.6, 18.0, 20.3, 20.5, 20.8, 21.0, 21.3, 22.0, 22.3, 22.7, 23.8, 24.4, 25.4, 25.6, 25.7, 26.3, 28.1, 28.7, and 37.2° 2θ±0.2° 2θ.

In some embodiments, the Compound I Form B is characterized by an XRPD pattern comprising peaks at 9.8, 10.4, 11.2, 11.8, 13.4, 13.7, 14.8, 15.8, 16.2, 16.6, 16.7, 17.0, 17.3, 17.7, 18.0, 19.0, 19.6, 20.3, 20.5, 20.8, 21.0, 21.3, 22.0, 22.3, 22.7, 23.6, 23.8, 24.4, 25.4, 25.6, 25.7, 26.3, 28.1, 28.7, and 37.2° 2θ±0.2° 2θ. In some embodiments, the Compound I Form B is characterized by an XRPD pattern substantially as shown in FIG. 1.

Figure 3:
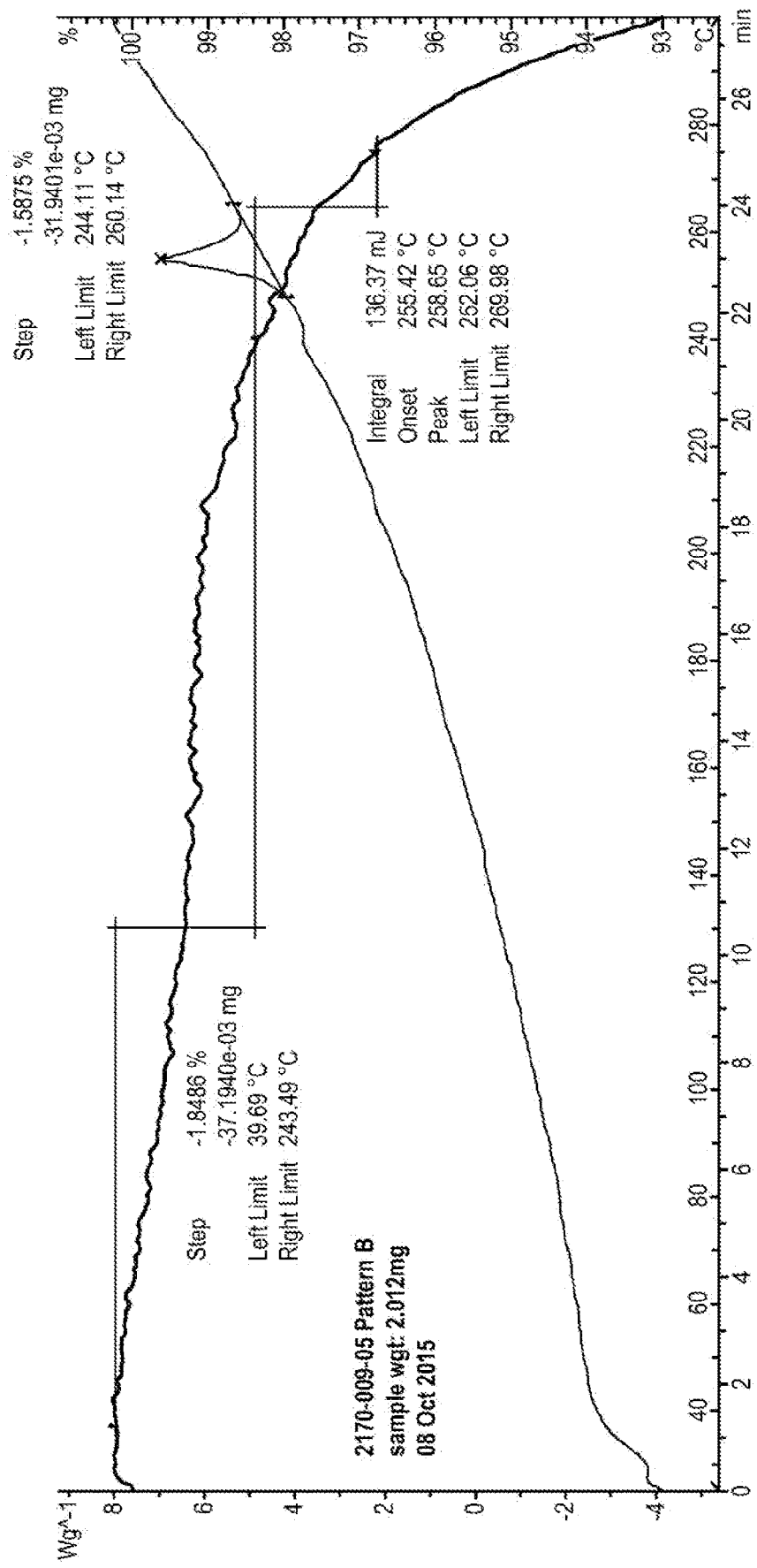
FIG. 3 shows the DSC and TGA thermogram for Compound I Form B.

In some embodiments, the Compound I Form B is characterized by a differential scanning calorimetry (DSC) thermogram having at least one endotherm with an onset of about 255° C. In some embodiments, the Compound I Form B is characterized by a DSC thermogram substantially as shown in FIG. 3.

In some embodiments, the Compound I Form B is characterized by: (a) an XRPD pattern comprising peaks at 16.7, 17.0, 17.3, 17.7, 19.0, 19.6, and 23.6° 2θ±0.2° 2θ; and (b) a differential scanning calorimetry (DSC) thermogram having an endotherm with an onset of about 255° C. In some embodiments, the Compound I Form B is characterized by: (a) an XRPD pattern substantially as shown in FIG. 1; and (b) a DSC thermogram substantially as shown in FIG. 3.

Form A

In some embodiments, the present invention provides a crystalline anhydrate form of (E)-6-(4-Phenylcyclohexyl)-5-(3-trifluoromethylbenzyl)-1H-pyrimidine-2,4-dione (Compound I):

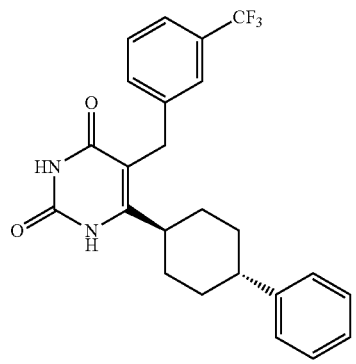 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 16.3, 17.1, 18.7, 19.9, 22.1, or 22.3° 2θ±0.2° 2θ, Form A.

In some embodiments, the Compound I Form A is characterized by an XRPD pattern comprising four or more peaks at 16.3, 17.1, 18.7, 19.9, 22.1, or 22.3° 2θ±0.2° 2θ. In some embodiments, the Compound I Form A is characterized by an XRPD pattern comprising five or more peaks at 16.3, 17.1, 18.7, 19.9, 22.1, or 22.3° 2θ±0.2° 2θ. In some embodiments, the Compound I Form A is characterized by an XRPD pattern comprising peaks at 16.3, 17.1, 18.7, 19.9, 22.1, and 22.3° 2θ±0.2° 2θ.

In some embodiments, the Compound I Form A is characterized by an XRPD pattern further comprising one or more peaks at 9.5, 14.0, 15.5, 18.5, 19.5, 21.3, or 23.3° 2θ±0.2° 2θ. In some embodiments, the Compound I Form A is characterized by an XRPD pattern further comprising two or more peaks at 9.5, 14.0, 15.5, 18.5, 19.5, 21.3, or 23.3° 2θ±0.2° 2θ. In some embodiments, the Compound I Form A is characterized by an XRPD pattern further comprising three or more peaks at 9.5, 14.0, 15.5, 18.5, 19.5, 21.3, or 23.3° 2θ±0.2° 2θ. In some embodiments, the Compound I Form A is characterized by an XRPD pattern further comprising four or more peaks at 9.5, 14.0, 15.5, 18.5, 19.5, 21.3, or 23.3° 2θ±0.2° 2θ. In some embodiments, the Compound I Form A is characterized by an XRPD pattern further comprising peaks at 9.5, 14.0, 15.5, 18.5, 19.5, 21.3, and 23.3° 2θ±0.2° 2θ.

Figure 4:
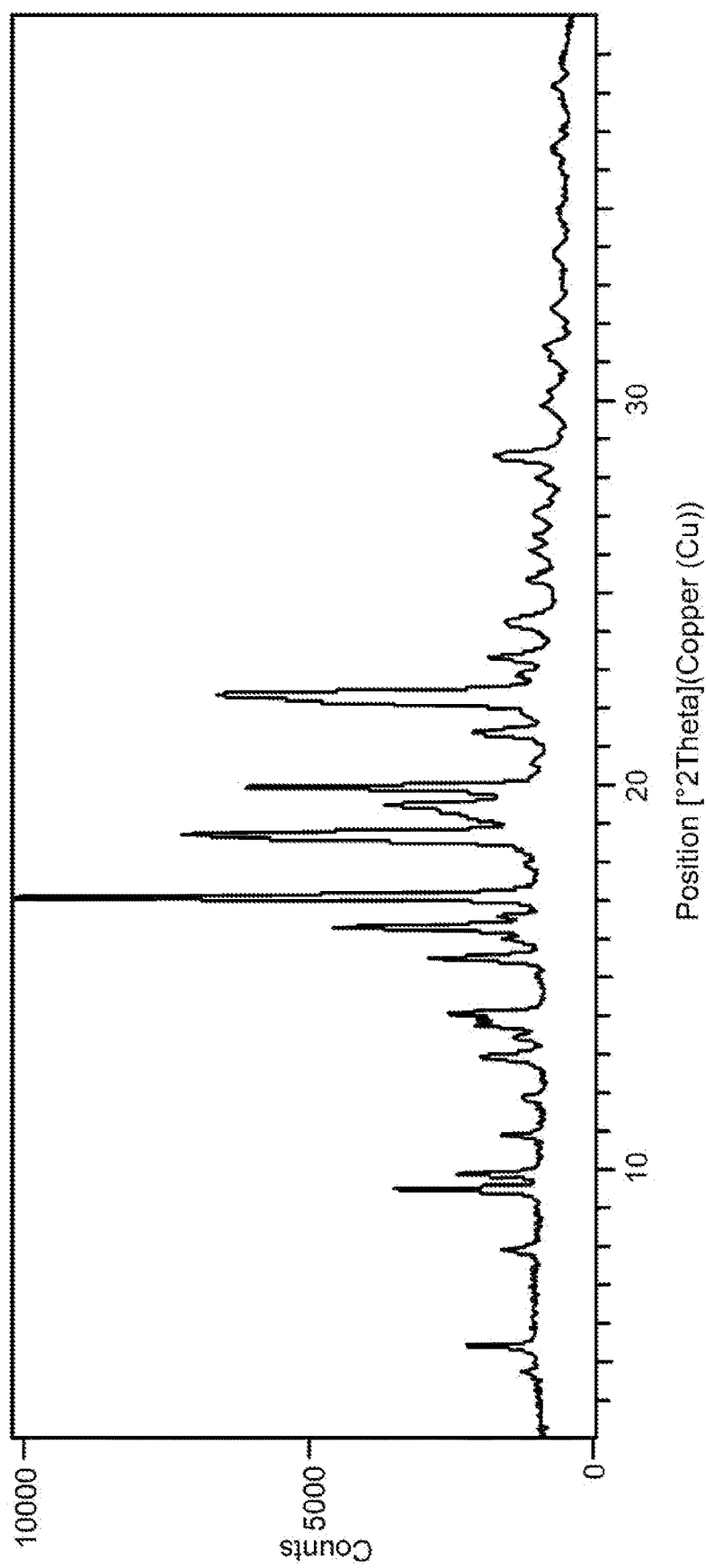
FIG. 4 shows the XRPD pattern for Compound I Form A.

In some embodiments, the Compound I Form A is characterized by an XRPD pattern comprising peaks at 9.5, 14.0, 15.5, 16.3, 17.1, 18.5, 18.7, 19.5, 19.9, 21.3, 22.1, 22.3, and 23.3° 2θ±0.2° 2θ. In some embodiments, the Compound I Formula A is characterized by an XRPD pattern substantially as shown in FIG. 4.

Figure 6:
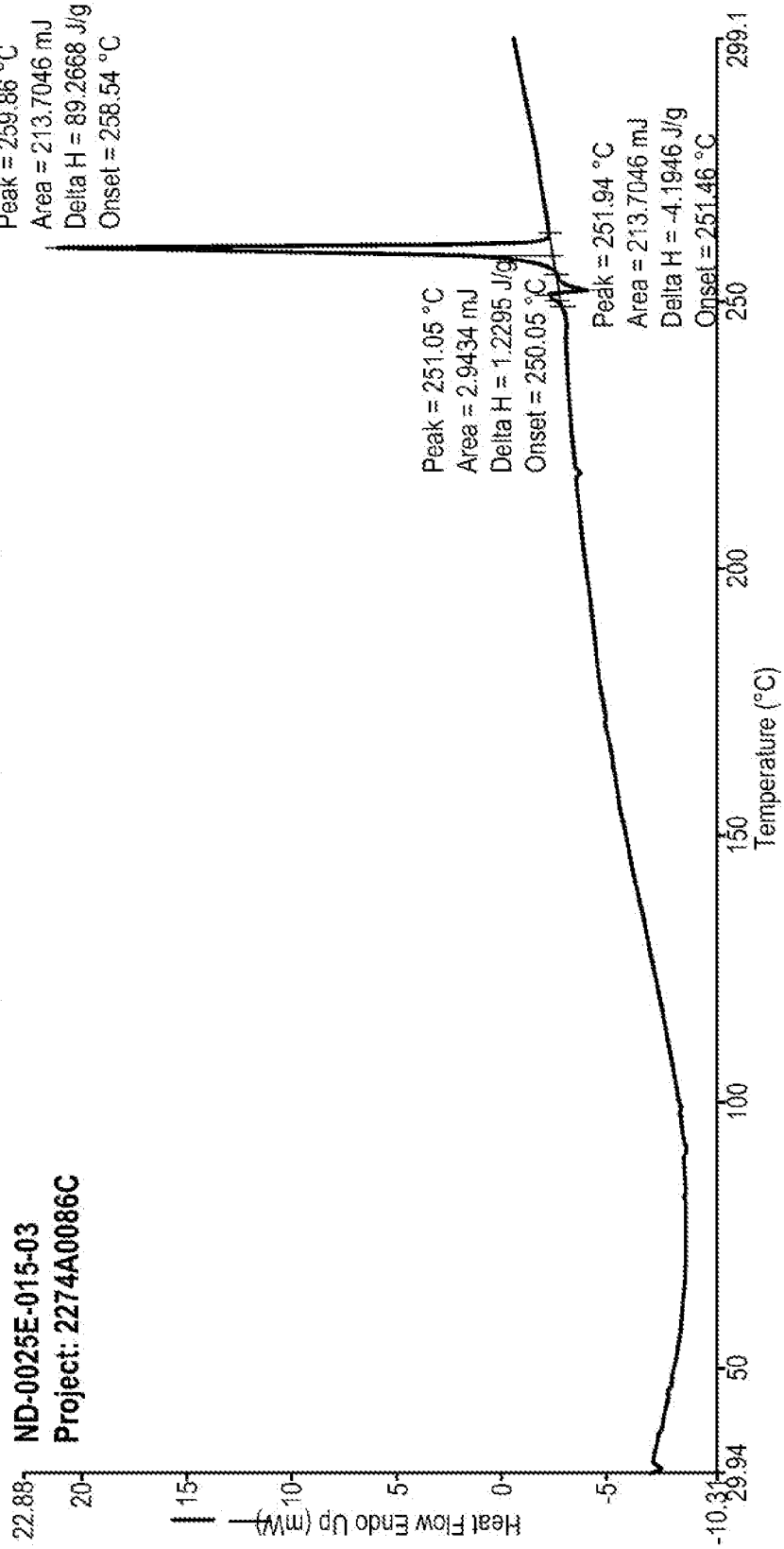
FIG. 6 shows the DSC and TGA thermogram for Compound I Form A.

In some embodiments, the Compound I Form A is characterized by a differential scanning calorimetry (DSC) thermogram having at least one endotherm with an onset of about 250, 251 or 258° C. In some embodiments, the Compound I Form A is characterized by a DSC thermogram substantially as shown in FIG. 6.

In some embodiments, the Compound I Form A is characterized by: (a) an XRPD pattern comprising peaks at 16.3, 17.1, 18.7, 19.9, 22.1, and 22.3° 2θ±0.2° 2θ; and (b) a differential scanning calorimetry (DSC) thermogram having at least one endotherm with an onset of about 250, 251 or 258° C. In some embodiments, the Compound I Form A is characterized by: (a) an XRPD pattern substantially as shown in FIG. 4; and (b) a DSC thermogram substantially as shown in FIG. 6.

Form C

In some embodiments, the present invention provides a crystalline anhydrate form of (E)-6-(4-Phenylcyclohexyl)-5-(3-trifluoromethylbenzyl)-1H-pyrimidine-2,4-dione (Compound I):

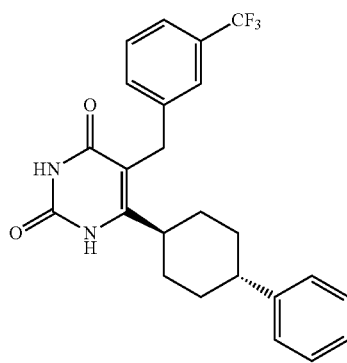

characterized by an X-ray powder diffraction (XRPD) pattern comprising three or more peaks at 17.3, 17.9, 18.3, 18.4, 21.3, or 21.8° 2θ±0.2° 2θ, Form C.

In some embodiments, the Compound I Form C is characterized by an XRPD pattern comprising four or more peaks at 17.3, 17.9, 18.3, 18.4, 21.3, or 21.8° 2θ±0.2° 2θ. In some embodiments, the Compound I Form C is characterized by an XRPD pattern comprising five or more peaks at 17.3, 17.9, 18.3, 18.4, 21.3, or 21.8° 2θ±0.2° 2θ. In some embodiments, the Compound I Form C is characterized by an XRPD pattern comprising peaks at 17.3, 17.9, 18.3, 18.4, 21.3, and 21.8° 2θ±0.2° 2θ.

In some embodiments, the Compound I Form C is characterized by an XRPD pattern further comprising one or more peaks at 8.8, 10.6, 14.3, 15.1, 17.7, 19.3, 22.5, 26.2, or 27.6° 2θ±0.2° 2θ. In some embodiments, the Compound I Form C is characterized by an XRPD pattern further comprising two or more peaks at 8.8, 10.6, 14.3, 15.1, 17.7, 19.3, 22.5, 26.2, or 27.6° 2θ±0.2° 2θ. In some embodiments, the Compound I Form C is characterized by an XRPD pattern further comprising three or more peaks at 8.8, 10.6, 14.3, 15.1, 17.7, 19.3, 22.5, 26.2, or 27.6° 2θ±0.2° 2θ. In some embodiments, the Compound I Form C is characterized by an XRPD pattern further comprising four or more peaks at 8.8, 10.6, 14.3, 15.1, 17.7, 19.3, 22.5, 26.2, or 27.6° 2θ±0.2° 2θ. In some embodiments, the Compound I Form C is characterized by an XRPD pattern further comprising peaks at 8.8, 10.6, 14.3, 15.1, 17.7, 19.3, 22.5, 26.2, and 27.6° 2θ±0.2° 2θ.

Figure 7:
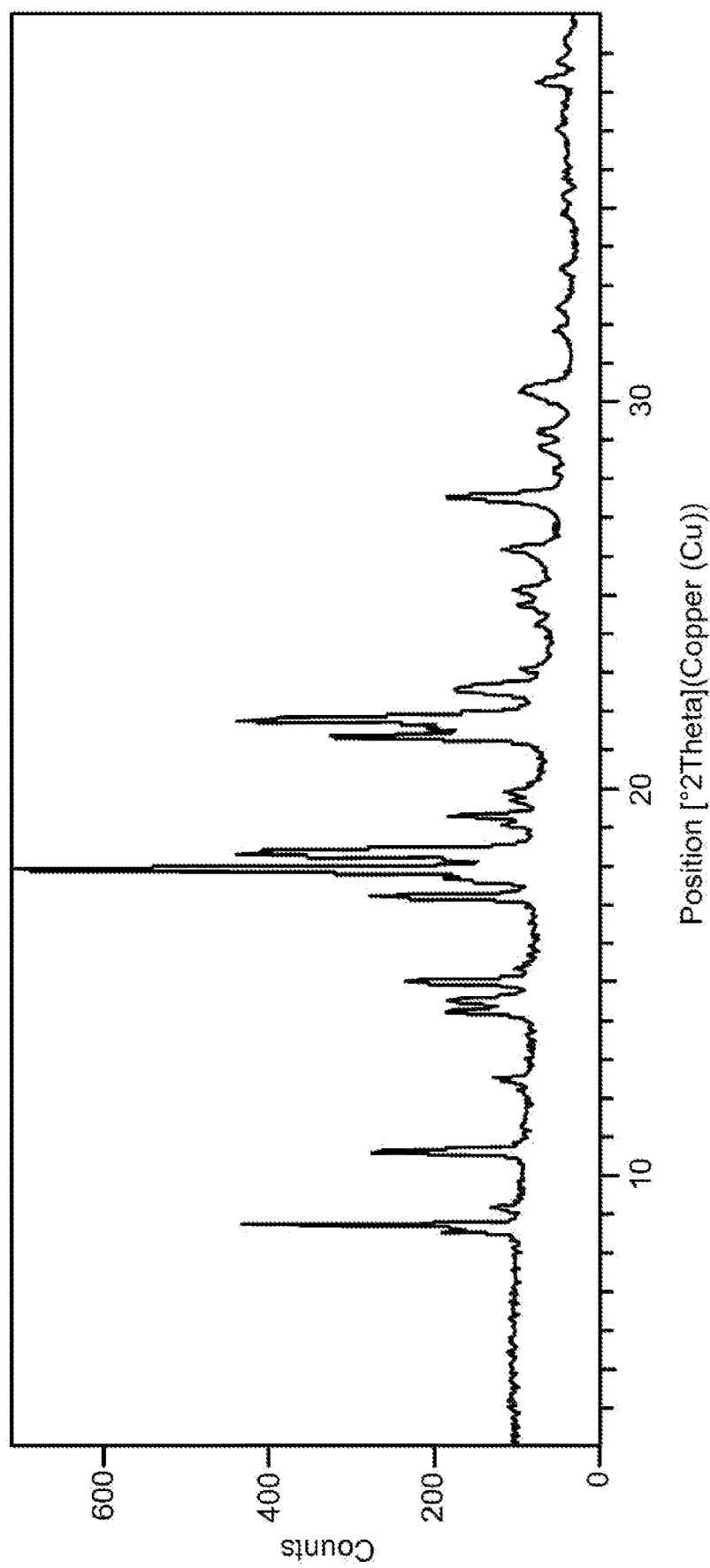
FIG. 7 shows the XRPD pattern for Compound I Form C.

In some embodiments, the Compound I Form C is characterized by an XRPD pattern comprising peaks at 8.8, 10.6, 14.3, 15.1, 17.3, 17.7, 17.9, 18.3, 18.4, 19.3, 21.3, 21.8, 22.5, 26.2, and 27.6° 2θ±0.2° 2θ. In some embodiments, the Compound I Formula C is characterized by an XRPD pattern substantially as shown in FIG. 7.

Figure 9:
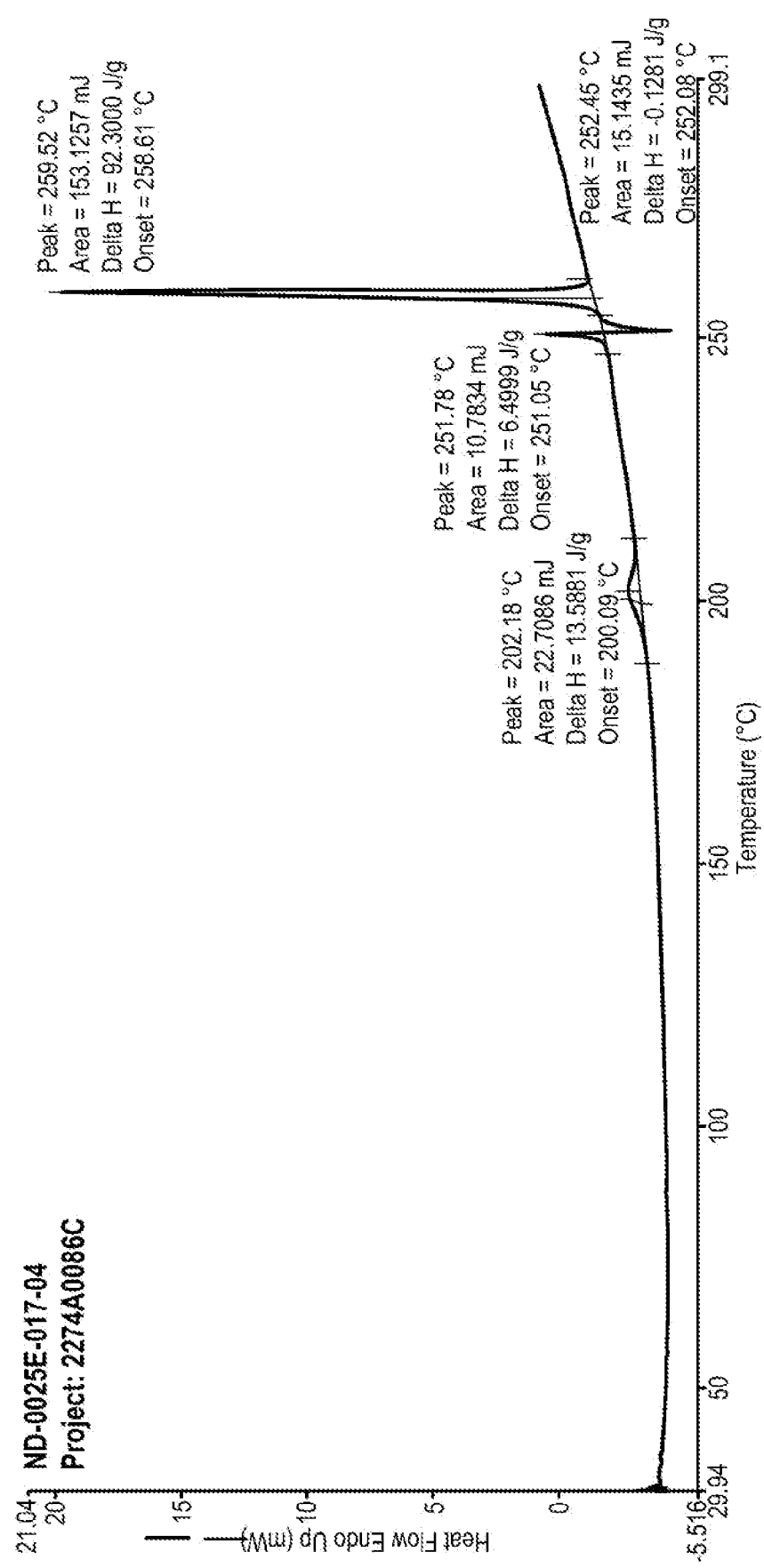
FIG. 9 shows the DSC and TGA thermogram for Compound I Form C.

In some embodiments, the Compound I Form C is characterized by a differential scanning calorimetry (DSC) thermogram having at least one endotherm with an onset of about 200, 251, 252 or 258° C. In some embodiments, the Compound I Form C is characterized by a DSC thermogram substantially as shown in FIG. 9.

In some embodiments, the Compound I Form C is characterized by: (a) an XRPD pattern comprising peaks at 17.3, 17.9, 18.3, 18.4, 21.3, and 21.8° 2θ±0.2° 2θ; and (b) a differential scanning calorimetry (DSC) thermogram having at least one endotherm with an onset of about 200, 251, 252 or 258° C. In some embodiments, the Compound I Form C is characterized by: (a) an XRPD pattern substantially as shown in FIG. 7; and (b) a DSC thermogram substantially as shown in FIG. 9.

Form F

In some embodiments, the present invention provides a crystalline anhydrate form of (E)-6-(4-Phenylcyclohexyl)-5-(3-trifluoromethylbenzyl)-1H-pyrimidine-2,4-dione (Compound I):

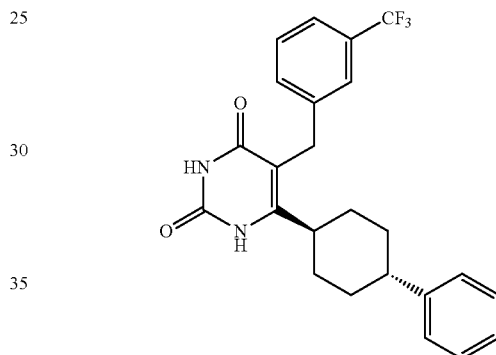

characterized by an X-ray powder diffraction (XRPD) pattern comprising three or more peaks at 15.9, 16.4, 16.8, 17.3, 19.0, 21.1, or 25.8° 2θ±0.2° 2θ, Form F.

In some embodiments, the Compound I Form F is characterized by an XRPD pattern comprising four or more peaks at 15.9, 16.4, 16.8, 17.3, 19.0, 21.1, or 25.8° 2θ±0.2° 2θ. In some embodiments, the Compound I Form F is characterized by an XRPD pattern comprising five or more peaks at 15.9, 16.4, 16.8, 17.3, 19.0, 21.1, or 25.8° 2θ±0.2° 2θ. In some embodiments, the Compound I Form F is characterized by an XRPD pattern comprising peaks at 15.9, 16.4, 16.8, 17.3, 19.0, 21.1, and 25.8° 2θ±0.2° 2θ.

In some embodiments, the Compound I Form F is characterized by an XRPD pattern further comprising one or more peaks at 9.3, 9.7, 14.1, 14.3, 17.8, 19.4, 20.4, 20.7, 21.5, 22.3, 23.8, 25.1, 26.7, 31.2, or 35.3° 2θ±0.2° 2θ. In some embodiments, the Compound I Form F is characterized by an XRPD pattern further comprising two or more peaks at 9.3, 9.7, 14.1, 14.3, 17.8, 19.4, 20.4, 20.7, 21.5, 22.3, 23.8, 25.1, 26.7, 31.2, or 35.3° 2θ±0.2° 2θ. In some embodiments, the Compound I Form F is characterized by an XRPD pattern further comprising three or more peaks at 9.3, 9.7, 14.1, 14.3, 17.8, 19.4, 20.4, 20.7, 21.5, 22.3, 23.8, 25.1, 26.7, 31.2, or 35.3° 2θ±0.2° 2θ. In some embodiments, the Compound I Form F is characterized by an XRPD pattern further comprising four or more peaks at 9.3, 9.7, 14.1, 14.3, 17.8, 19.4, 20.4, 20.7, 21.5, 22.3, 23.8, 25.1, 26.7, 31.2, or 35.3° 2θ±0.2° 2θ. In some embodiments, the Compound I Form F is characterized by an XRPD pattern further comprising peaks at 9.3, 9.7, 14.1, 14.3, 17.8, 19.4, 20.4, 20.7, 21.5, 22.3, 23.8, 25.1, 26.7, 31.2, and 35.3° 2θ±0.2° 2θ.

Figure 10:
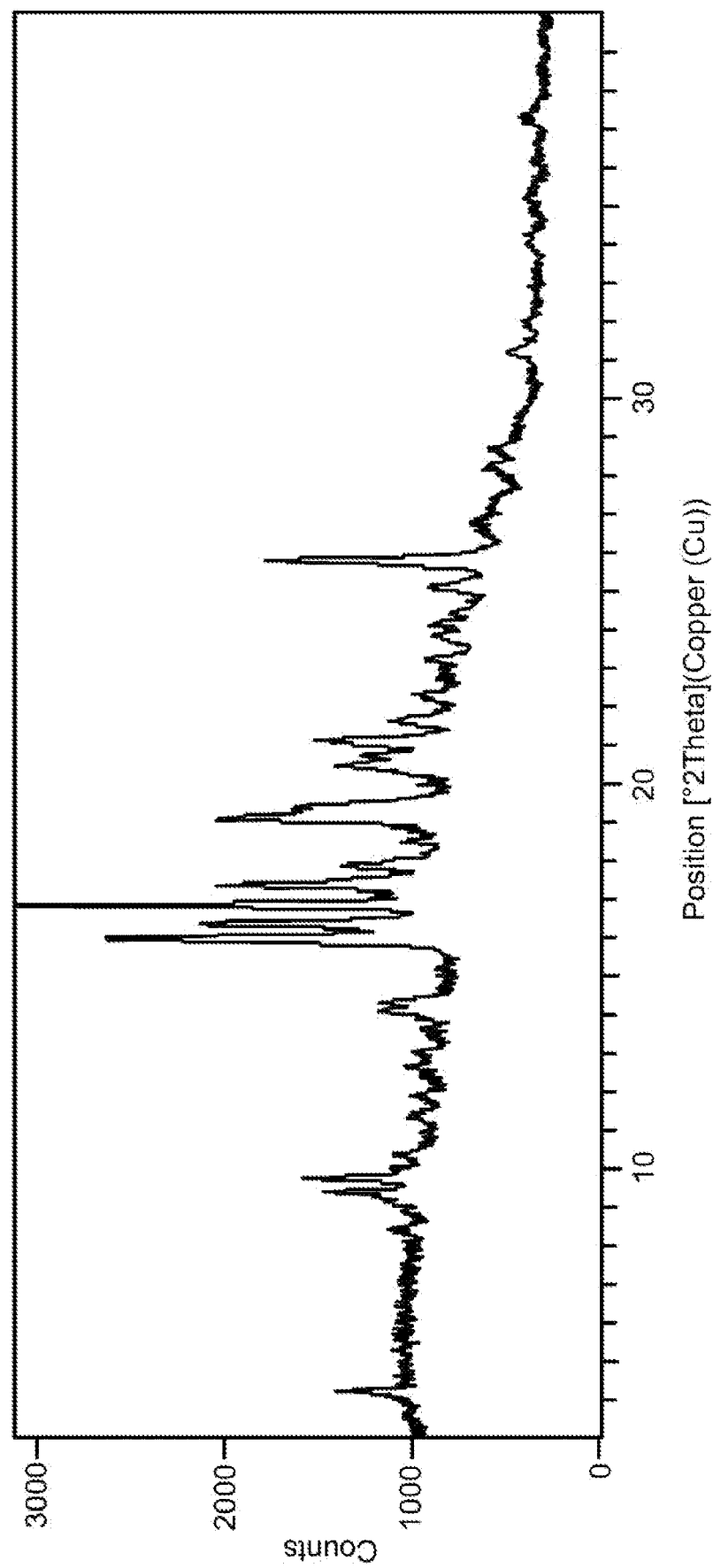
FIG. 10 shows the XRPD pattern for Compound I Form F.

In some embodiments, the Compound I Form F is characterized by an XRPD pattern comprising peaks at 9.3, 9.7, 14.1, 14.3, 15.9, 16.4, 16.8, 17.3, 17.8, 19.0, 19.4, 20.4, 20.7, 21.1, 21.5, 22.3, 23.8, 25.1, 25.8, 26.7, 31.2, and 35.3° 2θ±0.2° 2θ. In some embodiments, the Compound I Form F is characterized by an XRPD pattern substantially as shown in FIG. 10.

Figure 12:
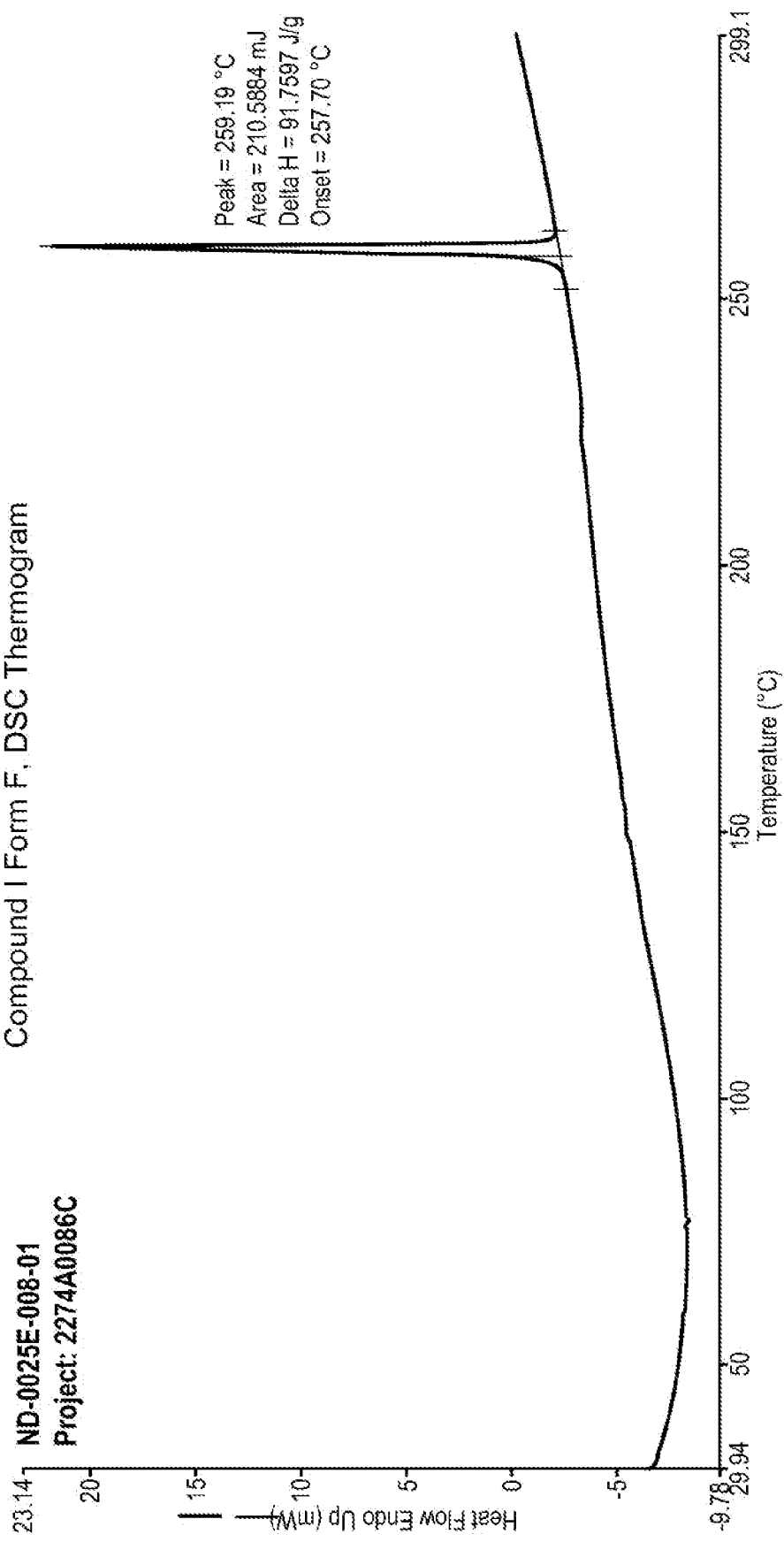
FIG. 12 shows the DSC and TGA thermogram for Compound I Form F.

In some embodiments, the Compound I Form F is characterized by a differential scanning calorimetry (DSC) thermogram having at least one endotherm with an onset of about 257° C. In some embodiments, the Compound I Form F is characterized by a DSC thermogram substantially as shown in FIG. 12.

In some embodiments, the Compound I Form F is characterized by: (a) an XRPD pattern comprising peaks at 15.9, 16.4, 16.8, 17.3, 19.0, 21.1, or 25.8° 2θ±0.2° 2θ; and (b) a differential scanning calorimetry (DSC) thermogram having at least one endotherm with an onset of about 257° C. In some embodiments, the Compound I Form F is characterized by: (a) an XRPD pattern substantially as shown in FIG. 10; and (b) a DSC thermogram substantially as shown in FIG. 12.

Form J

In some embodiments, the present invention provides a crystalline anhydrate form of (E)-6-(4-Phenylcyclohexyl)-5-(3-trifluoromethylbenzyl)-1H-pyrimidine-2,4-dione (Compound I):

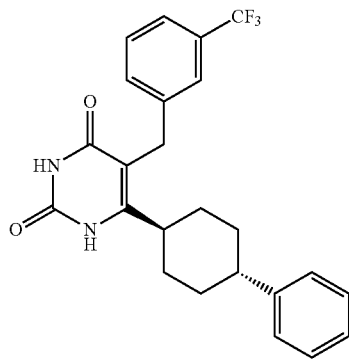 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 6.0, 13.1, 17.3, 18.8, 19.8, 20.1, or 21.9° 2θ±0.2° 2θ, Form J.

In some embodiments, the Compound I Form J is characterized by an XRPD pattern comprising four or more peaks at 6.0, 13.1, 17.3, 18.8, 19.8, 20.1, or 21.9° 2θ±0.2° 2θ. In some embodiments, the Compound I Form J is characterized by an XRPD pattern comprising five or more peaks at 6.0, 13.1, 17.3, 18.8, 19.8, 20.1, or 21.9° 2θ±0.2° 2θ. In some embodiments, the Compound I Form J is characterized by an XRPD pattern comprising peaks at 6.0, 13.1, 17.3, 18.8, 19.8, 20.1, and 21.9° 2θ±0.2° 2θ.

In some embodiments, the Compound I Form J is characterized by an XRPD pattern further comprising one or more peaks at 13.7, 15.6, 18.1, 18.3, 19.1, or 27.4° 2θ±0.2° 2θ. In some embodiments, the Compound I Form J is characterized by an XRPD pattern further comprising two or more peaks at 13.7, 15.6, 18.1, 18.3, 19.1, or 27.4° 2θ±0.2° 2θ. In some embodiments, the Compound I Form J is characterized by an XRPD pattern further comprising three or more peaks at 13.7, 15.6, 18.1, 18.3, 19.1, or 27.4° 2θ±0.2° 2θ. In some embodiments, the Compound I Form J is characterized by an XRPD pattern further comprising four or more peaks at 13.7, 15.6, 18.1, 18.3, 19.1, or 27.4° 2θ±0.2° 2θ. In some embodiments, the Compound I Form J is characterized by an XRPD pattern further comprising peaks at 13.7, 15.6, 18.1, 18.3, 19.1, and 27.4° 2θ±0.2° 2θ.

Figure 16:
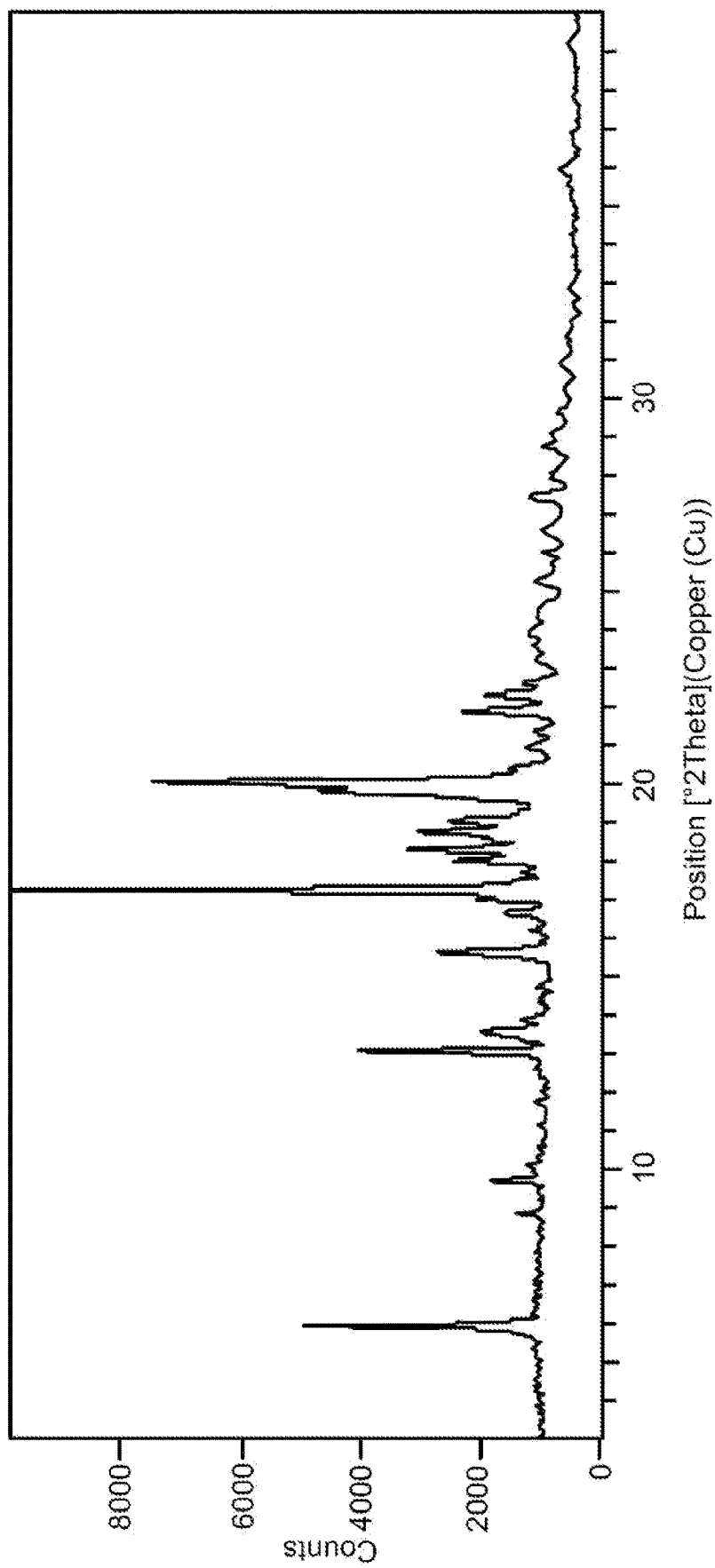
FIG. 16 shows the XRPD pattern for Compound I Form J.

In some embodiments, the Compound I Form J is characterized by an XRPD pattern comprising peaks at 6.0, 13.1, 13.7, 15.6, 17.3, 18.1, 18.3, 18.8, 19.1, 19.8, 20.1, 21.9, 27.4° 2θ±0.2° 2θ. In some embodiments, the Compound I Form J is characterized by an XRPD pattern substantially as shown in FIG. 16.

Figure 18:
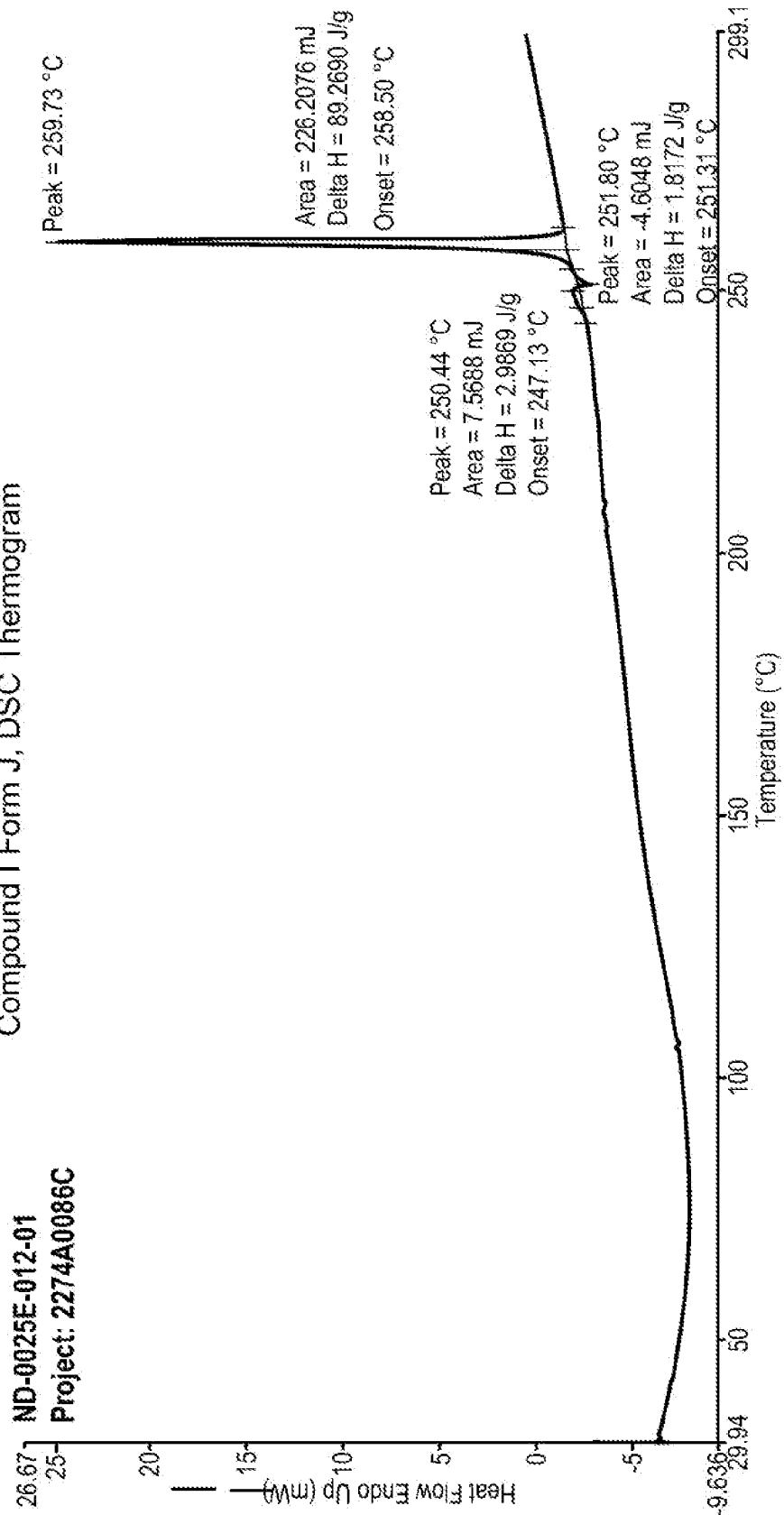
FIG. 18 shows the DSC and TGA thermogram for Compound I Form J.

In some embodiments, the Compound I Form J is characterized by a differential scanning calorimetry (DSC) thermogram having at least one endotherm with an onset of about 247, 251 or 258° C. In some embodiments, the Compound I Form J is characterized by a DSC thermogram substantially as shown in FIG. 18.

In some embodiments, the Compound I Form J is characterized by: (a) an XRPD pattern comprising peaks at 6.0, 13.1, 17.3, 18.8, 19.8, 20.1, and 21.9° 2θ±0.2° 2θ; and (b) a differential scanning calorimetry (DSC) thermogram having at least one endotherm with an onset of about 247, 251 or 258° C. In some embodiments, the Compound I Form J is characterized by: (a) an XRPD pattern substantially as shown in FIG. 16; and (b) a DSC thermogram substantially as shown in FIG. 18.

Form L

In some embodiments, the present invention provides a crystalline anhydrate form of (E)-6-(4-Phenylcyclohexyl)-5-(3-trifluoromethylbenzyl)-1H-pyrimidine-2,4-dione (Compound I):

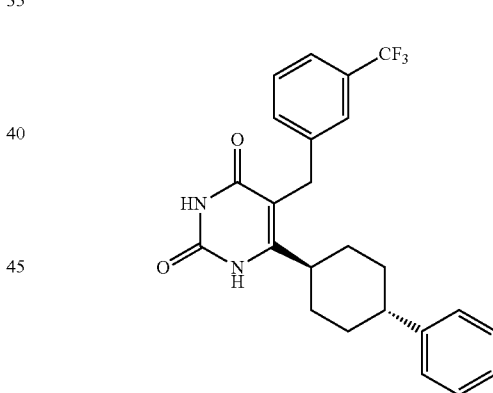

characterized by an X-ray powder diffraction (XRPD) pattern comprising three or more peaks at 14.6, 15.5, 19.4, 19.7, or 22.2° 2θ±0.2° 2θ, Form L.

In some embodiments, the Compound I Form L is characterized by an XRPD pattern comprising four or more peaks at 14.6, 15.5, 19.4, 19.7, or 22.2° 2θ±0.2° 2θ. In some embodiments, the Compound I Form L is characterized by an XRPD pattern comprising five or more peaks at 14.6, 15.5, 19.4, 19.7, or 22.2° 2θ±0.2° 2θ. In some embodiments, the Compound I Form L is characterized by an XRPD pattern comprising peaks at 14.6, 15.5, 19.4, 19.7, and 22.2° 2θ±0.2° 2θ.

In some embodiments, the Compound I Form L is characterized by an XRPD pattern further comprising one or more peaks at 13.1, 13.6, 17.2, 18.6, 20.6, 21.7, 23.2, 24.5, 26.1, 27.5, or 28.6° 2θ±0.2° 2θ. In some embodiments, the Compound I Form L is characterized by an XRPD pattern further comprising two or more peaks at 13.1, 13.6, 17.2, 18.6, 20.6, 21.7, 23.2, 24.5, 26.1, 27.5, or 28.6° 2θ±0.2° 2θ. In some embodiments, the Compound I Form L is characterized by an XRPD pattern further comprising three or more peaks at 13.1, 13.6, 17.2, 18.6, 20.6, 21.7, 23.2, 24.5, 26.1, 27.5, or 28.6° 2θ±0.2° 2θ. In some embodiments, the Compound I Form L is characterized by an XRPD pattern further comprising four or more peaks at 13.1, 13.6, 17.2, 18.6, 20.6, 21.7, 23.2, 24.5, 26.1, 27.5, or 28.6° 2θ±0.2° 2θ. In some embodiments, the Compound I Form L is characterized by an XRPD pattern further comprising peaks at 13.1, 13.6, 17.2, 18.6, 20.6, 21.7, 23.2, 24.5, 26.1, 27.5, and 28.6° 2θ±0.2° 2θ.

Figure 22:
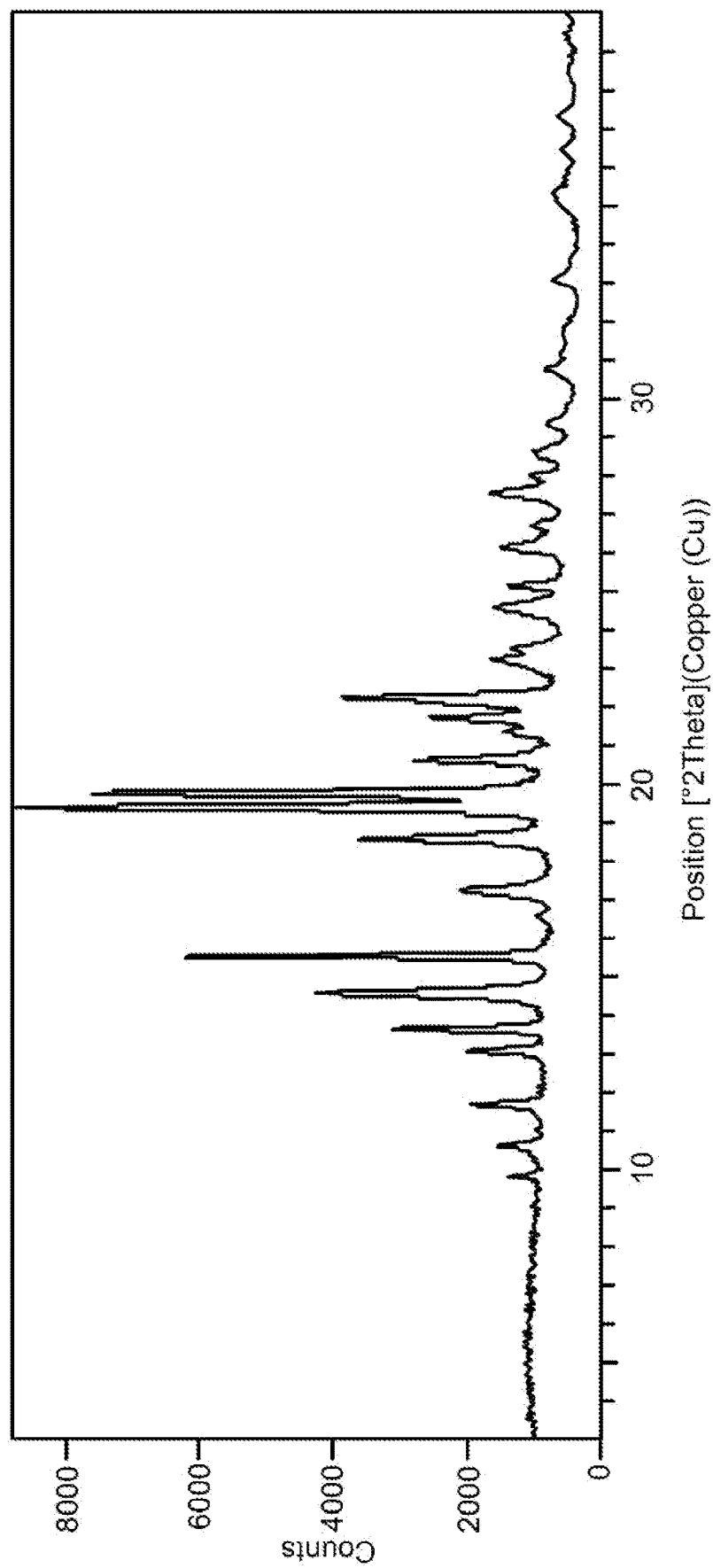
FIG. 22 shows the XRPD pattern for Compound I Form L.

In some embodiments, the Compound I Form L is characterized by an XRPD pattern comprising peaks at 13.1, 13.6, 14.6, 15.5, 17.2, 18.6, 19.4, 19.7, 20.6, 21.7, 22.2, 23.2, 24.5, 26.1, 27.5, and 28.6° 2θ±0.2° 2θ. In some embodiments, the Compound I Form L is characterized by an XRPD pattern substantially as shown in FIG. 22.

Figure 24:
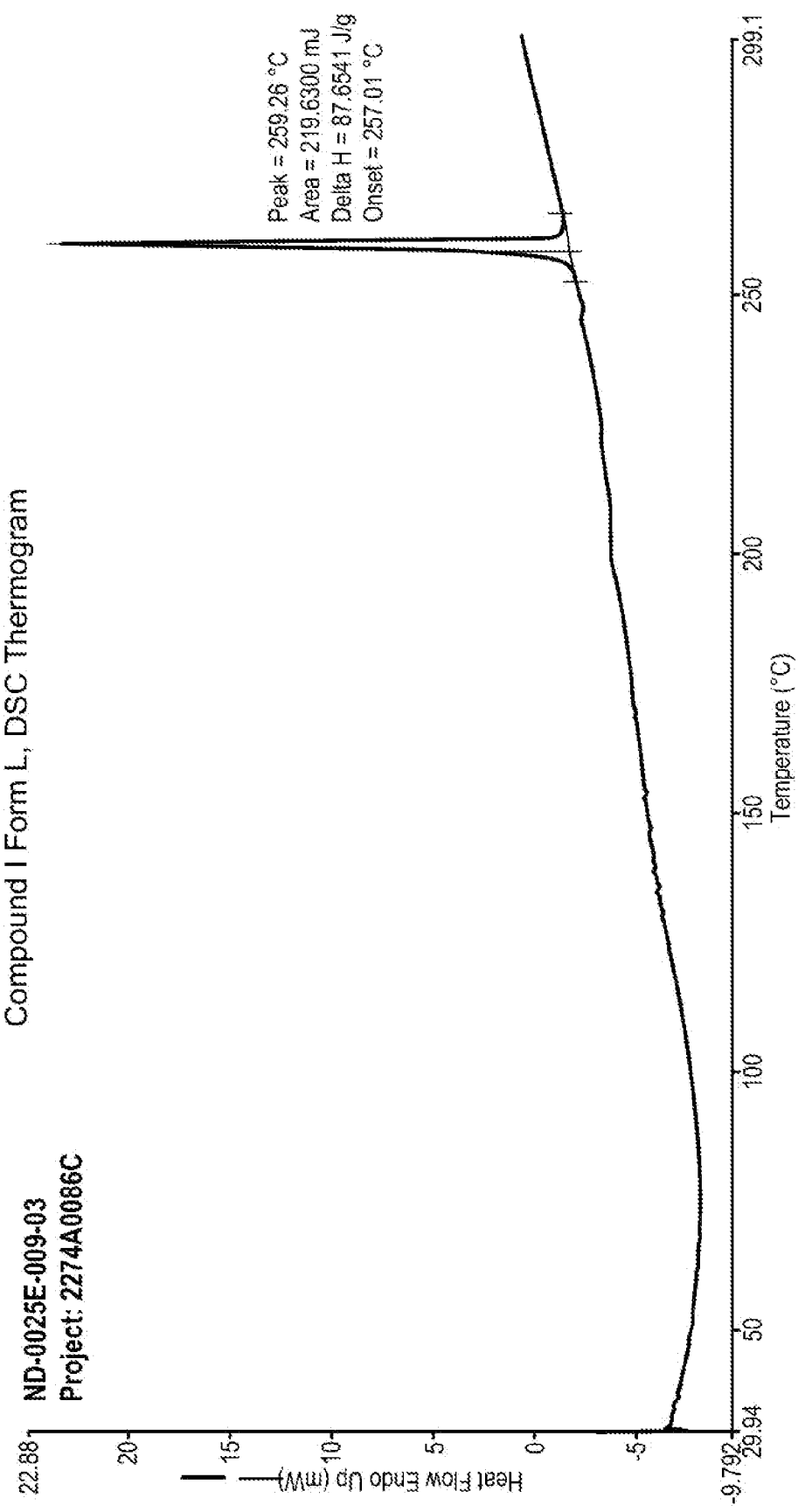
FIG. 24 shows the DSC and TGA thermogram for Compound I Form L.

In some embodiments, the Compound I Form L is characterized by a differential scanning calorimetry (DSC) thermogram having at least one endotherm with an onset of about 257° C. In some embodiments, the Compound I Form L is characterized by a DSC thermogram substantially as shown in FIG. 24.

In some embodiments, the Compound I Form L is characterized by: (a) an XRPD pattern comprising peaks at 14.6, 15.5, 19.4, 19.7, and 22.2° 2θ±0.2° 2θ; and (b) a differential scanning calorimetry (DSC) thermogram having an endotherm with an onset of about 257° C. In some embodiments, the Compound I Form L is characterized by: (a) an XRPD pattern substantially as shown in FIG. 22; and (b) a DSC thermogram substantially as shown in FIG. 24.

THF Solvate Form H

In some embodiments, the present invention provides a crystalline form of (E)-6-(4-Phenylcyclohexyl)-5-(3-trifluoromethylbenzyl)-1H-pyrimidine-2,4-dione THF solvate (Compound I, THF solvate):

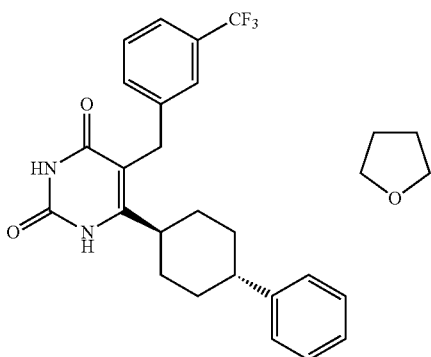

characterized by an X-ray powder diffraction (XRPD) pattern comprising three or more peaks at 17.2, 18.9, 20.9, 23.5, 25.0, or 25.6° 2θ±0.2° 2θ, THF solvate Form H.

In some embodiments, the Compound I THF solvate Form H is characterized by an XRPD pattern comprising four or more peaks at 17.2, 18.9, 20.9, 23.5, 25.0, or 25.6° 2θ±0.2° 2θ. In some embodiments, the Compound I THF solvate Form H is characterized by an XRPD pattern comprising five or more peaks at 17.2, 18.9, 20.9, 23.5, 25.0, or 25.6° 2θ±0.2° 2θ. In some embodiments, the Compound I THF solvate Form H is characterized by an XRPD pattern comprising peaks at 17.2, 18.9, 20.9, 23.5, 25.0, and 25.6° 2θ±0.2° 2θ.

In some embodiments, the Compound I THF solvate Form H is characterized by an XRPD pattern further comprising one or more peaks at 7.9, 11.0, 12.0, 12.4, 13.0, 15.7, 17.0, 17.1, 19.1, 20.4, or 20.6° 2θ±0.2° 2θ. In some embodiments, the Compound I THF solvate Form H is characterized by an XRPD pattern further comprising two or more peaks at 7.9, 11.0, 12.0, 12.4, 13.0, 15.7, 17.0, 17.1, 19.1, 20.4, or 20.6° 2θ±0.2° 2θ. In some embodiments, the Compound I THF solvate Form H is characterized by an XRPD pattern further comprising three or more peaks at 7.9, 11.0, 12.0, 12.4, 13.0, 15.7, 17.0, 17.1, 19.1, 20.4, or 20.6° 2θ±0.2° 2θ. In some embodiments, the Compound I THF solvate Form H is characterized by an XRPD pattern further comprising four or more peaks at 7.9, 11.0, 12.0, 12.4, 13.0, 15.7, 17.0, 17.1, 19.1, 20.4, or 20.6° 2θ±0.2° 2θ. In some embodiments, the Compound I THF solvate Form H is characterized by an XRPD pattern further comprising peaks at 7.9, 11.0, 12.0, 12.4, 13.0, 15.7, 17.0, 17.1, 19.1, 20.4, and 20.6° 2θ±0.2° 2θ.

Figure 13:
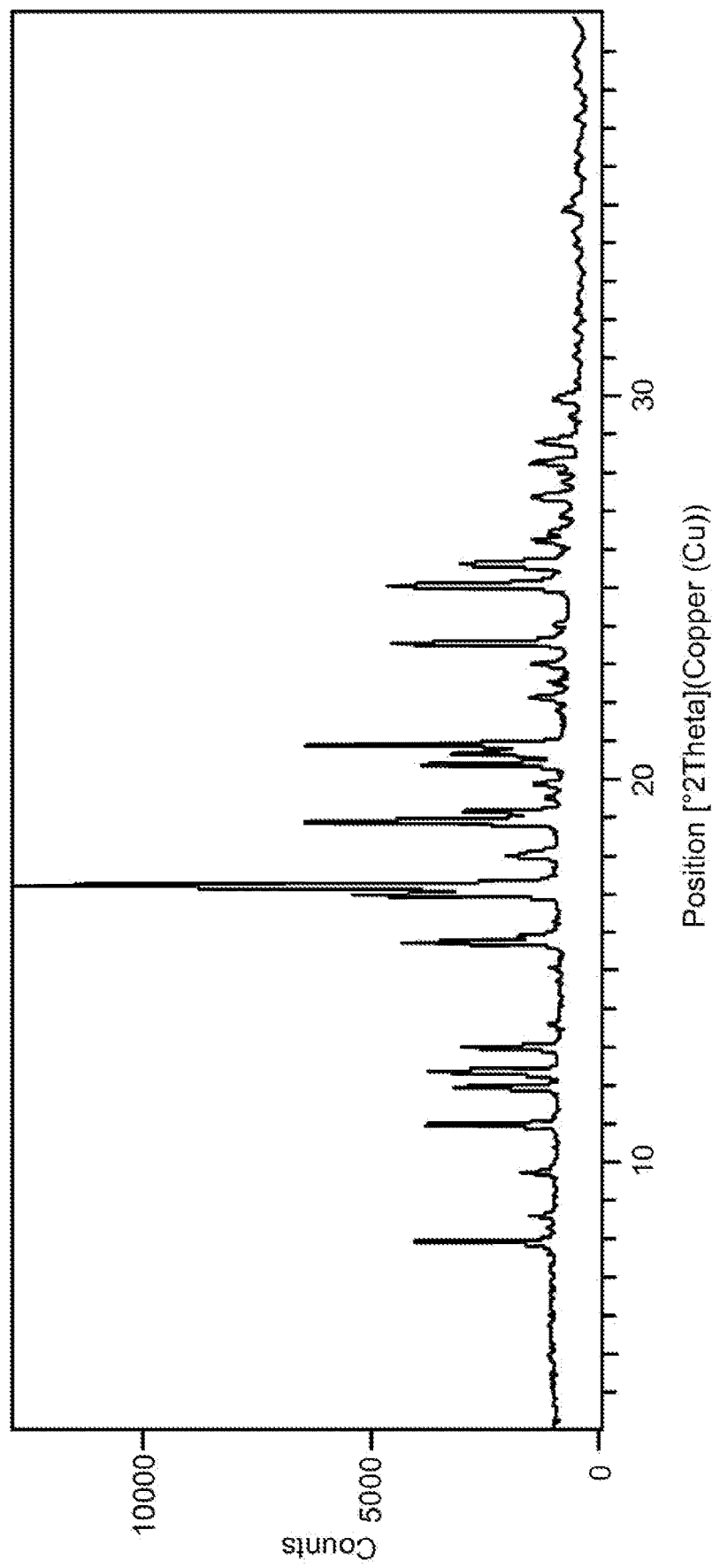
FIG. 13 shows the XRPD pattern for Compound I THF solvate Form H.

In some embodiments, the Compound I THF solvate Form H is characterized by an XRPD pattern comprising peaks at 7.9, 11.0, 12.0, 12.4, 13.0, 15.7, 17.0, 17.1, 17.2, 18.9, 19.1, 20.4, 20.6, 20.9, 23.5, 25.0, and 25.6° 2θ±0.2° 2θ. In some embodiments, the Compound I THF solvate Form H is characterized by an XRPD pattern substantially as shown in FIG. 13.

Figure 15:
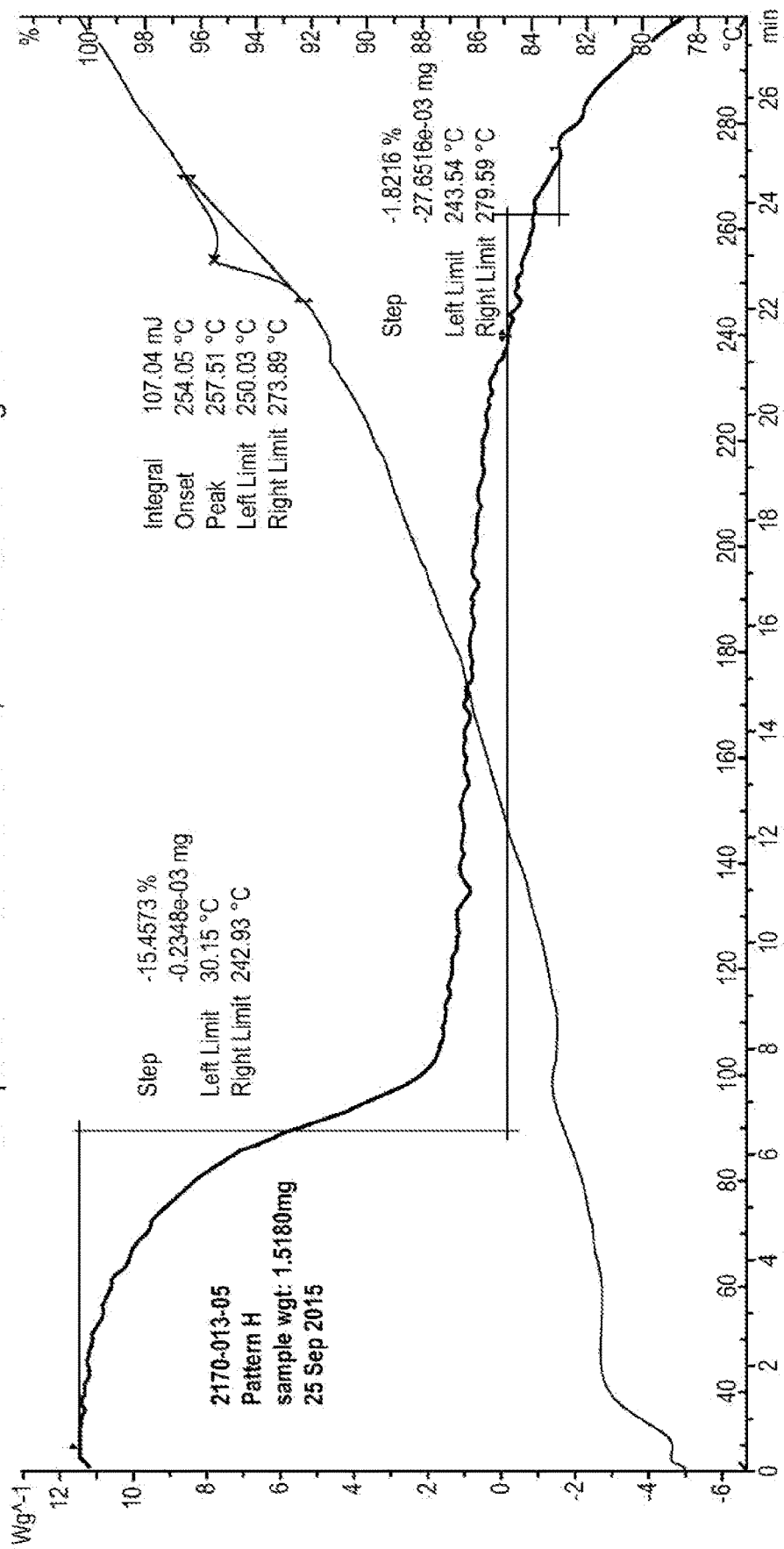
FIG. 15 shows the DSC and TGA thermogram for Compound I THF solvate Form H.

In some embodiments, the Compound I THF solvate Form H is characterized by a differential scanning calorimetry (DSC) thermogram having at least one endotherm with an onset of about 254° C. In some embodiments, the Compound I THF solvate Form H is characterized by a DSC thermogram substantially as shown in FIG. 15.

In some embodiments, the Compound I THF solvate Form H is characterized by: (a) an XRPD pattern comprising peaks at 17.2, 18.9, 20.9, 23.5, 25.0, and 25.6° 2θ±0.2° 2θ; and (b) a differential scanning calorimetry (DSC) thermogram having an endotherm with an onset of about 254° C. In some embodiments, the Compound I THF solvate Form H is characterized by: (a) an XRPD pattern substantially as shown in FIG. 13; and (b) a DSC thermogram substantially as shown in FIG. 15.

AcOH Solvate Form K

In some embodiments, the present invention provides a crystalline form of (E)-6-(4-Phenylcyclohexyl)-5-(3-trifluoromethylbenzyl)-1H-pyrimidine-2,4-dione acetic acid (Compound I, acetic acid solvate):

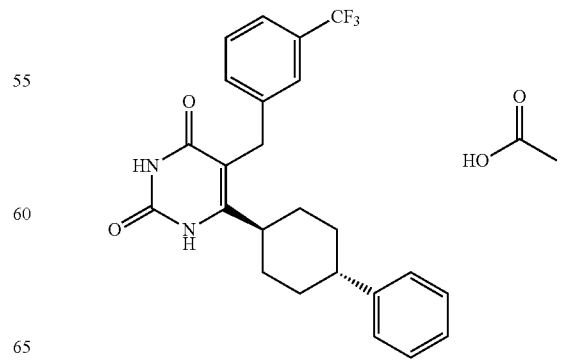

characterized by an X-ray powder diffraction (XRPD) pattern comprising three or more peaks at 16.0, 16.8, 19.4, 22.3, 23.6, or 26.9° 2θ±0.2° 2θ, AcOH solvate Form K.

In some embodiments, the Compound I AcOH solvate Form K is characterized by an XRPD pattern comprising four or more peaks at 16.0, 16.8, 19.4, 22.3, 23.6, or 26.9° 2θ±0.2° 2θ. In some embodiments, the Compound I AcOH solvate Form K is characterized by an XRPD pattern comprising five or more peaks at 16.0, 16.8, 19.4, 22.3, 23.6, or 26.9° 2θ±0.2° 2θ. In some embodiments, the Compound I AcOH solvate Form K is characterized by an XRPD pattern comprising peaks at 16.0, 16.8, 19.4, 22.3, 23.6, or 26.9° 2θ±0.2° 2θ.

In some embodiments, the Compound I AcOH solvate Form K is characterized by an XRPD pattern further comprising one or more peaks at 7.3, 8.4, 10.8, 11.0, 13.0, 15.2, 16.7, 18.5, 19.0, 19.1, 19.3, 19.9, 20.3, 22.0, 23.1, 24.0, 24.1, 25.2, 25.6, 26.2, 27.7, 29.1, 30.0, or 33.7° 2θ±0.2° 2θ. In some embodiments, the Compound I AcOH solvate Form K is characterized by an XRPD pattern further comprising two or more peaks at 7.3, 8.4, 10.8, 11.0, 13.0, 15.2, 16.7, 18.5, 19.0, 19.1, 19.3, 19.9, 20.3, 22.0, 23.1, 24.0, 24.1, 25.2, 25.6, 26.2, 27.7, 29.1, 30.0, or 33.7° 2θ±0.2° 2θ. In some embodiments, the Compound I AcOH solvate Form K is characterized by an XRPD pattern further comprising three or more peaks at 7.3, 8.4, 10.8, 11.0, 13.0, 15.2, 16.7, 18.5, 19.0, 19.1, 19.3, 19.9, 20.3, 22.0, 23.1, 24.0, 24.1, 25.2, 25.6, 26.2, 27.7, 29.1, 30.0, or 33.7° 2θ±0.2° 2θ. In some embodiments, the Compound I AcOH solvate Form K is characterized by an XRPD pattern further comprising four or more peaks at 7.3, 8.4, 10.8, 11.0, 13.0, 15.2, 16.7, 18.5, 19.0, 19.1, 19.3, 19.9, 20.3, 22.0, 23.1, 24.0, 24.1, 25.2, 25.6, 26.2, 27.7, 29.1, 30.0, or 33.7° 2θ±0.2° 2θ. In some embodiments, the Compound I AcOH solvate Form K is characterized by an XRPD pattern further comprising peaks at 7.3, 8.4, 10.8, 11.0, 13.0, 15.2, 16.7, 18.5, 19.0, 19.1, 19.3, 19.9, 20.3, 22.0, 23.1, 24.0, 24.1, 25.2, 25.6, 26.2, 27.7, 29.1, 30.0, and 33.7° 2θ±0.2° 2θ.

Figure 19:
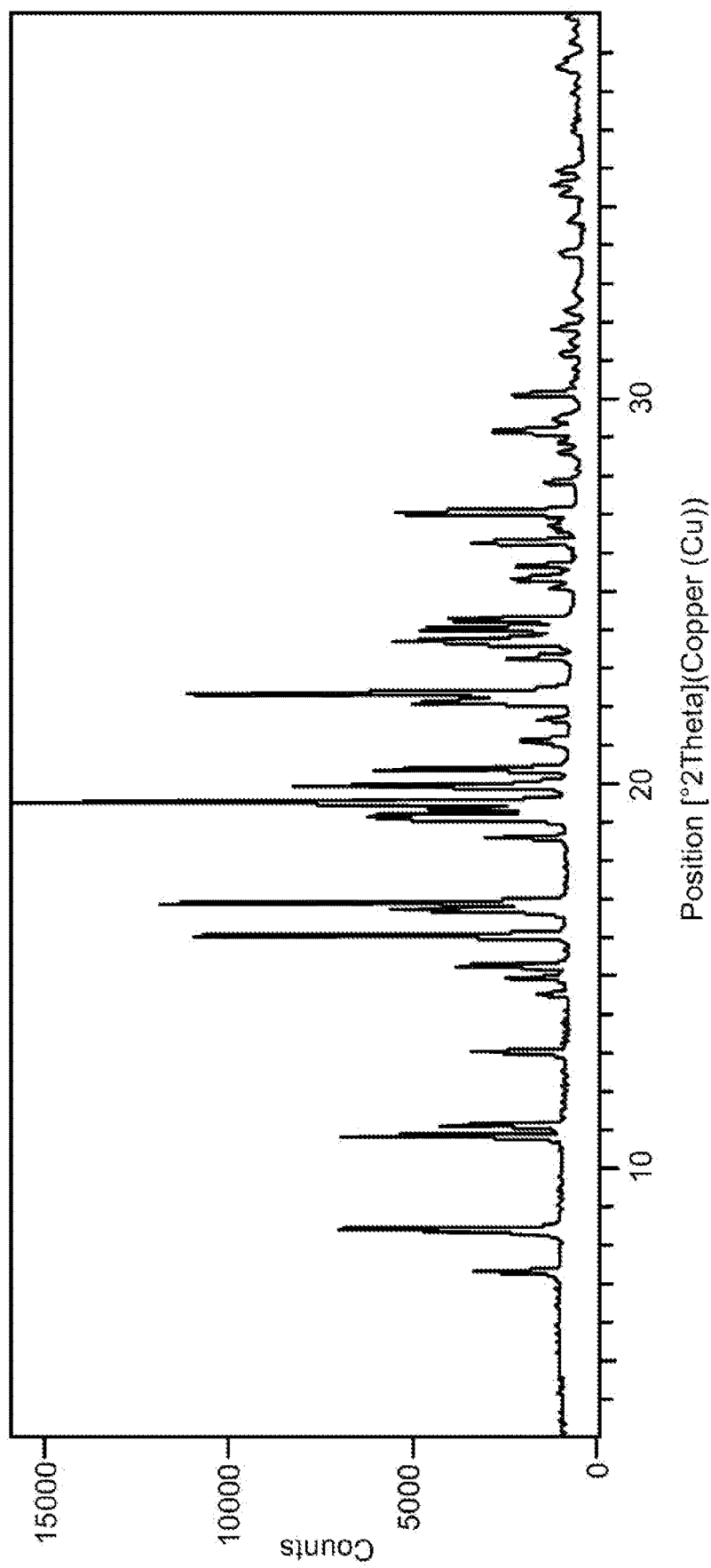
FIG. 19 shows the XRPD pattern for Compound I AcOH solvate Form K.

In some embodiments, the Compound I AcOH solvate Form K is characterized by an XRPD pattern comprising peaks at 7.3, 8.4, 10.8, 11.0, 13.0, 15.2, 16.0, 16.7, 16.8, 18.5, 19.0, 19.1, 19.3, 19.4, 19.9, 20.3, 22.0, 22.3, 23.1, 23.6, 24.0, 24.1, 25.2, 25.6, 26.2, 26.9, 27.7, 29.1, 30.0, and 33.7° 2θ±0.2° 2θ. In some embodiments, the Compound I AcOH solvate Form K is characterized by an XRPD pattern substantially as shown in FIG. 19.

Figure 21:
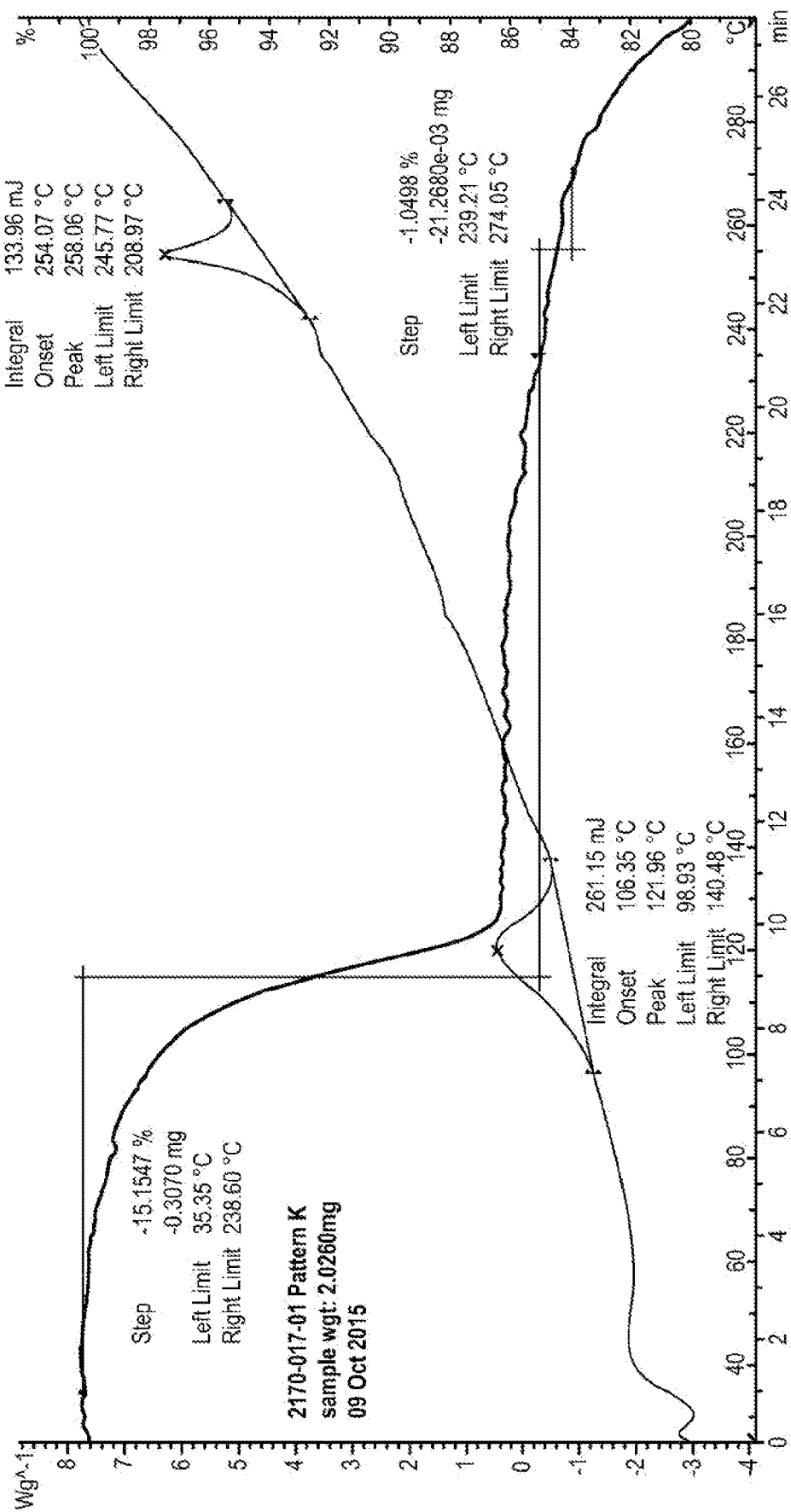
FIG. 21 shows the DSC and TGA thermogram for Compound I AcOH solvate Form K.

In some embodiments, the Compound I AcOH solvate Form K is characterized by a differential scanning calorimetry (DSC) thermogram having at least one endotherm with an onset of about 106 or 254° C. In some embodiments, the Compound I AcOH solvate Form K is characterized by a DSC thermogram substantially as shown in FIG. 21.

In some embodiments, the Compound I AcOH solvate Form K is characterized by: (a) an XRPD pattern comprising peaks at 16.0, 16.8, 19.4, 22.3, 23.6, or 26.9° 2θ±0.2° 2θ; and (b) a differential scanning calorimetry (DSC) thermogram having an endotherm with an onset of about 106 or 254° C. In some embodiments, the Compound I AcOH solvate Form K is characterized by: (a) an XRPD pattern substantially as shown in FIG. 19; and (b) a DSC thermogram substantially as shown in FIG. 21.

Dioxane Solvate Form M

In some embodiments, the present invention provides a crystalline form of (E)-6-(4-Phenylcyclohexyl)-5-(3-trifluoromethylbenzyl)-1H-pyrimidine-2,4-dione dioxane (Compound I, dioxane solvate):

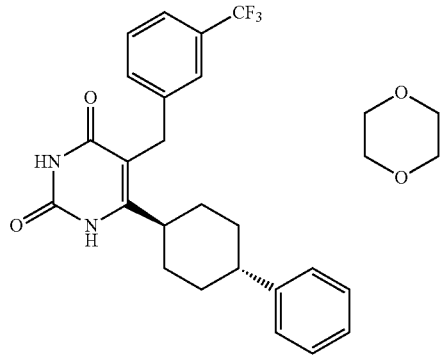 [SMILES: O=c1[nH]c(=O)c(Cc2cccc(C(F)(F)F)c2)c([C@H]2CC[C@H](c3ccccc3)CC2)[nH]1 ; C1COCCO1]

characterized by an X-ray powder diffraction (XRPD) pattern comprising three or more peaks at 15.3, 17.5, 19.5, 20.1, 20.7, or 26.8° 2θ±0.2° 2θ, Dioxane solvate Form M.

In some embodiments, the Compound I Dioxane solvate Form M is characterized by an XRPD pattern comprising four or more peaks at 15.3, 17.5, 19.5, 20.1, 20.7, or 26.8° 2θ±0.2° 2θ. In some embodiments, the Compound I Dioxane solvate Form M is characterized by an XRPD pattern comprising five or more peaks at 15.3, 17.5, 19.5, 20.1, 20.7, or 26.8° 2θ±0.2° 2θ. In some embodiments, the Compound I Dioxane solvate Form M is characterized by an XRPD pattern comprising peaks at 15.3, 17.5, 19.5, 20.1, 20.7, and 26.8° 2θ±0.2° 2θ.

In some embodiments, the Compound I Dioxane solvate Form M is characterized by an XRPD pattern further comprising one or more peaks at 10.7, 14.5, 16.2, 18.8, 19.1, 19.8, 20.4, 21.5, 22.3, 22.5, 25.1, 26.9, 28.7, 29.5, or 38.0° 2θ±0.2° 2θ. In some embodiments, the Compound I Dioxane solvate Form M is characterized by an XRPD pattern further comprising two or more peaks at 10.7, 14.5, 16.2, 18.8, 19.1, 19.8, 20.4, 21.5, 22.3, 22.5, 25.1, 26.9, 28.7, 29.5, or 38.0° 2θ±0.2° 2θ. In some embodiments, the Compound I Dioxane solvate Form M is characterized by an XRPD pattern further comprising three or more peaks at 10.7, 14.5, 16.2, 18.8, 19.1, 19.8, 20.4, 21.5, 22.3, 22.5, 25.1, 26.9, 28.7, 29.5, or 38.0° 2θ±0.2° 2θ. In some embodiments, the Compound I Dioxane solvate Form M is characterized by an XRPD pattern further comprising four or more peaks at 10.7, 14.5, 16.2, 18.8, 19.1, 19.8, 20.4, 21.5, 22.3, 22.5, 25.1, 26.9, 28.7, 29.5, or 38.0° 2θ±0.2° 2θ. In some embodiments, the Compound I Dioxane solvate Form M is characterized by an XRPD pattern further comprising peaks at 10.7, 14.5, 16.2, 18.8, 19.1, 19.8, 20.4, 21.5, 22.3, 22.5, 25.1, 26.9, 28.7, 29.5, and 38.0° 2θ±0.2° 2θ.

Figure 25:
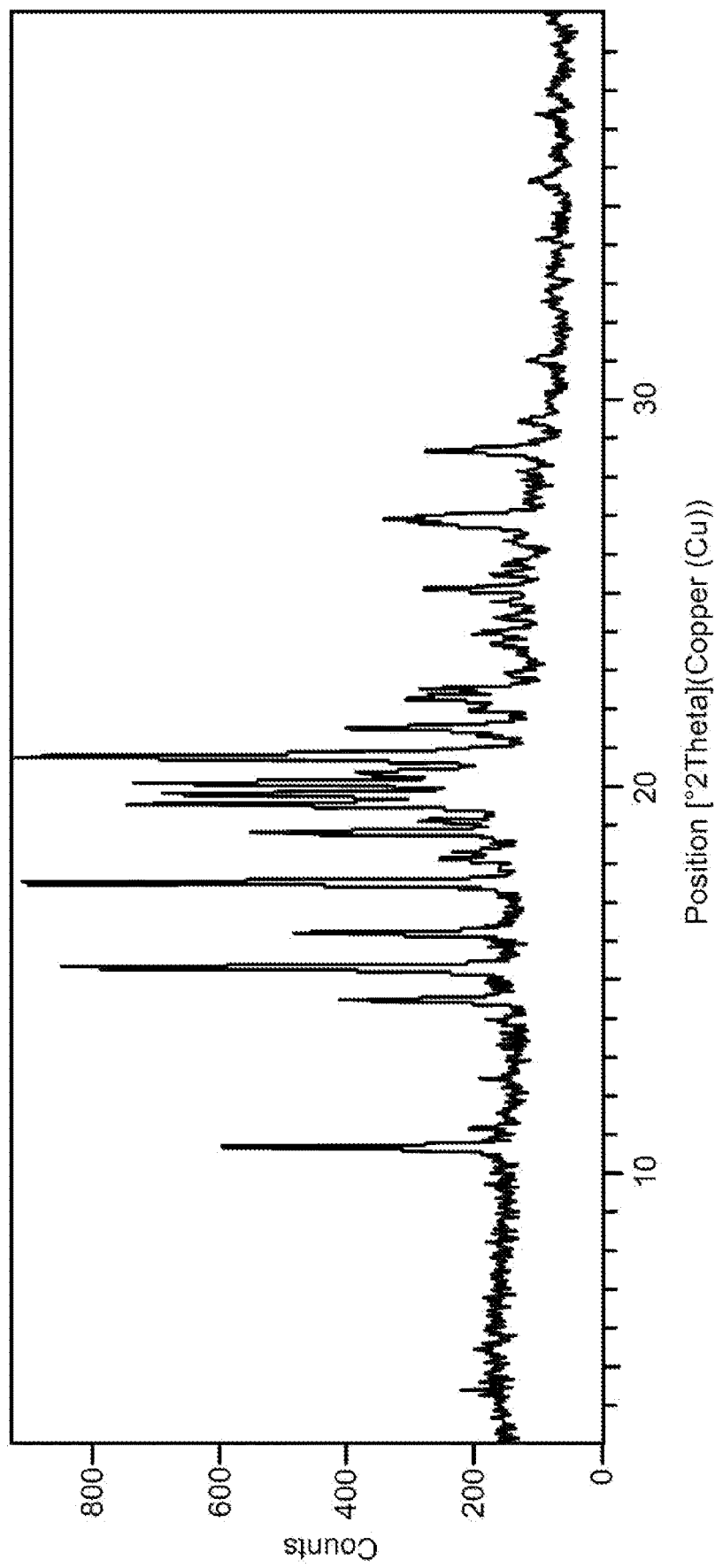
FIG. 25 shows the XRPD pattern for Compound I Dioxane solvate Form M.

In some embodiments, the Compound I Dioxane solvate Form M is characterized by an XRPD pattern comprising peaks at 10.7, 14.5, 15.3, 16.2, 17.5, 18.8, 19.1, 19.5, 19.8, 20.1, 20.4, 20.7, 21.5, 22.3, 22.5, 25.1, 26.8, 26.9, 28.7, 29.5, and 38.0° 2θ±0.2° 2θ. In some embodiments, the Compound I Dioxane solvate Form M is characterized by an XRPD pattern substantially as shown in FIG. 25.

Figure 27:
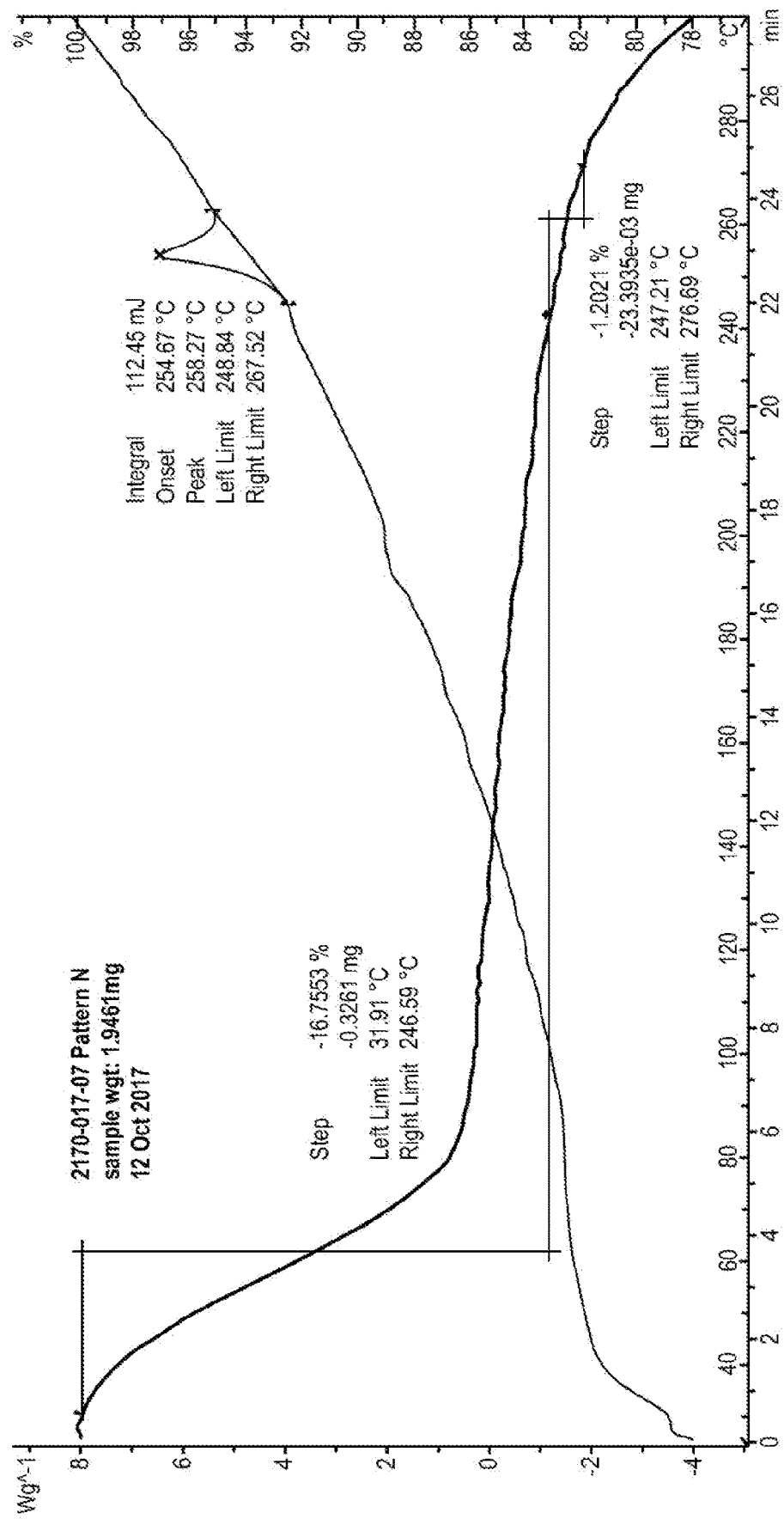
FIG. 27 shows the DSC and TGA thermogram for Compound I Dioxane solvate Form M.

In some embodiments, the Compound I Dioxane solvate Form M is characterized by a differential scanning calorimetry (DSC) thermogram having at least one endotherm with an onset of about 254° C. In some embodiments, the Compound I Dioxane solvate Form M is characterized by a DSC thermogram substantially as shown in FIG. 27.

In some embodiments, the Compound I Dioxane solvate Form M is characterized by: (a) an XRPD pattern comprising peaks at 15.3, 17.5, 19.5, 20.1, 20.7, and 26.8° 2θ±0.2° 2θ; and (b) a differential scanning calorimetry (DSC) thermogram having an endotherm with an onset of about 254° C. In some embodiments, the Compound I Dioxane solvate Form M is characterized by: (a) an XRPD pattern substantially as shown in FIG. 25; and (b) a DSC thermogram substantially as shown in FIG. 27.

Acetone Solvate Form Q

In some embodiments, the present invention provides a crystalline form of (E)-6-(4-Phenylcyclohexyl)-5-(3-trifluoromethylbenzyl)-1H-pyrimidine-2,4-dione acetone (Compound I, acetone solvate):

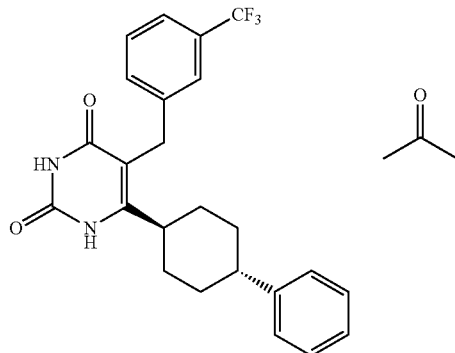

characterized by an X-ray powder diffraction (XRPD) pattern comprising three or more peaks at 15.9, 17.0, 17.2, 17.5, 18.8, 20.6, or 25.4° 2θ±0.2° 2θ, Acetone solvate Form Q.

In some embodiments, the Compound I Acetone solvate Form Q is characterized by an XRPD pattern comprising four or more peaks at 15.9, 17.0, 17.2, 17.5, 18.8, 20.6, or 25.4° 2θ±0.2° 2θ. In some embodiments, the Compound I Acetone solvate Form Q is characterized by an XRPD pattern comprising five or more peaks at 15.9, 17.0, 17.2, 17.5, 18.8, 20.6, or 25.4° 2θ±0.2° 2θ. In some embodiments, the Compound I Acetone solvate Form Q is characterized by an XRPD pattern comprising peaks at 15.9, 17.0, 17.2, 17.5, 18.8, 20.6, and 25.4° 2θ±0.2° 2θ.

In some embodiments, the Compound I Acetone solvate Form Q is characterized by an XRPD pattern further comprising one or more peaks at 7.8, 10.0, 11.0, 11.8, 12.0, 12.8, 19.3, 20.1, 20.3, 22.1, 22.5, 23.0, 24.0, 25.2, 25.9, 26.4, 26.8, 27.2, 27.9, 30.2, 31.1, or 35.6° 2θ±0.2° 2θ. In some embodiments, the Compound I Acetone solvate Form Q is characterized by an XRPD pattern further comprising two or more peaks at 7.8, 10.0, 11.0, 11.8, 12.0, 12.8, 19.3, 20.1, 20.3, 22.1, 22.5, 23.0, 24.0, 25.2, 25.9, 26.4, 26.8, 27.2, 27.9, 30.2, 31.1, or 35.6° 2θ±0.2° 2θ. In some embodiments, the Compound I Acetone solvate Form Q is characterized by an XRPD pattern further comprising three or more peaks at 7.8, 10.0, 11.0, 11.8, 12.0, 12.8, 19.3, 20.1, 20.3, 22.1, 22.5, 23.0, 24.0, 25.2, 25.9, 26.4, 26.8, 27.2, 27.9, 30.2, 31.1, or 35.6° 2θ±0.2° 2θ. In some embodiments, the Compound I Acetone solvate Form Q is characterized by an XRPD pattern further comprising four or more peaks at 7.8, 10.0, 11.0, 11.8, 12.0, 12.8, 19.3, 20.1, 20.3, 22.1, 22.5, 23.0, 24.0, 25.2, 25.9, 26.4, 26.8, 27.2, 27.9, 30.2, 31.1, or 35.6° 2θ±0.2° 2θ. In some embodiments, the Compound I Acetone solvate Form Q is characterized by an XRPD pattern further comprising peaks at 7.8, 10.0, 11.0, 11.8, 12.0, 12.8, 19.3, 20.1, 20.3, 22.1, 22.5, 23.0, 24.0, 25.2, 25.9, 26.4, 26.8, 27.2, 27.9, 30.2, 31.1, and 35.6° 2θ±0.2° 2θ.

Figure 28:
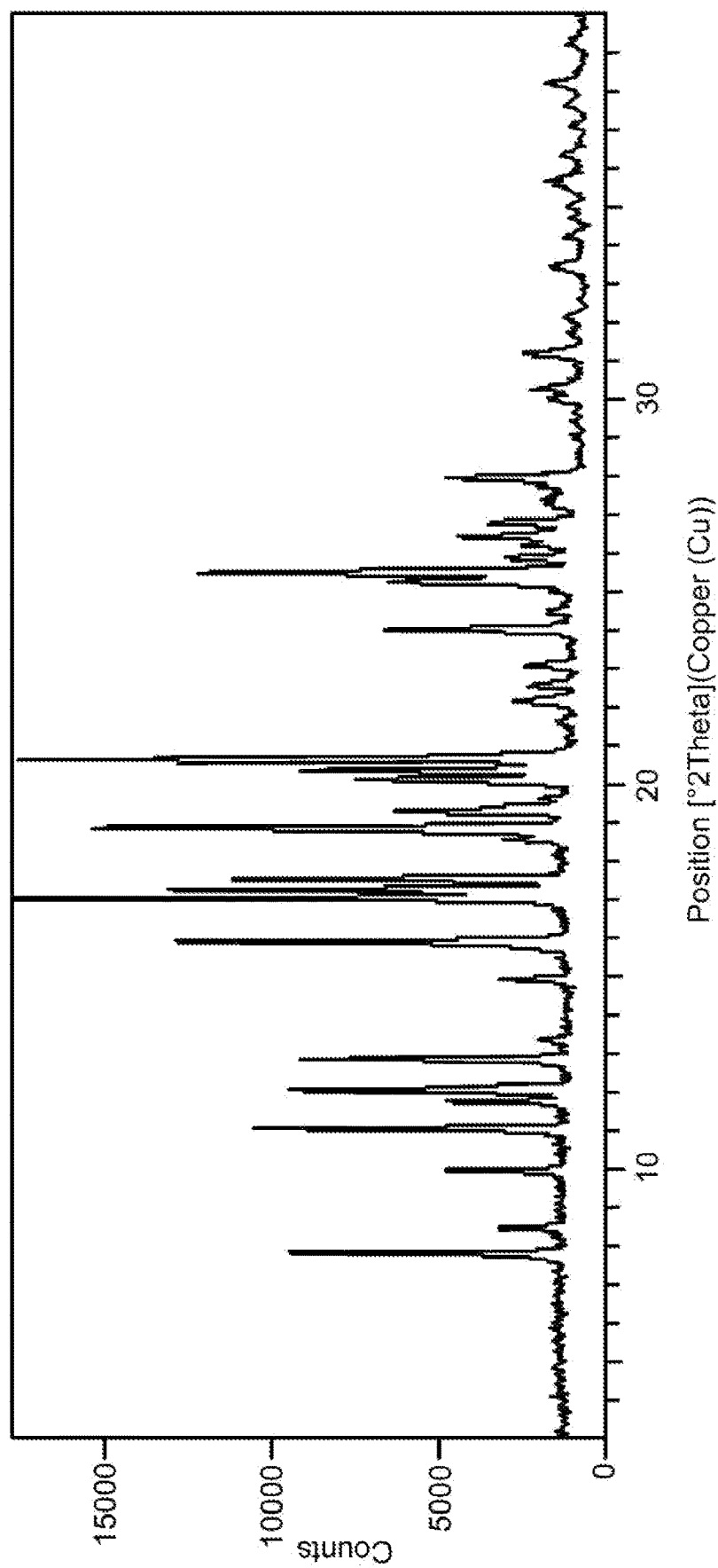
FIG. 28 shows the XRPD pattern for Compound I Acetone solvate Form Q.

In some embodiments, the Compound I Acetone solvate Form Q is characterized by an XRPD pattern comprising peaks at 7.8, 10.0, 11.0, 11.8, 12.0, 12.8, 15.9, 17.0, 17.2, 17.5, 18.8, 19.3, 20.1, 20.3, 20.6, 22.1, 22.5, 23.0, 24.0, 25.2, 25.4, 25.9, 26.4, 26.8, 27.2, 27.9, 30.2, 31.1, and 35.6° 2θ±0.2° 2θ. In some embodiments, the Compound I Acetone solvate Form Q is characterized by an XRPD pattern substantially as shown in FIG. 28.

MeOH Solvate Form R

In some embodiments, the present invention provides a crystalline form of (E)-6-(4-Phenylcyclohexyl)-5-(3-trifluoromethylbenzyl)-1H-pyrimidine-2,4-dione methanol (Compound I, methanol solvate):

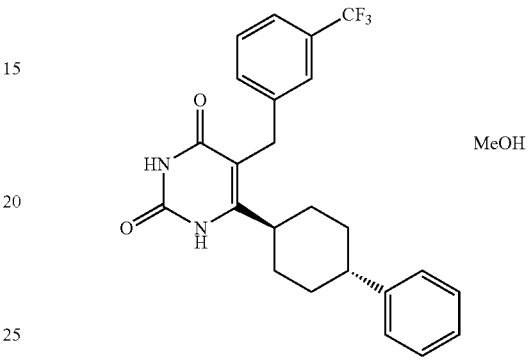

characterized by an X-ray powder diffraction (XRPD) pattern comprising three or more peaks at 10.6, 14.6, 20.3, 20.4, or 23.3° 2θ±0.2° 2θ, MeOH solvate Form R.

In some embodiments, the Compound I MeOH solvate Form R is characterized by an XRPD pattern comprising four or more peaks at 10.6, 14.6, 20.3, 20.4, or 23.3° 2θ±0.2° 2θ. In some embodiments, the Compound I MeOH solvate Form R is characterized by an XRPD pattern comprising peaks at 10.6, 14.6, 20.3, 20.4, and 23.3° 2θ±0.2° 2θ.

In some embodiments, the Compound I MeOH solvate Form R is characterized by an XRPD pattern further comprising one or more peaks at 6.8, 11.8, 12.6, 13.4, 17.7, 18.2, 20.0, 22.0, 22.2, 22.4, 24.3, 26.4, 27.1, 27.2, 30.9, or 39.3° 2θ±0.2° 2θ. In some embodiments, the Compound I MeOH solvate Form R is characterized by an XRPD pattern further comprising two or more peaks at 6.8, 11.8, 12.6, 13.4, 17.7, 18.2, 20.0, 22.0, 22.2, 22.4, 24.3, 26.4, 27.1, 27.2, 30.9, or 39.3° 2θ±0.2° 2θ. In some embodiments, the Compound I MeOH solvate Form R is characterized by an XRPD pattern further comprising three or more peaks at 6.8, 11.8, 12.6, 13.4, 17.7, 18.2, 20.0, 22.0, 22.2, 22.4, 24.3, 26.4, 27.1, 27.2, 30.9, or 39.3° 2θ±0.2° 2θ. In some embodiments, the Compound I MeOH solvate Form R is characterized by an XRPD pattern further comprising four or more peaks at 6.8, 11.8, 12.6, 13.4, 17.7, 18.2, 20.0, 22.0, 22.2, 22.4, 24.3, 26.4, 27.1, 27.2, 30.9, or 39.3° 2θ±0.2° 2θ. In some embodiments, the Compound I MeOH solvate Form R is characterized by an XRPD pattern further comprising peaks at 6.8, 11.8, 12.6, 13.4, 17.7, 18.2, 20.0, 22.0, 22.2, 22.4, 24.3, 26.4, 27.1, 27.2, 30.9, and 39.3° 2θ±0.2° 2θ.

Figure 30:
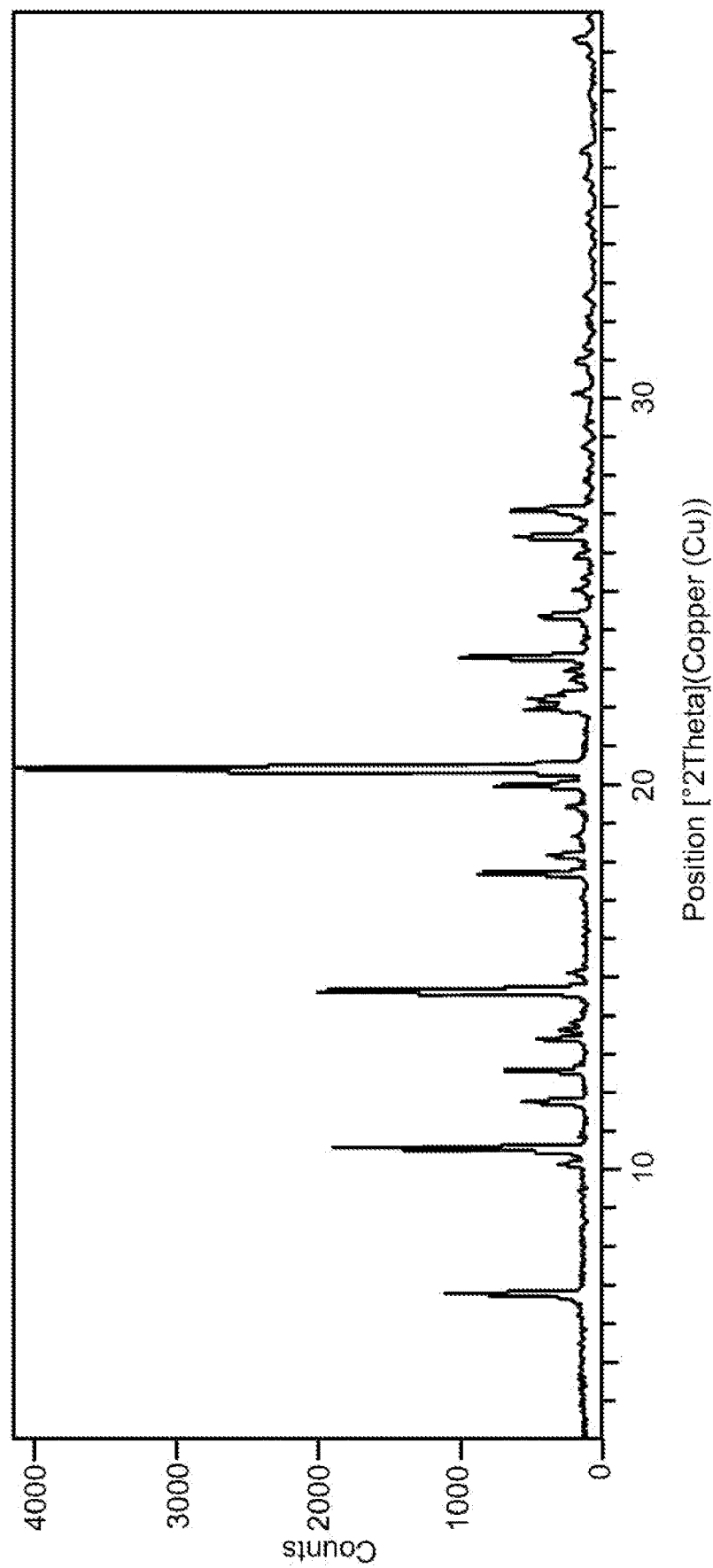
FIG. 30 shows the XRPD pattern for Compound I MeOH solvate Form R.

In some embodiments, the Compound I MeOH solvate Form R is characterized by an XRPD pattern comprising peaks at 6.8, 10.6, 11.8, 12.6, 13.4, 14.6, 17.7, 18.2, 20.0, 20.3, 20.4, 22.0, 22.2, 22.4, 23.3, 24.3, 26.4, 27.1, 27.2, 30.9, and 39.3° 2θ±0.2° 2θ. In some embodiments, the Compound I MeOH solvate Form R is characterized by an XRPD pattern substantially as shown in FIG. 30.

Figure 32:
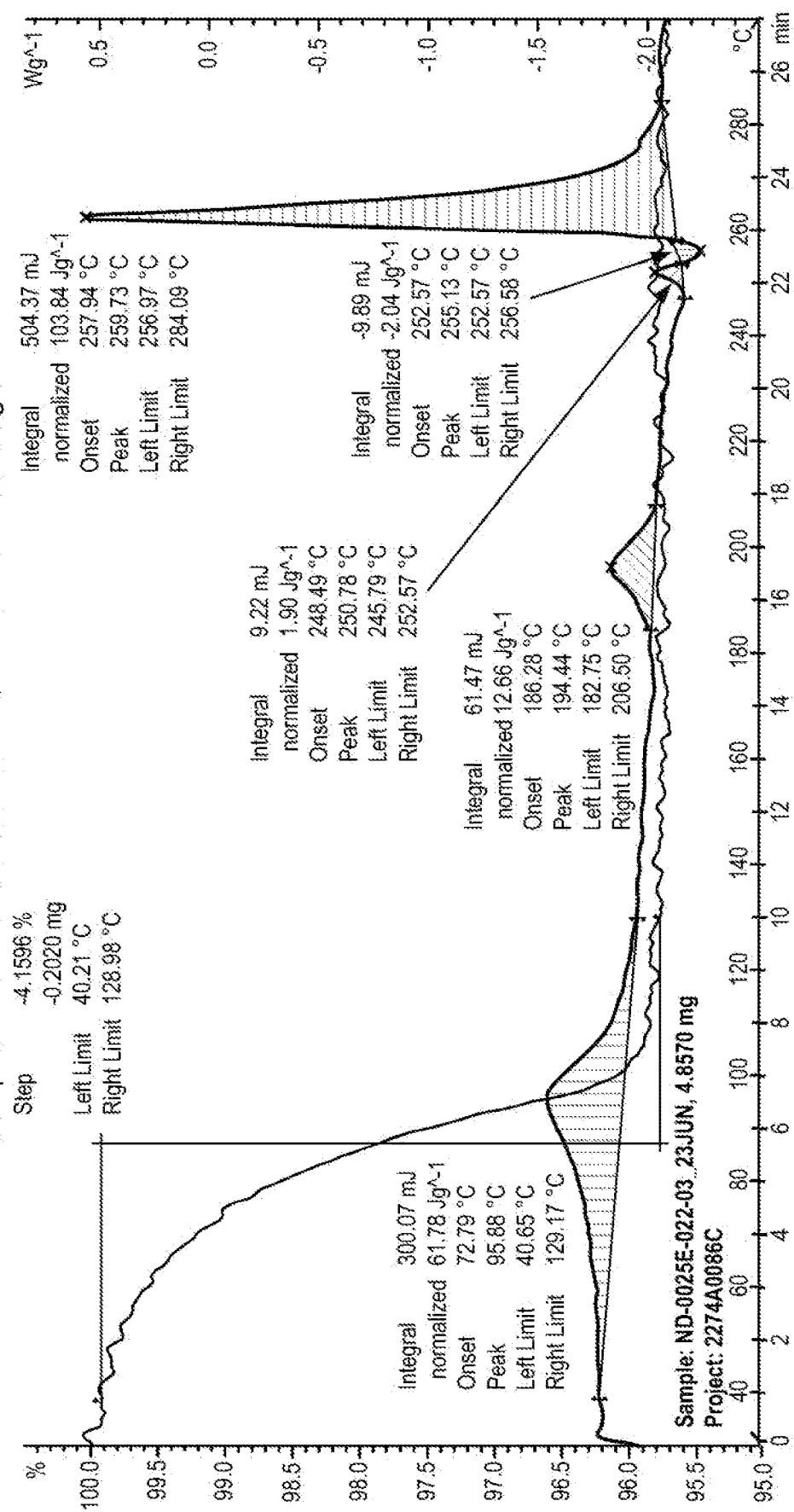
FIG. 32 shows the DSC and TGA thermogram for Compound I MeOH solvate Form R.

In some embodiments, the Compound I MeOH solvate Form R is characterized by a differential scanning calorimetry (DSC) thermogram having at least one endotherm with an onset of about 72, 186, 248, 252 or 257° C. In some embodiments, the Compound I MeOH solvate Form R is characterized by a DSC thermogram substantially as shown in FIG. 32.

In some embodiments, the Compound I MeOH solvate Form R is characterized by: (a) an XRPD pattern comprising peaks at 10.6, 14.6, 20.3, 20.4, and 23.3° 2θ±0.2° 2θ; and (b) a differential scanning calorimetry (DSC) thermogram having an endotherm with an onset of about 72, 186, 248, 252 or 257° C. In some embodiments, the Compound I MeOH solvate Form R is characterized by: (a) an XRPD pattern substantially as shown in FIG. 30; and (b) a DSC thermogram substantially as shown in FIG. 32.

IV. Methods of Preparing Solid Forms of Compound I

The solid forms of Compound I can be prepared by a variety of methods. For example, Compound I can be dissolved in a single solvent system and allowed to crystallize. Alternatively, Compound I can be crystallized from a two-solvent system by dissolving Compound I in a solvent (a good solvent), and then adding an anti-solvent (a bad solvent, i.e., a solvent in which Compound I is substantially insoluble) to the mixture causing Compound I to crystallize. Other methods of preparing crystalline Compound I include forming a slurry of solid Compound I, using a solvent mixture of a solvent and an anti-solvent.

The solvent, including the anti-solvent, can be any solvent suitable to form a solution. Typically, the solvent can be a polar solvent, which in some embodiments is a protic solvent. Other suitable solvents include non-polar solvents. Suitable solvents include, but are not limited to, water, alkanes such as heptanes, hexanes, and cyclohexane, petroleum ether, $C_1$-$C_3$ alcohols (methanol, ethanol, propanol, isopropanol), ethylene glycol and polyethylene glycol such as PEG400, alkanoates such as ethyl acetate, propyl acetate, isopropyl acetate, and butyl acetate, acetonitrile, alkanones such as acetone, butanone, methyl ethyl ketone (MEK), methyl propyl ketone (MPK) and methyl iso-butyl ketone (MIBK), ethers such as diethyl ether, methyl-t-butyl ether, tetrahydrofuran, 2-methyl-tetrahydrofuran, 1,2-dimethoxy ethane and 1,4-dioxane ("dioxane"), aromatics such as benzene and toluene, halogenated solvents such as methylene chloride, chloroform and carbon tetrachloride, dimethylsulfoxide (DMSO), and dimethylformamide (DMF). Suitable solvents also include but are not limited to halogenated $C_1$-$C_3$ alcohols (trifluoromethanol, trifluoroethanol (TFE), hexafluoroisopropanol (HFIPA). For example, the solvent can be a polar aprotic solvent such as dichloromethane, N-methylpyrrolidone, tetrahydrofuran, ethyl acetate, acetone, methyl ethyl ketone, dimethylformamide (DMF), acetonitrile (ACN), dimethyl sulfoxide (DMSO), among others. The solvent can also be a polar protic solvent such as t-butanol, n-propanol, isopropanol, ethanol, methanol, acetic acid, water, among others. The solvent can also be a nonpolar solvent, such as hexane, pentanes, petroleum ether, benzene, toluene, diethyl ether, methyl-t-butyl ether, tetrahydrofuran, 2-methyl-tetrahydrofuran, 1,2-dimethoxy ethane and 1,4-dioxane, chloroform, and carbon tetrachloride.

Two or more solvents can be used in a solvent mixture in any suitable ratio. For example, the ratio of a first solvent and a second solvent can be from 10:1 to about 1:10 (volume/volume or weight/weight), or about 10:1 to 1:5, or 10:1 to 1:1, or 10:1 to 5:1, or 5:1 to 1:5, or 5:1 to 1:1, or 4:1 to 1:1, or 3:1 to 1:1, or 2:1 to 1:1. Other solvent ratios include about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or about 1:10 (volume/volume or weight/weight).

The methods of preparing solid forms of Compound I can be performed under any suitable conditions. For example, the methods of preparing the crystalline forms of Compound I can be performed at any suitable temperature, such as, but not limited to, below room temperature, at room temperature, or above room temperature. In some embodiments, the temperature can be from about −78° C. to about 100° C., or from about 0° C. to about 50° C., or from about 10° C. to about 30° C. For example, the mixture be at a temperature of about 20° C., or 25, 30, 35, 40, 45, 50, 55, 60, 65, 70, 75, 80, 85, 90, 95 or about 100° C. The mixture can also be at a temperature of about 20° C., 15, 10, 5, 0, −5, −10, −20, −30, −40, −50, −60, −70 or about −78° C. In some embodiments, the temperature can be the reflux temperature of the particular solvent used in the method.

The methods of preparing solid forms of Compound I can include a variety of other steps. For example, the solvent can be evaporated, a seed crystal can be added to the mixture, the mixture can be heated and cooled a single time or repeatedly, etc. For example, the methods can include heating the mixture to a temperature of about 20° C., or 25, 30, 35, 40, 45, 50, 55, 60, 65, 70, 75, 80, 85, 90, 95 or about 100° C. The methods can also include cooling the mixture to a temperature of about 20° C., 15, 10, 5, 0, −5, −10, −20, −30, −40, −50, −60, −70 or about −78° C. The temperature of the mixture can be changed at any suitable rate. For example, the rate of temperature change can be from about 0.1° C./min to about 10° C./min.

The methods of preparing crystalline forms of Compound I can be performed for any suitable time. For example, the time can be for minutes, hours or days. In some embodiments, the time can be several hours, such as overnight. The methods of preparing crystalline forms of Compound I can be also be performed at any suitable pressure. For example, the pressure can be below atmospheric pressure, at about atmospheric pressure, or above atmospheric pressure.

Crystallization can be induced by methods known in the art, for example by mechanical means such as scratching or rubbing the contact surface of the reaction vessel with e.g. a glass rod. Optionally the saturated or supersaturated solution may be inoculated with seed crystals. The method of preparing solid forms of Compound I can also include a seed crystal of crystalline Compound I.

Isolation of the desired crystalline form can be accomplished by removing the solvent from the crystals. Generally, this is carried out by known methods, such as, filtration, suction filtration, decantation or centrifugation. Further isolation can be achieved by removing any excess of the solvent(s) from the crystalline form by methods known to the one skilled in the art as for example application of a vacuum, and/or by heating.

V. Pharmaceutical Compositions

In some embodiments, the present invention provides a pharmaceutical composition comprising a crystalline Compound I, and one or more pharmaceutically acceptable excipients. In some embodiments, the composition includes one or more additional therapeutic agents. In some embodiments, the present invention provides a pharmaceutical composition prepared from a crystalline Compound I, and one or more pharmaceutically acceptable excipients.

The crystalline forms of Compound I of the present invention, or compositions prepared from crystalline Compound I, can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. Crystalline Compound I of the present invention, or compositions prepared from crystalline Compound I, can also be administered by injection, that is, intravenously, intramuscularly, intracutaneously, subcutaneously, intraduodenally, or intraperitoneally. Also, crystalline Compound I described herein, or compositions prepared from crystalline Compound I, can be administered by inhalation, for example, intranasally. Additionally, crystalline Compound I of the present invention, or compositions prepared from crystalline Compound I, can be administered transdermally. Crystalline Compound I of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For preparing pharmaceutical compositions from crystalline Compound I of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, surfactants, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties and additional excipients as required in suitable proportions and compacted in the shape and size desired.

The powders, capsules and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other excipients, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers including, but not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain crystalline Compound I, or compositions prepared from crystalline Compound I, mixed with a filler or binders such as lactose or starches, lubricants such as talc or magnesium stearate, and, optionally, stabilizers.

In soft capsules, crystalline Compound I, or compositions prepared from crystalline Compound I, may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending crystalline Compound I, or a composition prepared from crystalline Compound I, in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Crystalline Compound I of the invention, or a composition prepared from crystalline Compound I, can be delivered by transdermally, by a topical route, formulated as applicator sticks, solutions, suspensions, emulsions, gels, creams, ointments, pastes, jellies, paints, powders, and aerosols.

Crystalline Compound I and compositions of the invention, or a composition prepared from crystalline Compound I, can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

The pharmaceutical formulations of crystalline Compound I of the invention can be provided as a salt and can be formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. For example, the active component can be present in an amount of 50 mg, or 100, 150, 200, 250, 300, 350, 400, 450, 500, 550, 600, 650, 700, 750, 800, 850, 900, 950, or 1000 mg. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, GR and/or MR modulator and disease or condition treated.

Single or multiple administrations of the compound formulations can be administered depending on the dosage and frequency as required and tolerated by the patient. The formulations should provide a sufficient quantity of active agent to effectively treat the disease state. Thus, in one embodiment, the pharmaceutical formulations for oral administration of the crystalline Compound I is in a daily amount of between about 0.5 to about 30 mg per kilogram of body weight per day. In an alternative embodiment, dosages are from about 1 mg to about 20 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable the compound formulations will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

Crystalline Compound I described herein, or compositions prepared from crystalline Compound I, can be used in combination, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In some embodiments, the active agents can be formulated separately. In some embodiments, the active and/or adjunctive agents may be linked or conjugated to one another.

After a pharmaceutical composition including crystalline compound I, or a composition prepared from crystalline Compound I, has been formulated in one or more acceptable carriers, it can be placed in an appropriate container and labeled for treatment of an indicated condition. For administration of crystalline Compound I, or compositions prepared from crystalline Compound I, such labeling would include, e.g., instructions concerning the amount, frequency and method of administration.

VI. Methods of Use

In some embodiments, the present invention provides a method of treating a disorder or condition through modulating a glucocorticoid receptor, comprising administering to a subject in need of such treatment, a therapeutically effective amount of a crystalline Compound I or a pharmaceutical composition of the crystalline Compound I, thereby treating the disorder or condition. In some embodiments, the present invention provides a method of treating a disorder or condition through modulating a glucocorticoid receptor, comprising administering to a subject in need of such treatment, a therapeutically effective amount of a pharmaceutical composition prepared from a crystalline Compound I of the present invention, thereby treating the disorder or condition. Such glucocorticoid receptor modulation can include modulation of GR.

In some embodiments, the present invention provides a method of treating a disorder or condition through antagonizing a glucocorticoid receptor, comprising administering to a subject in need of such treatment, a therapeutically effective amount of a crystalline Compound I or a pharmaceutical composition of the crystalline Compound I, thereby treating the disorder or condition. In some embodiments, the present invention provides a method of treating a disorder or condition through antagonizing a glucocorticoid receptor, comprising administering to a subject in need of such treatment, a therapeutically effective amount of a pharmaceutical composition prepared from a crystalline Compound I, thereby treating the disorder or condition. Such antagonization of a glucocorticoid receptor can include antagonization of GR.

In some embodiments, the present invention provides methods of modulating glucocorticoid receptor activity using the techniques described herein. In some embodiments, the method includes contacting a GR, or both, with an effective amount of crystalline Compound I, and detecting a change in GR activity, MR activity, or both, thereby treating the disorder or condition. In some embodiments, the method includes contacting a GR, or MR, or both, with an effective amount of a pharmaceutical composition prepared from a crystalline Compound I, and detecting a change in GR activity, MR activity, or both, thereby treating the disorder or condition.

In some embodiments, the glucocorticoid receptor modulator is an antagonist of GR activity, MR activity, or both (also referred to herein as "a glucocorticoid receptor antagonist"). A glucocorticoid receptor antagonist, as used herein, refers to any composition or compound which partially or completely inhibits (antagonizes) the binding of a glucocorticoid receptor agonist (e.g. cortisol, or aldosterone, and synthetic or natural cortisol or aldosterone analog) to a GR, thereby inhibiting any biological response associated with the binding of a GR to the agonist.

In some embodiments, the glucocorticoid receptor modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the androgen receptor (AR), estrogen receptor (ER) or progesterone receptor (PR). In some embodiments, the specific glucocorticoid receptor antagonist binds preferentially to GR rather than the progesterone receptor (PR). In some embodiments, the specific glucocorticoid antagonist binds preferentially to GR rather than to the androgen receptor (AR). In some embodiments, the specific glucocorticoid antagonist binds preferentially to GR rather than to the estrogen receptor (ER).

In some embodiments, the specific glucocorticoid receptor antagonist binds to the GR with an association constant (Kd) that is at least 10-fold less than the Kd for AR or PR. In some embodiments, the specific glucocorticoid receptor antagonist binds to the GR with an association constant (Kd) that is at least 100-fold less than the Kd for AR or PR. In some embodiments, the specific glucocorticoid receptor antagonist binds to the GR with an association constant (Kd) that is at least 1000-fold less than the Kd for AR, PR or ER.

In some embodiments, the disorder or condition is a substance use disorder, which may be an addiction disorder. Addictive disorders, such as substance abuse and dependence, are common disorders that involve the overuse of alcohol or drugs. Substance abuse, as a disorder, refers to the abuse of illegal substances or the abusive use of legal substances (e.g., alcohol). Substance dependence is an addictive disorder that describes continued use of drugs or alcohol, even when significant problems related to their use have developed. Signs include an increased tolerance—that is, the need for increased amounts of the substance to attain the desired effect; withdrawal symptoms with decreased use; unsuccessful efforts to decrease use; increased time spent in activities to obtain the substance; withdrawal from social and recreational activities; and continued use of the substance even with awareness of the physical or psychological problems encountered by the extent of substance use. Chemical dependence is also an addictive disorder that describes the compulsive use of chemicals (usually drugs or alcohol) and the inability to stop using them despite all the problems caused by their use. The substances frequently abused, particularly by adolescents with addictive disorders, include, but are not limited to, alcohol, marijuana, hallucinogens, cocaine, amphetamines, opiates, anabolic steroids, inhalants, methamphetamine, or tobacco.

In some embodiments, the present invention provides a method of treating a substance use disorder, comprising administering to a subject in need thereof, a therapeutically effective amount of a crystalline Compound I, or a pharmaceutical composition of the crystalline Compound I, or a pharmaceutical composition prepared from crystalline Compound I, thereby treating the substance use disorder. In some embodiments, the present invention provides a method of treating a substance use disorder, comprising administering to a subject in need thereof, a therapeutically effective amount of a pharmaceutical composition prepared from a crystalline Compound I, thereby treating the substance use disorder.

In some embodiments, the present invention provides a method of treating fatty liver disease, comprising administering to a subject in need thereof, a therapeutically effective amount of a crystalline Compound I, or a pharmaceutical composition of the crystalline Compound I, thereby treating fatty liver disease. In some embodiments, the present invention provides a method of treating fatty liver disease, comprising administering to a subject in need thereof, a therapeutically effective amount of a pharmaceutical composition prepared from a crystalline Compound I, thereby treating fatty liver disease.

In some embodiments, the disorder or condition is the fatty liver disease is alcohol related liver disease (ARLD) or nonalcoholic fatty liver disease (NAFLD). In some embodiments, the alcohol related liver disease is alcohol fatty liver disease (AFL), alcoholic steatohepatitis (ASH) or alcoholic cirrhosis.

In some embodiments, the disorder or condition is non-alcoholic fatty liver disease. In some embodiments, the nonalcoholic fatty liver disease is nonalcoholic steatohepatitis (NASH) or nonalcoholic cirrhosis. In some embodiments, the disorder or condition is nonalcoholic steatohepatitis.

NAFLD can progress to become non-alcoholic steatohepatitis (NASH), a state in which steatosis is combined with inflammation and fibrosis (steatohepatitis). NASH is a progressive disease. Over a 10-year period, up to 20% of patients with NASH will develop cirrhosis of the liver, and 10% will suffer death related to liver disease.

In some embodiments, the present invention provides a method of treating antipsychotic induced weight gain, comprising administering to a subject in need thereof, a therapeutically effective amount of a crystalline Compound I or a pharmaceutical composition of the crystalline Compound I, thereby treating antipsychotic induced weight gain. In some embodiments, the present invention provides a method of treating antipsychotic induced weight gain, comprising administering to a subject in need thereof, a therapeutically effective amount of a pharmaceutical composition prepared from a crystalline Compound I, thereby treating antipsychotic induced weight gain.

VII. Examples

Abbreviations as used herein have respective meanings as follows:

| | |
|---|---|
| DCM | Dichloromethane |
| DMSO | Dimethylsulfoxide |
| DSC | Differential scanning calorimetry |
| equiv. or eq. | Equivalents |
| EtOAc | Ethyl acetate |
| EtOH | Ethanol |
| g | Gram |
| IPA | Isopropyl alcohol |
| MEK | Methyl ethyl ketone |
| MeOH | Methanol |
| mg | Milligram |
| MIBK | Methyl isobutyl ketone |
| min | Minute |
| mL | Milliliter |
| mmol | Millimole |
| mol | Mole |
| MTBE | Methyl tert-butyl ether |
| PTFE | Polytetrafluoroethylene |
| TGA or TG/DTA | Thermogravimetric analysis or Thermogravimetric Differential Thermal Analysis |
| THF | Tetrahydrofuran |
| vol or v | Volume |
| wt | Weight |
| XRPD | X-ray powder diffraction |
| μM | Micromolar |

The solid forms of Compound I were characterized by a variety of the following methods.

X-ray Powder Diffraction (XRPD). XRPD analyses were performed using a Panalytical Xpert Pro diffractometer equipped with a Cu X-ray tube and a Pixcel detector system. The isothermal samples were analysed in transmission mode and held between low density polyethylene films. The XRPD program used included the following parameters: (1) range 3-40° 2θ, (2) step size 0.013°, (3) counting time 99 sec, and (4) about 22 min run time. XRPD patterns were sorted using HighScore Plus 2.2c software.

Differential Scanning calorimetry (DSC). DSC analyses were carried out on a Perkin Elmer Jade Differential Scanning calorimeter. Accurately weighed samples were placed in crimped aluminium pans. Each sample was heated under nitrogen at a rate of 10° C./minute to a maximum of 300° C. Indium metal was used as the calibration standard. Temperatures were reported at the transition onset to the nearest 0.01 degree.

Hyper Differential Scanning calorimetry (DSC). Hyper DSC analyses were carried out on a Perkin Elmer Diamond Differential Scanning Calorimeter. Accurately weighed samples were placed in crimped aluminium pans. Each sample was heated and cooled under helium over two cycles at a rate of 300° C./minute using a temperature range of −50 to 300° C. Indium metal was used as the calibration standard.

Thermogravimetric Differential Thermal Analysis (TG/DTA). Thermogravimetric analyses were carried out on a Mettler Toledo TGA/DSC1 STARe. The calibration standards were indium and tin. Samples were placed in an aluminium sample pan, inserted into the TG furnace and accurately weighed. The heat flow signal was stabilised for one minute at 30° C., prior to heating to 300° C. in a stream of nitrogen at a rate of 10° C./minute.

Example 1. Preparation of Compound I

Compound I can be prepared as described in U.S. Pat. No. 8,685,973, Example 6, Compound 3b.

Example 2. Compound I Form B

The crystalline Form B of Compound I can be prepared by a variety of methods described below.

Temperature cycling. The test solvent (1 mL), ethyl acetate or methyl isobutyl ketone (MIBK), was added to a sample of Compound I (~20 mg) at ambient temperature and 10 cycles of the following temperature program was performed using the Clarity crystallization station:
Heat from 20° C. to 60° C. at 1° C./min
Cool to 20° C. at 1° C./min
Stirrer speed—600 rpm Evaporation. A solution of Compound I was prepared in DMSO and filtered through a 0.2 μm PTFE filter. The filtered solution was evaporated at ambient temperature in a vial covered with perforated aluminium foil, or under a flow of N2 for high boiling solvents. The resulting solids were analysed by XRPD.

Slurry experiment. Compound I was added to a given solvent (Anisole; Cyclohexane; Dichloromethane; Ethanol; Ethanol/water azeotrope (96:4% v/v); MEK/water azeotrope (91:9% v/v); Methyl ethyl ketone (MEK); methyl t-butyl ether (MTBE); Isopropanol) until undissolved solids remained at the desired temperatures (5° C. and 40° C.). The vial was sealed and the slurry was maintained at the selected temperature and agitated by magnetic stirring for 7 days. Solids were isolated by centrifuging and decanting before air drying strips of filter paper.

Example 3. Crystallization of Compound I Form B

The crystalline Form B of Compound I can be prepared by the method described below.

Dichloromethane (8.4 volumes) is charged to the vessel, followed by the dry, crude Compound I based on its assay content relative to residual acetic acid which is determined by $^1$H-NMR.

Methanol (1.7 volumes) is then charged and the resulting mixture is then warmed to 30-35° C. to obtain a solution;

The resulting solution is polish-filtered into a second vessel, then the source vessel is washed with a mixture of dichloromethane (DCM) (2.6 volumes) and methanol (0.5 volumes) and transferred to the second vessel, affording a total batch volume of approximately 13.5 volumes;

The resulting solution is heated to reflux at atmospheric pressure (approximately 38 to 40° C.) and distilled to remove 20 volumes of solvent. Concurrent with the distillation, a solvent exchange is performed by the addition of methanol (approximately 1 volume) for each volume of distillate collected to maintain a total solvent volume of approximately 13-14 volumes during the distillation. The distillation temperature is increased as needed to maintain a reasonable distillation rate;

After approximately 3 volumes of solvent have been exchanged by methanol, the batch is seeded with a slurry containing approximately 0.05% wt/wt of recrystallized Compound I form B in approximately 0.025 volumes of methanol, then the batch is held for approximately 10 minutes while noting any changes in the batch appearance;

After completing the exchange the fourth volume of solvent with methanol, a second seeding operation is performed by again charging a slurry containing approximately 0.05% wt/wt of recrystallized Compound I form B in approximately 0.025 volumes of methanol, followed by maintaining the batch for approximately 10 minutes and noting any changes in the batch appearance;

Next a fifth volume of solvent is exchanged with methanol and the batch held for approximately 10 minutes, and the batch visually inspected to confirm whether crystallization has occurred. If crystallization has not occurred at this point a third seeding operation is then performed;

Once crystallization of the batch is confirmed the distillation and solvent exchange with methanol is continued until another 15 volumes of solvent is exchanged or a total of approximately 20 volumes of solvent has been collected since the dissolution of the crude Compound I;

Once the internal batch temperature has reached approximately 65° C. and has stabilized at approximately 64° C., another 4 volumes of solvent are collected to reduce the batch volume to approximately 10 volumes;

The resulting slurry is then cooled to approximately 10° C. over a minimum of 2 hours, then held at that temperature for at least 2 hours and filtered;

The original vessel is washed with approximately 2 volumes of methanol with stirring at approximately 10-15° C.;

The methanol is then transferred to the filter, allowed to soak on the filter cake, then removed under vacuum. This wash operation is repeated, then the solid is sampled for in-process control (IPC) analysis for wet cake purity of the solid;

The filter cake is then dried at ≤50° C. for up to 72 h, sampling after at least 12-h of drying time for IPC analysis to determine residual solvent content;

Once the IPC specification for residual solvents are met, the solid is discharged into antistatic poly liners and weighed;

The recrystallized Compound I is then sieved to break up any large lumps of solid using an oscillating sieve fitted with a 2 mm sieve screen and processed at a target oscillation speed of 0.2 m/s;

The resulting sieved Compound I is transferred to liners and weighed then the recrystallized Compound I is sampled for analysis, including X-ray powder diffraction (XRPD) to confirm that the batch of Compound I obtained as described above is consistent with polymorphic form B.

Example 4. Crystallization of Compound I Form A

The crystalline Form A of Compound I was prepared from crystalline MeOH solvate Form R of Compound I. Crystalline MeOH solvate Form R of Compound I was added to a glass vial and dried in a vacuum oven with $N_2$ purge at room temperature for 1 day. The resulting solid was collected and analyzed.

Example 5. Crystallization of Compound I Form C

The crystalline Form C of Compound I was prepared by the methods described below.

Acetone solvate Form Q. One method of preparing crystalline Form C of Compound I was to remove the solvent of crystalline Acetone solvate Form Q of Compound I under vacuum at 40° C. with a $N_2$ purge for 1 day. Alternatively, crystalline Form C of Compound I was prepared by removing the solvent of crystalline Acetone solvate Form Q of Compound I under $N_2$ at ambient temperature for 1 to 3 days.

THF solvate Form H. Another method of preparing crystalline Form C of Compound I was by drying THF solvate Form H of Compound I under $N_2$ at a temperature of 40° C. for 4 days.

Example 6. Crystallization of Compound I Form F

The crystalline Form F of Compound I was prepared from crystalline Form B of Compound I. One method was to heat crystalline Form B of Compound I to 230° C. under $N_2$, and then cooled to ambient temperature. Alternatively, crystalline Form B of compound I was heated to 255° C. under $N_2$ and held for 10 minutes, before cooling to ambient temperature.

Example 7. Crystallization of Compound I Form J

The crystalline Form J of Compound I was prepared by the methods described below.

Heating under $N_2$ with Form A. One method of preparing crystalline Form J of Compound I was to heat Crystalline Form A of Compound I under a stream of $N_2$ at 215° C., hold for 10 minutes, and then cool to ambient temperature.

Heating under $N_2$ with Form A and L. In another method, a mixture of crystalline Form A and L of Compound I was heated under a stream of $N_2$ at 215° C., held for 10 minutes, and then cooled to ambient temperature.

Example 8. Crystallization of Compound I Form L

The crystalline Form L of Compound I was prepared by the methods described below.

Melt quench technique. One method of preparing crystalline Form L of Compound I was to melt crystalline Form B of Compound I at 260° C. to 265° C. with a N2 purge. Then the compound was cooled to room temperature to form an amorphous Compound I. The amorphous Compound I was mixed with ACN at 40° C. to form a slurry. The slurry was then filtered to isolate the solid. The solid was then dried under vacuum overnight at 40° C. with $N_2$ purge to form a recrystallized Compound I Form L.

Vacuum dried. Another method was to dry crystalline Dioxane solvate Form M of Compound I under vacuum with $N_2$ purge at 40° C. overnight to form a recrystallized Compound I Form L.

Example 9. Crystallization of Compound I THF Solvate Form H

The crystalline THF solvate Form H of Compound I was prepared from Crystalline Form B. Crystalline Form B of Compound I was dissolved in 10 volumes THF at ambient temperature and then heated to 50° C. Water was then added dropwise, and a suspension was formed at a ratio of THF/$H_2$ of 62.5:37.5% v/v (10 volumes). The suspension was then cooled to ambient temperature and mixed for 1 hour. The solid in the suspension was then isolated by centrifuge filtration.

Example 10. Crystallization of Compound I AcOH Solvate Form K

The crystalline AcOH solvate Form K of Compound I was prepared by the methods described below.

Slurry experiment. Crystalline Form B of Compound I was dissolved in a mixture of AcOH/H₂O in a ratio of 90:10 v/v (10 volumes). The mixture was then heated to 75° C. and mixed for 1 hour to form a slurry. The slurry was then cooled to ambient temperature, and the solid was isolated by centrifuge filtration.

Evaporation. Crystalline Form B of Compound I was dissolved in AcOH/DCM in a ratio of 1:3 v/v (40 volumes) and evaporated under a stream of N₂ at ambient temperature for over 2 days. The resultant solid was collected and analyzed.

Example 11. Crystallization of Compound I Dioxane Solvate Form M

Slurry experiment. The crystalline Dioxane solvate Form M of Compound I was prepared from crystalline Form B of Compound I. Crystalline Form B of Compound I was dissolved in dioxane (10 volumes). The mixture was then heated to 40° C. for 48 hours to form a slurry. Afterwards, the solid was isolated by centrifuge filtration.

Example 12. Crystallization of Compound I Acetone Solvate Form 0

Slurry experiment. The crystalline Acetone solvate Form Q of Compound I was prepared from crystalline Form B of Compound I. Crystalline Form B of Compound I was dissolved in acetone and cooled to a temperature of at 5° C. The mixture was stirred for 20 hours, 3 days, or 4 days at 5° C. Afterwards, the solid was isolated by filtration.

Example 13. Crystallization of Compound I MeOH Solvate Form R

Slurry experiment. The crystalline MeOH solvate Form R of Compound I was prepared from crystalline AcOH solvate Form K of Compound I. Crystalline AcOH solvate Form K of Compound I was dissolved in MeOH, heated to 60° C., and mixed for 1 hour to form a slurry. The slurry was then cooled to 30° C. over 1 hour. Then the suspension was further cooled to 15° C. over 30 minutes. The suspension was then mixed for between 3 hours and 18 hours. Afterwards, the solid was isolated by Buchner filtration and pull dried for 5 to 10 minutes.

Although the foregoing invention has been described in some detail by way of illustration and example for purposes of clarity of understanding, one of skill in the art will appreciate that certain changes and modifications may be practiced within the scope of the appended claims. In addition, each reference, including all of the U.S. patents, U.S. patent application publications, U.S. patent applications, foreign patents, foreign patent applications and non-patent publications referred to in this specification are incorporated herein by reference, in their entirety, to the extent not inconsistent with the present description. Where a conflict exists between the instant application and a reference provided herein, the instant application shall dominate.

What is claimed is:

1. A crystalline anhydrate form of (E)-6-(4-Phenylcyclohexyl)-5-(3-trifluoromethylbenzyl)-1H-pyrimidine-2,4-dione (Compound I):

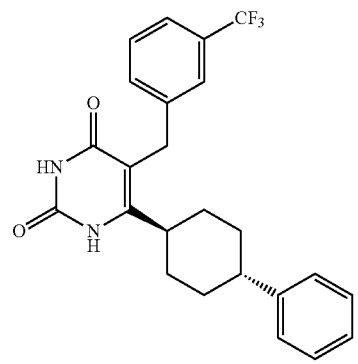 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 16.3, 17.1, 18.7, 19.9, 22.1, or 22.3° 2θ±0.2° 2θ, Form A.

2. The crystalline form of claim 1, characterized by an XRPD pattern comprising peaks at 9.5, 14.0, 15.5, 16.3, 17.1, 18.5, 18.7, 19.5, 19.9, 21.3, 22.1, 22.3, and 23.3° 2θ±0.2° 2θ.

3. The crystalline form of claim 1, characterized by an XRPD pattern substantially as shown in FIG. 4.

4. A crystalline anhydrate form of (E)-6-(4-Phenylcyclohexyl)-5-(3-trifluoromethylbenzyl)-1H-pyrimidine-2,4-dione (Compound I):

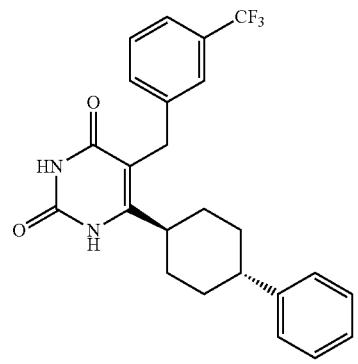 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 17.3, 17.9, 18.3, 18.4, 21.3, or 21.8° 2θ±0.2° 2θ, Form C.

5. The crystalline form of claim 4, characterized by an XRPD pattern comprising peaks at 8.8, 10.6, 14.3, 15.1, 17.3, 17.7, 17.9, 18.3, 18.4, 19.3, 21.3, 21.8, 22.5, 26.2, and 27.6° 2θ±0.2° 2θ.

6. The crystalline form of claim 4, characterized by an XRPD pattern substantially as shown in FIG. 7.

7. A crystalline anhydrate form of (E)-6-(4-Phenylcyclohexyl)-5-(3-trifluoromethylbenzyl)-1H-pyrimidine-2,4-dione (Compound I):

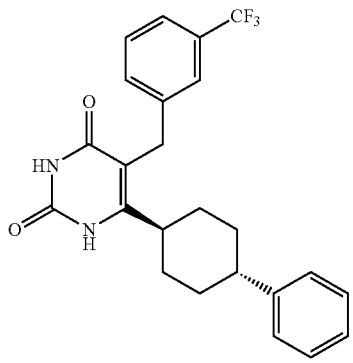 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 15.9, 16.4, 16.8, 17.3, 19.0, 21.1, or 25.8° 2θ±0.2° 2θ, Form F.

8. The crystalline form of claim 7, characterized by an XRPD pattern comprising peaks at 9.3, 9.7, 14.1, 14.3, 15.9, 16.4, 16.8, 17.3, 17.8, 19.0, 19.4, 20.4, 20.7, 21.1, 21.5, 22.3, 23.8, 25.1, 25.8, 26.7, 31.2, and 35.3° 2θ±0.2° 2θ.

9. The crystalline form of claim 7, characterized by an XRPD pattern substantially as shown in FIG. 10.

10. A crystalline anhydrate form of (E)-6-(4-Phenylcyclohexyl)-5-(3-trifluoromethylbenzyl)-1H-pyrimidine-2,4-dione (Compound I):

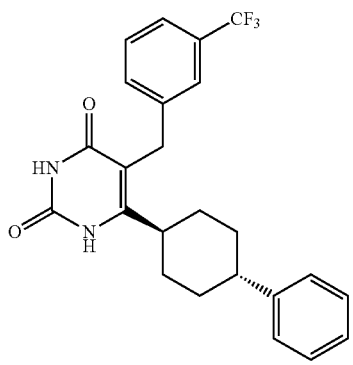 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 6.0, 13.1, 17.3, 18.8, 19.8, 20.1, or 21.9° 2θ±0.2° 2θ, Form J.

11. The crystalline form of claim 10, characterized by an XRPD pattern comprising peaks at 6.0, 13.1, 13.7, 15.6, 17.3, 18.1, 3, 18.8, 19.1, 19.8, 20.1, 21.9, 27.4° 2θ±0.2° 2θ.

12. The crystalline form of claim 10, characterized by an XRPD pattern substantially as shown in FIG. 16.

13. A crystalline anhydrate form of (E)-6-(4-Phenylcyclohexyl) (3-trifluoromethylbenzyl)-1H-pyrimidine-2,4-dione (Compound I):

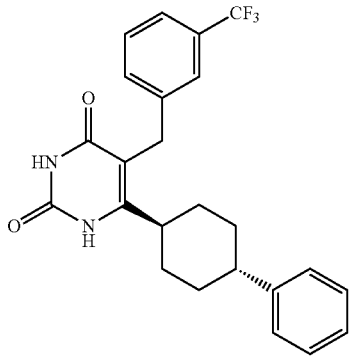 [SMILES: O=c1[nH]c(=O)c(Cc2cccc(C(F)(F)F)c2)c([C@H]2CC[C@H](c3ccccc3)CC2)[nH]1]

characterized by an X-ray powder diffraction (XRPD) pattern comprising three or more peaks at 14.6, 15.5, 19.4, 19.7, or 22.2° 2θ±0.2° 2θ, Form L.

14. The crystalline form of claim 13, characterized by an XRPD pattern comprising peaks at 13.1, 13.6, 14.6, 15.5, 17.2, 18.6, 19.4, 19.7, 20.6, 21.7, 22.2, 23.2, 24.5, 26.1, 27.5, and 28.6° 2θ±0.2° 2θ.

15. The crystalline form of claim 13, characterized by an XRPD pattern substantially as shown in FIG. 22.

16. A pharmaceutical composition comprising a crystalline form of claim 1, and one or more pharmaceutically acceptable excipients.

17. The pharmaceutical composition of claim 16, further comprising one or more additional therapeutic agents.

\* \* \* \* \*